United States Patent
Mosberg et al.

(10) Patent No.: US 10,519,114 B2
(45) Date of Patent: Dec. 31, 2019

(54) PEPTIDOMIMETICS AND METHODS OF USING THE SAME

(71) Applicant: The Regents of the University of Michigan, Ann Arbor, MI (US)

(72) Inventors: Henry Mosberg, Ann Arbor, MI (US); Deanna Montgomery, Ann Arbor, MI (US); Aaron Bender, Spring Hill, TN (US); Anthony Nastase, Ann Arbor, MI (US); Sean Henry, Ann Arbor, MI (US); Aubrie Harland, Durham, NC (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/705,497

(22) Filed: Sep. 15, 2017

(65) Prior Publication Data

US 2018/0072677 A1 Mar. 15, 2018

Related U.S. Application Data

(60) Provisional application No. 62/538,016, filed on Jul. 28, 2017, provisional application No. 62/395,136, filed on Sep. 15, 2016.

(51) Int. Cl.
| | | |
|---|---|---|
| C07D 215/42 | (2006.01) | |
| C07D 401/06 | (2006.01) | |
| C07D 405/06 | (2006.01) | |
| C07D 471/06 | (2006.01) | |
| C07D 471/04 | (2006.01) | |
| C07D 405/04 | (2006.01) | |
| C07D 223/16 | (2006.01) | |
| C07D 311/68 | (2006.01) | |
| C07C 237/04 | (2006.01) | |
| C07D 335/06 | (2006.01) | |
| C07D 215/58 | (2006.01) | |
| C07D 487/04 | (2006.01) | |
| C07C 237/20 | (2006.01) | |

(52) U.S. Cl.
CPC .......... *C07D 215/42* (2013.01); *C07C 237/04* (2013.01); *C07C 237/20* (2013.01); *C07D 215/58* (2013.01); *C07D 223/16* (2013.01); *C07D 311/68* (2013.01); *C07D 335/06* (2013.01); *C07D 401/06* (2013.01); *C07D 405/04* (2013.01); *C07D 405/06* (2013.01); *C07D 471/04* (2013.01); *C07D 471/06* (2013.01); *C07D 487/04* (2013.01); *C07C 2602/08* (2017.05); *C07C 2602/10* (2017.05)

(58) Field of Classification Search
None
See application file for complete search history.

(56) References Cited

U.S. PATENT DOCUMENTS

| 4,661,913 A | 4/1987 | Wu et al. |
| 5,466,468 A | 11/1995 | Schneider et al. |
| 2008/0269143 A1 | 10/2008 | Lazarus et al. |

OTHER PUBLICATIONS

Harland et al., Further Optimization and Evaluation of Bioavailabe, Mixed-Efficacy μ-Opioid Receptor (MOR) Agonists/δ-Opioid Receptor (DOR) Antagonists: Balancing MOR and DOR Affinities. Journal of Medicinal Chemistry, 2015, 58, 8952-8969.*
Mosberg et al., Opioid Peptidomimetics: Leads for the Design of Bioavailable Mixed Efficacy μ Opioid Receptor (MOR) Agonist/ δ Opioid Receptor (DOR) Antagonist Ligands. Journal of Medicinal Chemistry, 2013, 56, 2139-2149.*
Bender et al., Rapid Synthesis of Boc-2',6'-dimethyl-L-tyrosine and Drivatives and Incorporation into Opioid Peptidomimetics. ACS Medicinal Chemistry Letters, 2015, 6, 1199-1203.*
Harland et al., Effect of N-Substitutions on the Tetrahydroquinoline (THQ) Core of Mixed-Efficacy μ-Opioid Receptor (MOR)/δ-Opioid Receptor (DOR) Ligands. Journal of Medicinal Chemistry, 2016, 59, 4985-4998.*
Chemical Abstract Registry No. 1939415-21-0, indexed in the Registry File on STN CAS Online Jun. 27, 2016.*
Abdelhamid et al., Selective blockage of delta opioid receptors prevents the development of morphine tolerance and dependence in mice, *J. Pharm. Exp. Ther.*, 258:299-303 (1991).
Balboni et al., Potent delta-opioid receptor agonists containing the Dmt-Tic pharmacophore, *J. Med. Chem.*, 45:5556-63 (2002).
Balboni et al., Synthesis and opioid activity of N,N-dimethyl-Dmt-Tic-NH—CH(R)-R' analogues: acquisition of potent delta antagonism, *Bioorg. Med. Chem.*, 11:5435-41 (2003).
Benyamin et al., Opioid complications and side effects, *Pain Physician*, 11:S105-20 (2008).
Cechetto et al., Immunoelectron microscopy provides evidence that tumor necrosis factor receptor-associated protein 1 (TRAP-1) is a mitochondrial protein which also localizes at specific extramitochondrial sites, *Exp. Cell. Res.*, 260:30-9 (2000).
Clapp et al., Cardiovascular and metabolic responses to two receptor-selective opioid agonists in pregnant sheep, *Am. J. Obstet. Gynecol.*, 178(2):397-401 (1998).

(Continued)

*Primary Examiner* — Po-Chih Chen
(74) *Attorney, Agent, or Firm* — Marshall, Gerstein & Borun LLP

(57) ABSTRACT

Disclosed herein are compounds useful for modulating the mu-opioid receptor ("MOR") and/or delta-opioid receptor ("DOR"), and methods of using these compounds to treat diseases and conditions, such as pain. In particular, disclosed herein are compounds of Formula (I) and pharmaceutically acceptable salt thereof:

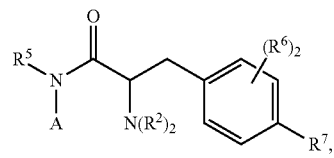

wherein the substituents are as described.

11 Claims, No Drawings

(56) References Cited

OTHER PUBLICATIONS

Greene et al., Protective Groups in Organic Synthesis, 3rd edition, John Wiley & Sons: New York, (1999).
Harris et al., A simple microcomputer interface for tail-flick determination, *J. Pharmacol. Meth.*, 20:103-8 (1988).
Hepburn et al., Differential effects of naltrindole on morphine-induced tolerance and physical dependence in rats, *J. Pharm. Exp. Ther.*, 281:1350-6 (1997).
Hubbell et al., Antagonism at delta opioid receptors blocks cocaine's, but not morphine's, enhancement of responding for intracranial stimulation, *Exp. Clin. Psychopharmacol.*, 3(2):123-8 (1995).
Jutkiewicz et al., The convulsive and electroencephalographic changes produced by nonpeptidic delta-opioid agonists in rats: comparison with pentylenetetrazol, *J. Pharmacol. Exp. Ther.*, 317(3):1337-48 (2006).
Kest et al., An antisense oligodeoxynucleotide to the delta opioid receptor (DOR-1) inhibits morphine tolerance and acute dependence in mice, *Brain Res. Bull.*, 39:185-188 (1996).
Larsen et al., The Merrifield peptide synthesis studied by near-infrared Fourier-transform Raman spectroscopy, *J. Am. Chem. Soc.*, 115(14):6247-6253 (1993).
Lazarus et al., Function of negative charge in the "address domain" of deltorphins, *Med Chem.*, 34:1350-9 (1991).
Merrifield, Solid phase peptide synthesis. I. The Synthesis of a Tetrapeptide, *J. Am. Chem. Soc.*, 85(14):2149-54 (1963).

Nielsen et al., A novel delta opioid receptor antagonist, SoRI-9409, produces a selective and long-lasting decrease in ethanol consumption in heavy-drinking rats, *Biol. Psychiatry*, 64(11):974-81 (2008).
O'Donnell et al., Solid-phase unnatural peptide synthesis (UPS), *J. Am. Chem. Soc.*, 118: 6070-6071 (1996).
Przydzial et al., Roles of residues 3 and 4 in cyclic tetrapeptide ligand recognition by the kappa-opioid receptor, *Pept. Res.*, 65(3):333-42 (2005).
Salvadori et al., Further studies on the Dmt-Tic pharmacophore: hydrophobic substituents at the C-terminus endow delta antagonists to manifest mu agonism or mu antagonism, *Med. Chem.*, 42:5010-9 (1999).
Sasaki et al., Endomorphin 2 analogues containing Dmp residue as an aromatic amino acid surrogate with high mu-opioid receptor affinity and selectivity, *Bioorg. Med. Chem.*, 11:675-8 (2003).
Smith et al., March's Advanced Organic Chemistry: Reactions, Mechanisms and Structure, 5th edition, John Wiley & Sons: New York, (2001).
Smith et al., Solid-phase peptide synthesis and biological activity of bovine thymopoietin II (bTP-II), *Int. J. Peptide Protein Res.*, 44:183 (1994).
Woolfe et al., The Evaluation of the analgesic action of pethidine hydrochloride (DEMEROL) J Pharmacol Exp Ther. 1944;80:300-7 (1944).
Zhu et al., Retention of supraspinal delta-like analgesia and loss of morphine tolerance in delta opioid receptor knockout mice, Neuron, 24:243-52 (1999).

\* cited by examiner

PEPTIDOMIMETICS AND METHODS OF USING THE SAME

STATEMENT OF GOVERNMENT SUPPORT

This invention was made with government support under grant number DA003910 awarded by the National Institutes of Health. The Government has certain rights in the invention.

BACKGROUND

Technical Field

The present disclosure relates to compounds capable of modulating the mu-opioid receptor ("MOR"), the delta-opioid receptor ("DOR"), and/or the kappa-opioid receptor ("KOR"), and methods of using these receptor modulators for the treatment of pain.

Description of Related Technology

Opioid receptors are G protein-coupled receptors found in the brain, spinal cord, and digestive tract that have a wide variety of biological function, including controlling pain sensation. There are three recognized "classical" opioid receptor subtypes: mu-opioid receptors (MOR), delta-opioid receptors (DOR), and kappa-opioid receptors (KOR). The natural ligands for opioid receptors include enkephalins, endorphins, endomorphins, and dynorphins, and an abundance of non-peptide or synthetic ligands have been discovered or developed to modulate opioid receptor activity.

Opioid drugs, including morphine, are the primary treatment for severe pain, e.g., post-operative and chronic pain conditions. Unfortunately, the use of opioids can lead to the development of a number of undesirable side effects, such as nausea, pruritis, sedation, mood swings, respiratory depression, constipation, and perhaps most problematically, dependence/addiction and tolerance. (Benyamin, R. et al. Pain Physician 2008; 11:S105-S120).

Despite a considerable amount of research into opioid-based therapeutics, there remains a need for analgesics that exhibit little or none of the adverse effects associated with traditional opioid use.

SUMMARY

In one aspect, the disclosure provides compounds of Formula (I):

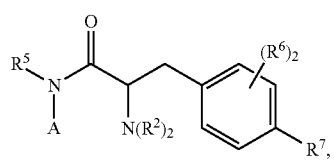

(I)

wherein A is a formula selected from the group consisting of

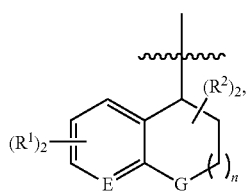

(B)

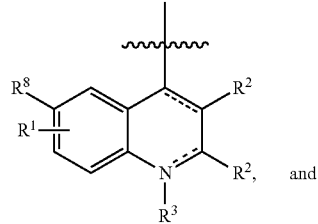

(C)

and

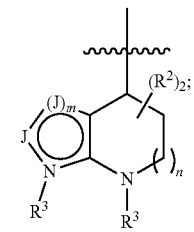

(D)

E is $CR^1$ or N; G is $C(R^2)_2$, O, S, or $SO_2$; each J independently is $CR^1$ or $NR^3$; m is 1 or 2; n is 0, 1, or 2; ---- indicates an optional double bond; each $R^1$ independently is H, halo, $C_{1-6}$haloalkyl, $C_{1-6}$alkyl, $C_{0-6}$alkylenearyl, $C_{0-6}$alkyleneheteroaryl, $C_{0-6}$alkylenecycloalkyl, $C_{0-6}$alkyleneheterocycloalkyl, $C_{0-3}$alkyleneOR$^4$, SR$^4$, SO$_2$R$^4$, C(O)N(R$^4$)$_2$, C(O)OR$^4$, or C(O)SR$^4$; and wherein for formula (B), at least one $R^1$ is other than H; each $R^2$ independently is H or $C_{1-6}$alkyl; $R^3$ is H, $C_{1-6}$alkyl, $C_{0-3}$alkyleneC(O)R$^4$, $C_{0-3}$alkyleneC(O)OR$^4$, $C_{0-3}$alkyleneC(O)NHR$^4$, or absent; when A is formula (C), $R^3$ and $R^1$ can connect to form a 5-7-membered ring; $R^4$ is H, $C_{1-6}$alkyl, $C_{0-3}$alkylene-$C_{3-6}$cycloalkyl, $C_{1-3}$alkylene-$OC_{1-6}$alkyl, or $C_{0-3}$alkylenearyl; $R^5$ is H, $C_{1-3}$ alkyl, or $C_{3-6}$cycloalkyl; each $R^6$ independently is H, $C_{1-3}$alkyl, OH, $C_{1-3}$alkoxy, halo, or C(O)N(R$^3$)$_2$, and at least one $R^6$ is not H; $R^7$ is H, $C_{1-3}$alkyl, OH, $C_{0-3}$alkoxy, halo, or C(O)N(R$^3$)$_2$; and $R^8$ is H, halo, $C_{1-6}$alkyl, $C_{0-6}$alkylenearyl, $C_{0-6}$alkyleneheteroaryl, $C_{1-6}$alkylenecycloalkyl, $C_{1-6}$alkyleneheterocycloalkyl, O-aryl, S-aryl, or SO$_2$-aryl; with the proviso that (a) when A is

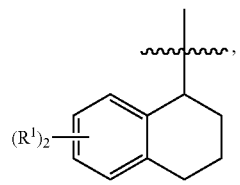

then $R^1$ is not $CH_2$naphthyl, $CH_2$phenyl, or $CH_2$cyclohexyl; and (b) when (i) A is formula (C), (ii) each ---- indicates a single bond, (iii) $R^3$ is H or $C_{0-3}$alkyleneC(O)R$_4$, (iv) $R^5$ is H, $R^7$ is H or OH, and (v) $R^8$ is unsubstituted $CH_2$aryl, unsubstituted $CH_2CH_2$aryl, unsubstituted $CH_2$heteroaryl, unsubstituted $CH_2$cycloalkyl, or unsubstituted $CH_2$heterocycloalkyl, then at least one of $R^1$ and $R^2$ is other than H; or a pharmaceutically acceptable salt thereof.

In some embodiments, A is formula (B). In various embodiments, E is $CR^1$. In some cases, E is N. In some embodiments, G is $C(R^2)_2$. In various cases, G is O. In some embodiments, G is S. In some cases, G is $SO_2$. For example, A is selected from the group consisting of

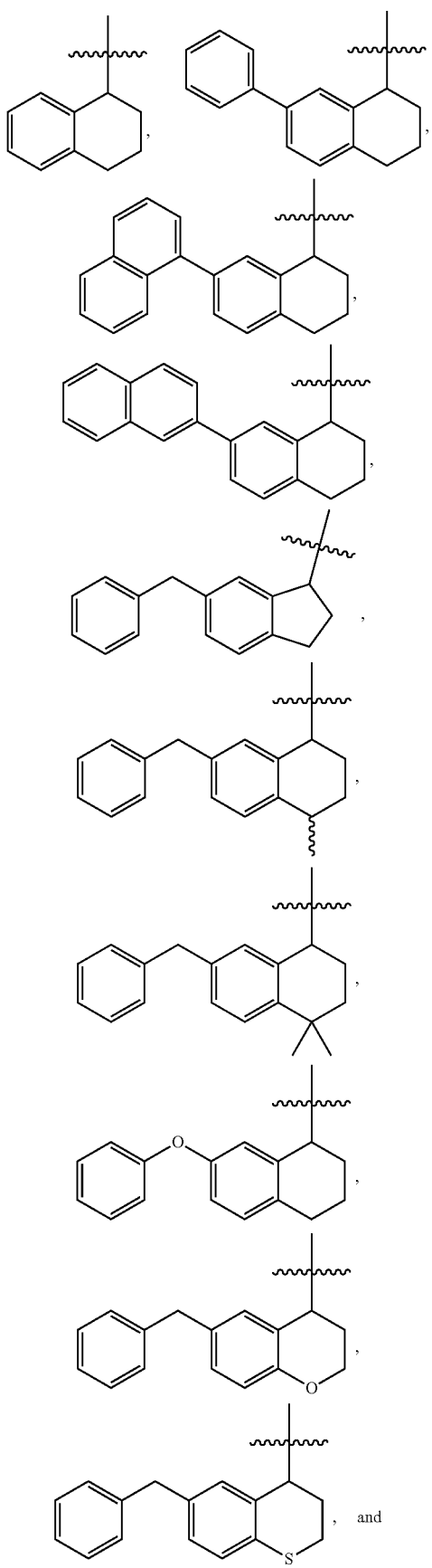

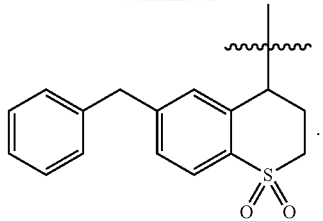

In various cases, A is formula (C). In some cases, $R^8$ is halo or $C_{1-6}$alkyl. In some embodiments, $R^8$ is Br, pentyl, or hexyl. In some cases, $R^8$ is $C_{0-6}$alkylenearyl, $C_{1-6}$alkyleneheteroaryl, $C_{1-6}$alkylenecycloalkyl, or $C_{1-6}$alkyleneheterocycloalkyl. In various embodiments, $R^8$ is $C_{0-1}$alkylenearyl, $C_1$alkyleneheteroaryl, $C_1$alkylenecycloalkyl, or $C_1$alkyleneheterocycloalkyl. In various embodiments, $R^8$ is phenyl, benzyl,

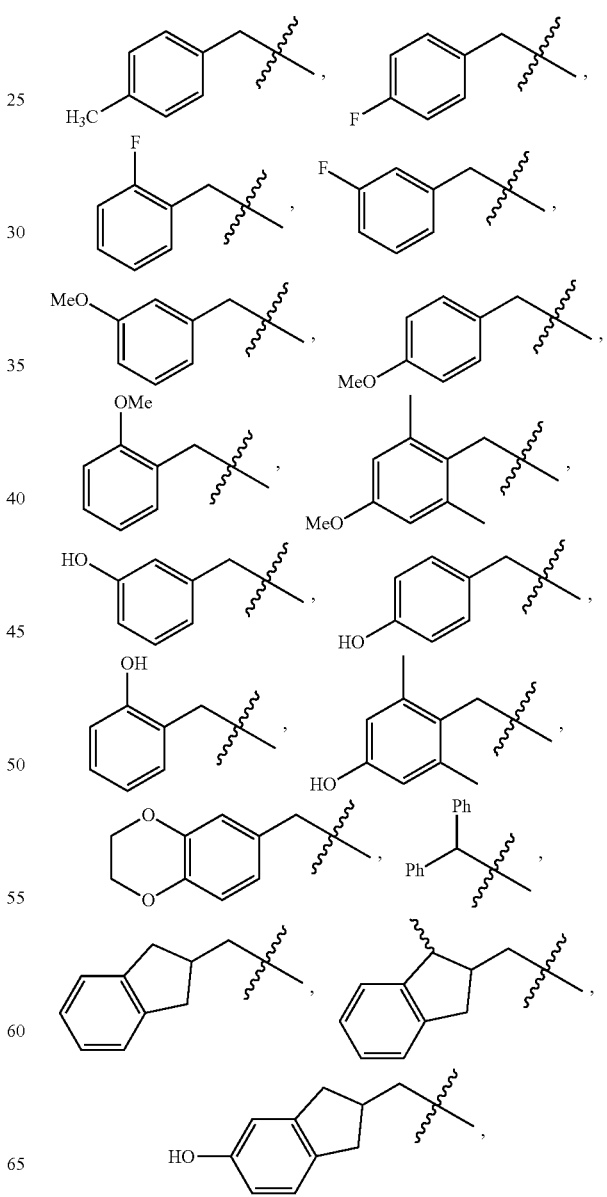

-continued
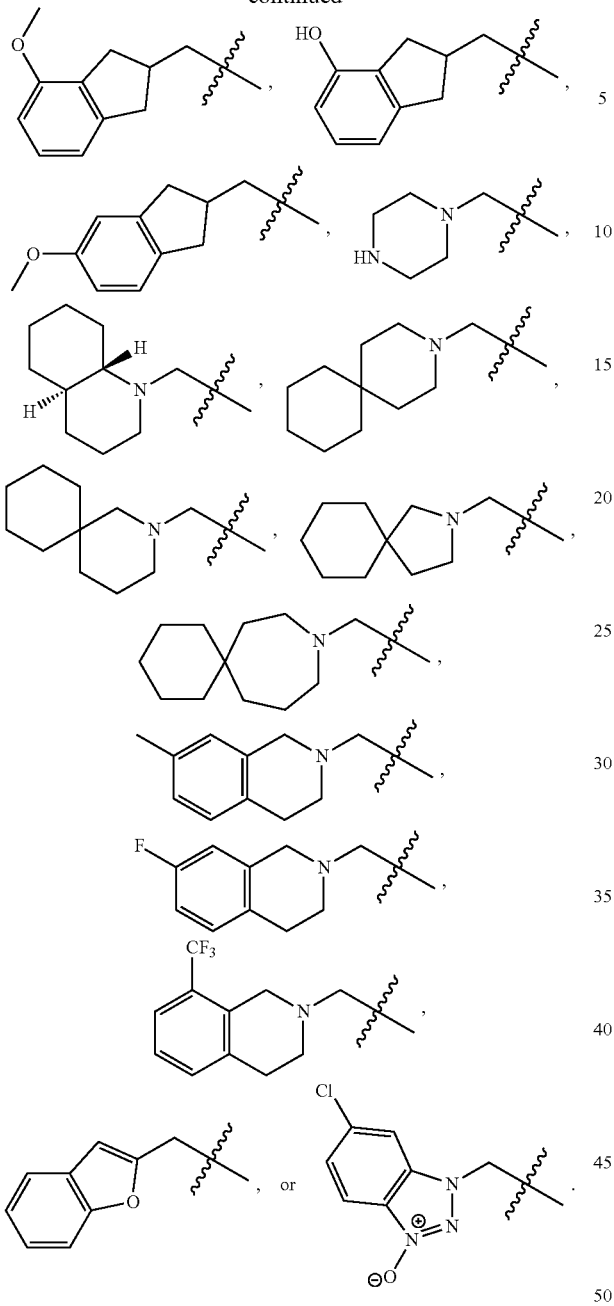
In various cases, $R^8$ is O-aryl, S-aryl, or $SO_2$-aryl. In some embodiments, $R^8$ is OPh, SPh, $SO_2$Ph,
For example, A is selected from the group consisting of
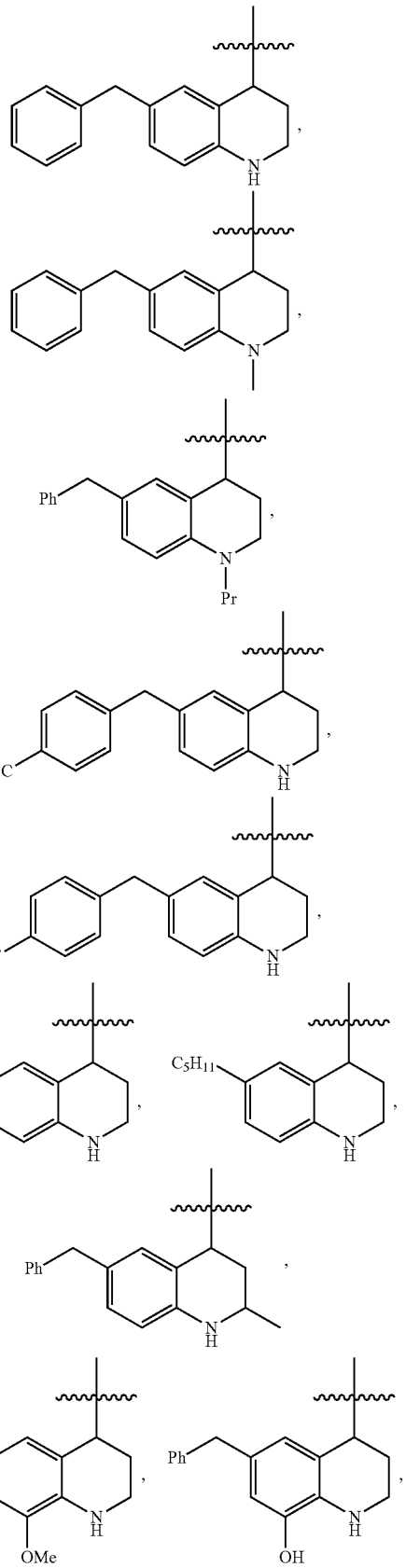

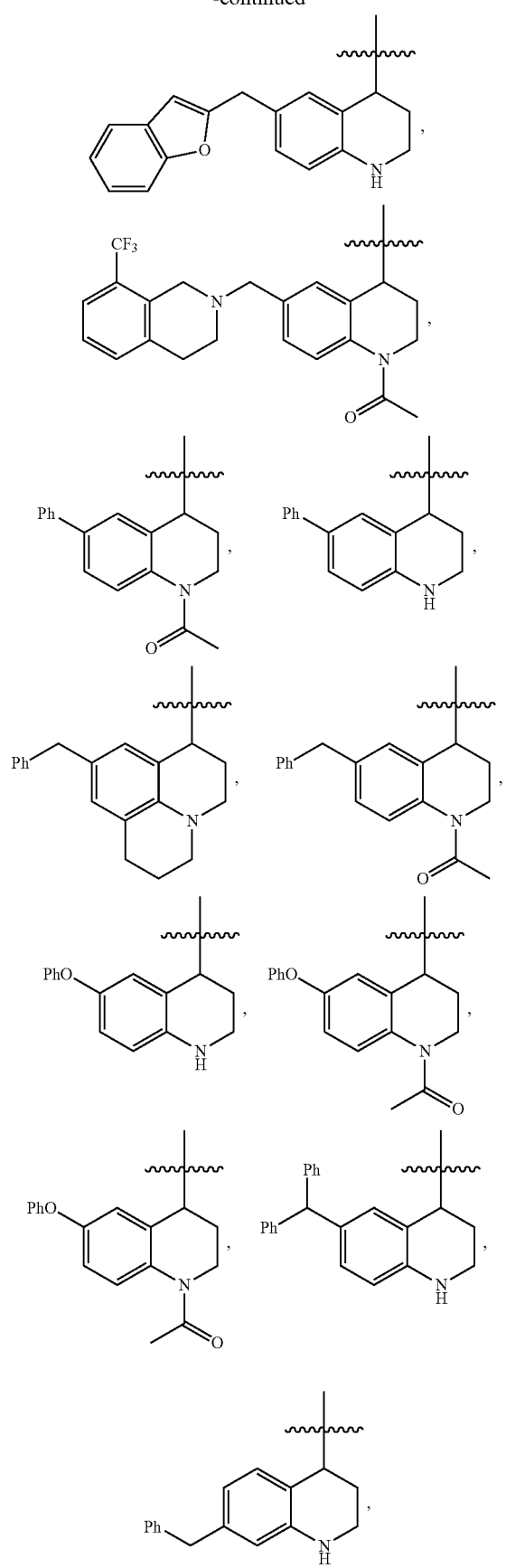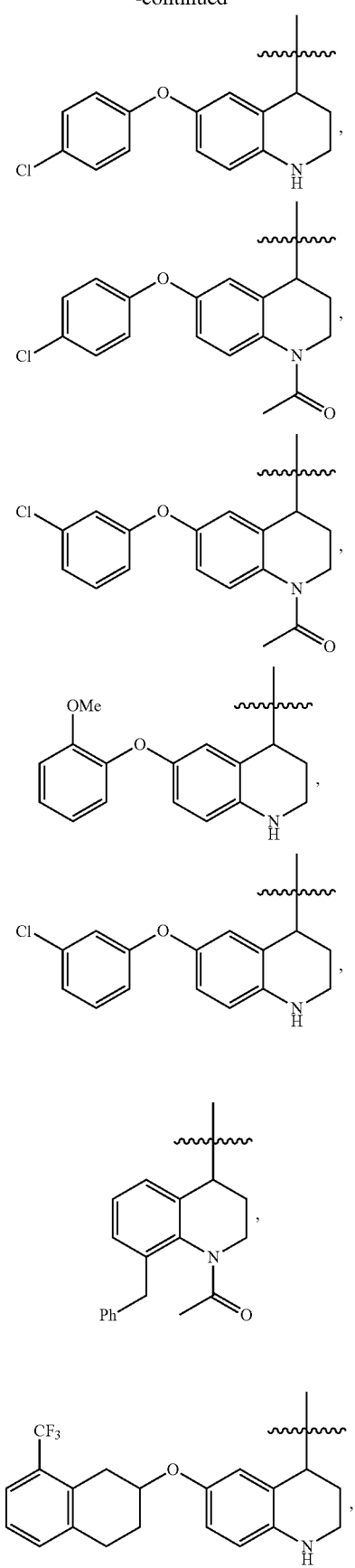

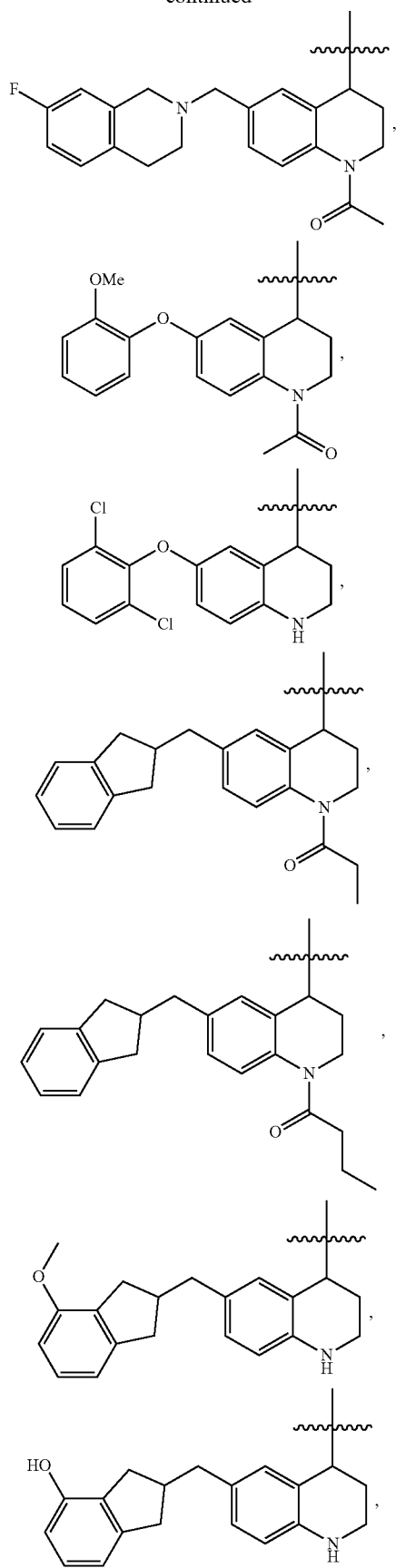
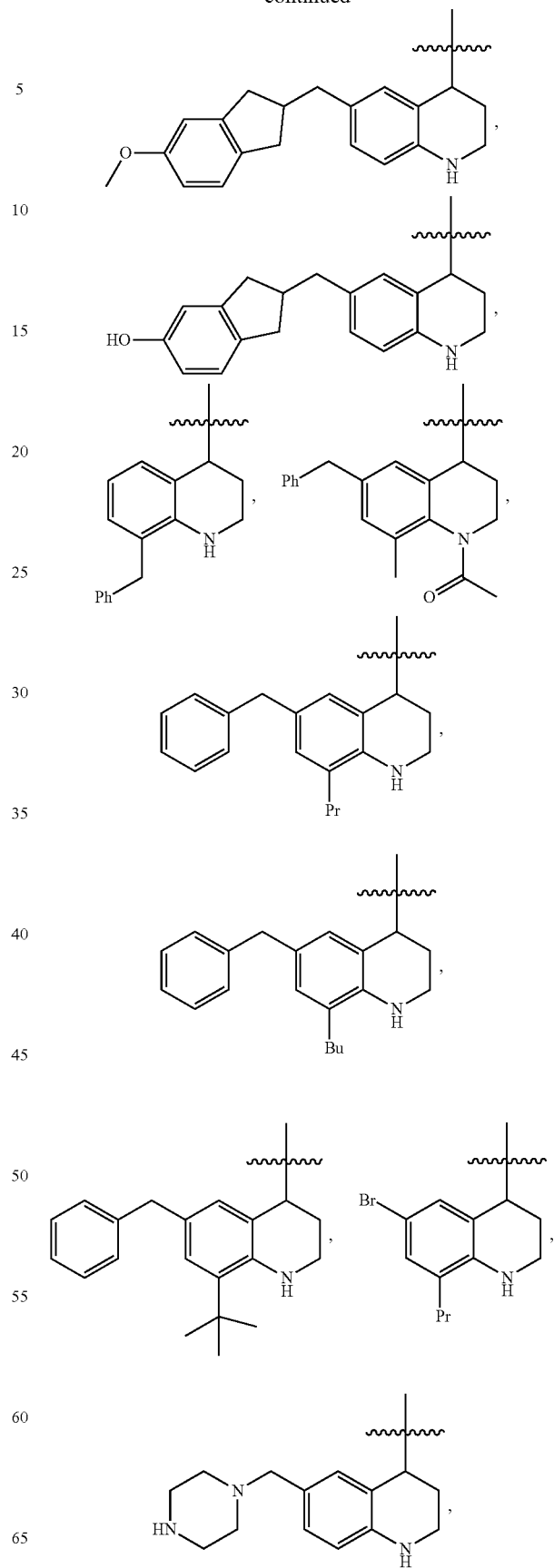

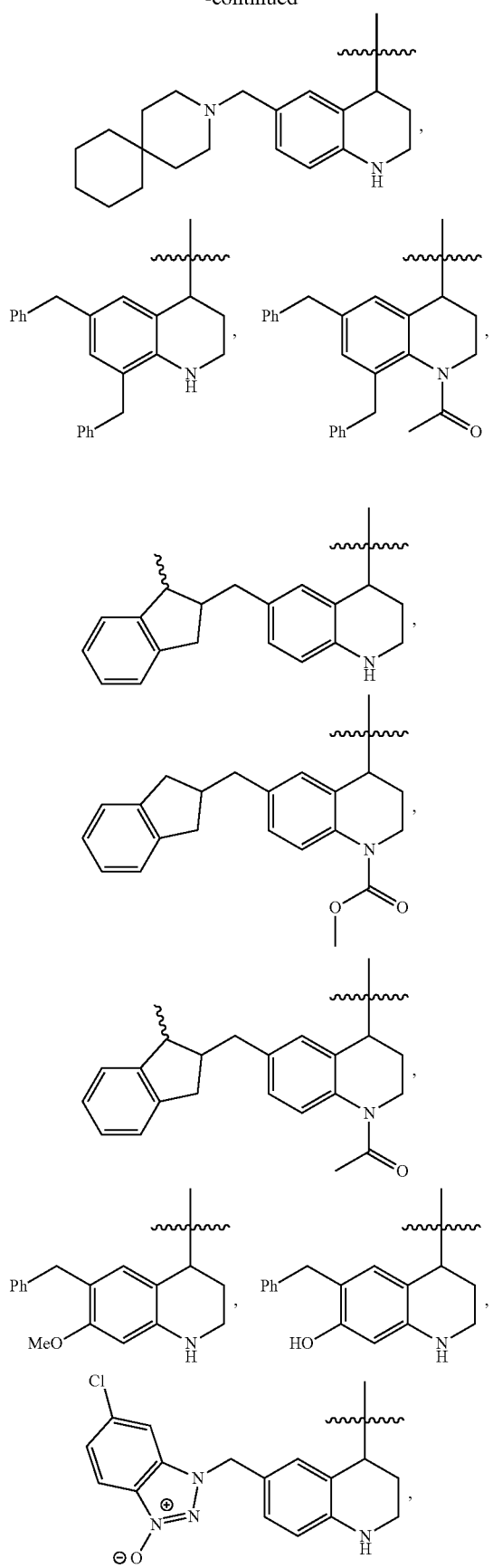
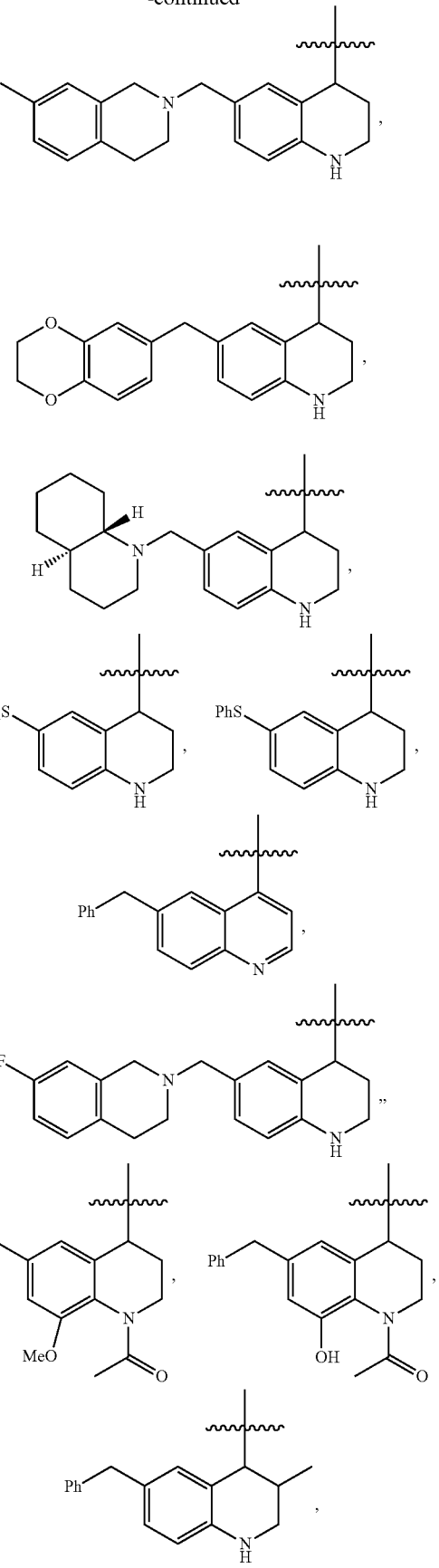

-continued
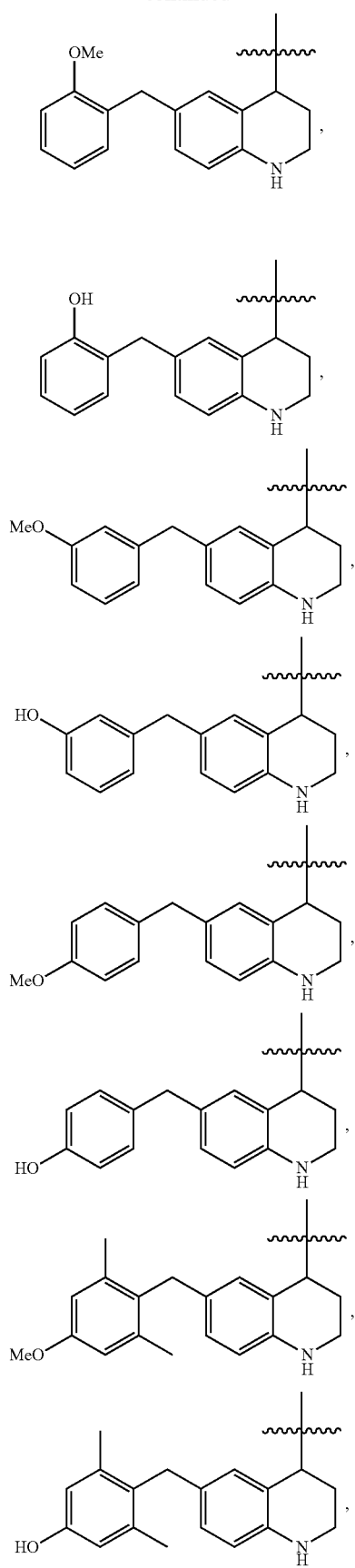
-continued
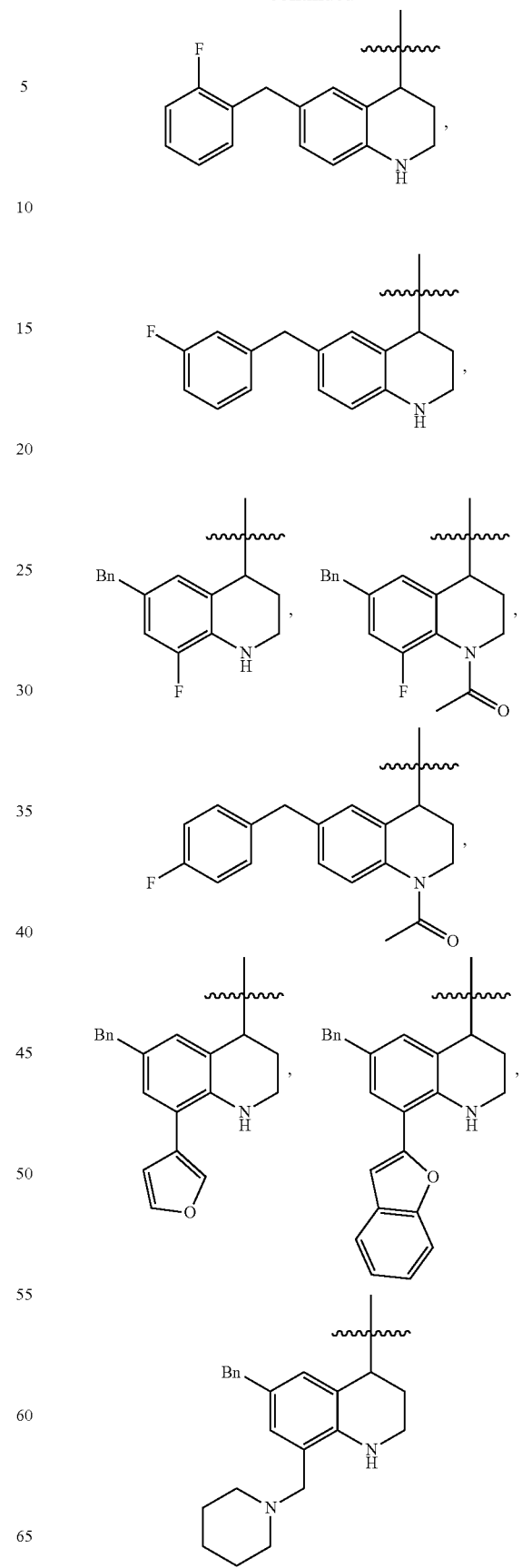

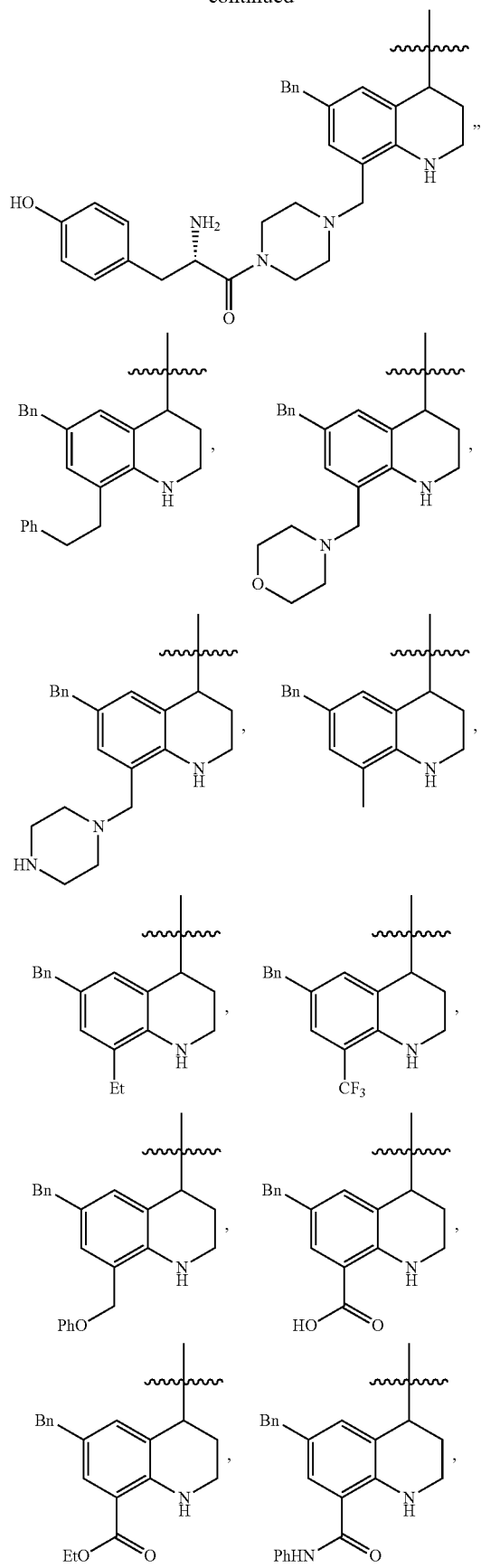
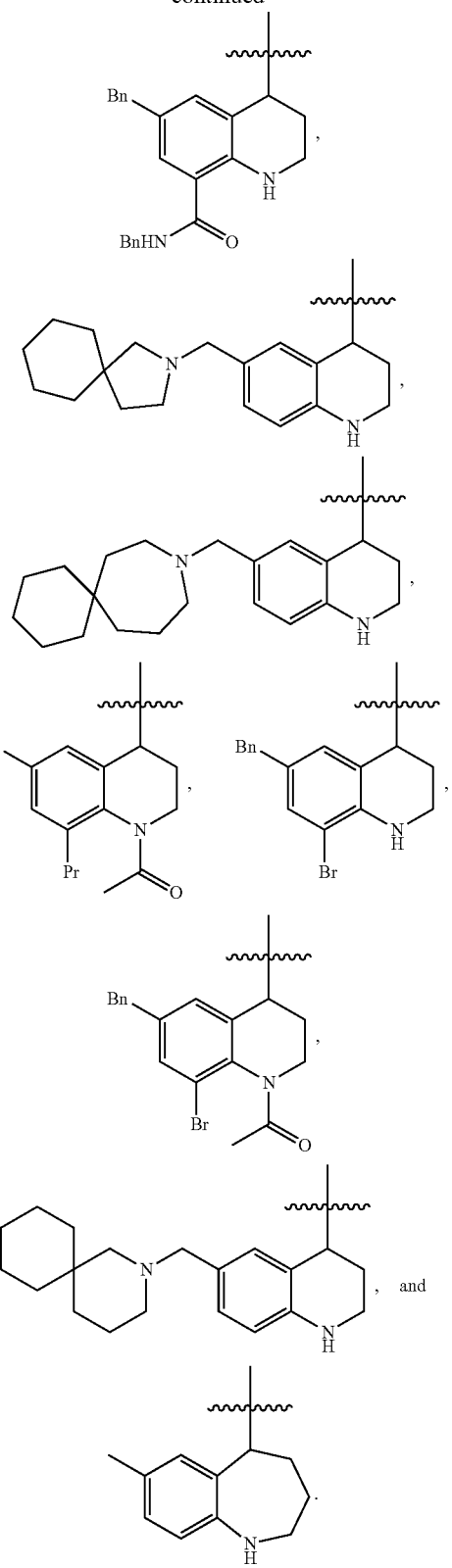
In various cases, A is formula (D). In some cases, at least one J is $CR^1$. In some cases, each J is $CR^1$. In some embodiments, at least one J is $NR^3$. In some cases, at least one J is $CR^1$ and at least one other J is $NR^3$. In various embodiments, m is 1. In some embodiments, m is 2. In various cases, n is 0. In various embodiments, n is 1. In some cases, n is 2.

For any embodiment when A is formula (B), (C), or (D), each $R^1$ independently is H, halo, $C_{1-6}$haloalkyl, or $C_{1-6}$alkyl. In some cases, each $R^1$ independently is H, F, Br, $CF_3$, methyl, ethyl, propyl, n-butyl, or t-butyl. In various cases, each $R^1$ independently is $C_{0-6}$alkylenearyl, $C_{0-6}$alkyleneheteroaryl, $C_{0-6}$alkylenecycloalkyl, or $C_{0-6}$alkyleneheterocycloalkyl. In some embodiments, each $R^1$ independently is aryl, $C_1$alkylenearyl, $C_2$alkylenearyl, heteroaryl, or $C_1$alkyleneheterocycloalkyl. In some cases, each $R^1$ independently is phenyl, benzyl, naphthyl,

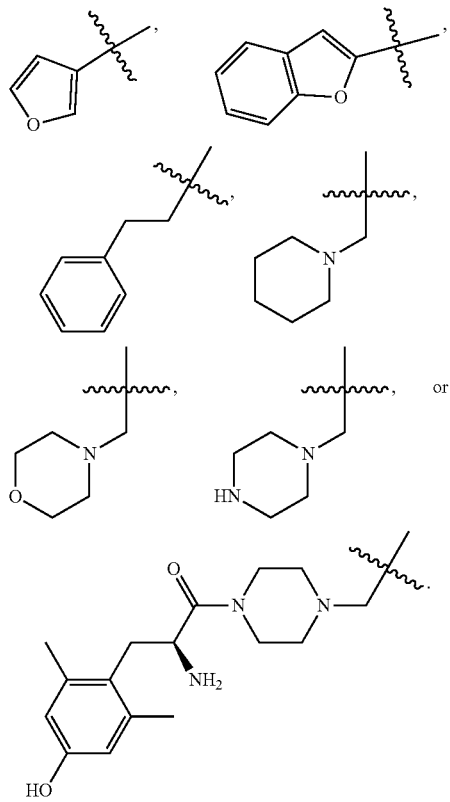

For example, A is selected from the group consisting of

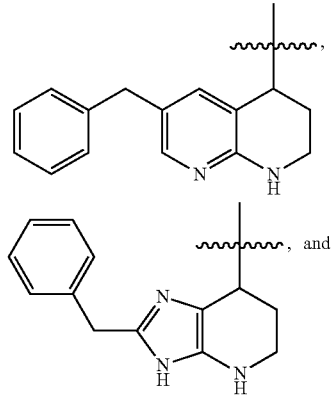

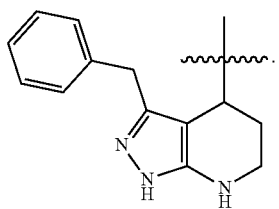

In various cases, each $R^1$ independently is $C_{0-3}$alkyleneOR$^4$, C(O)OR$^4$, or C(O)N(R$^4$)$_2$. In various embodiments, $R^4$ is H, methyl, ethyl, propyl, phenyl, or benzyl. In some cases, each $R^1$ independently is OH, OCH$_3$, OPh, COOH, CO$_2$Et, CH$_2$OPh, C(O)NHPh, or C(O)NHBn. In various cases, $R^3$ is H or $C_{1-6}$alkyl. In some cases, $R^3$ is H. In some embodiments, $R^3$ is methyl or propyl. In some cases, $R^3$ is $C_{0-3}$alkyleneC(O)R$^4$, or $C_{0-3}$alkyleneC(O)OR$^4$. In some embodiments, $R^4$ is H, $C_{1-6}$alkyl or $C_{0-3}$alkylenearyl. In various embodiments, $R^4$ is methyl, ethyl, propyl, phenyl, or benzyl. In various cases, $R^3$ is absent. In various embodiments, at least one $R^2$ is CH$_3$. In various cases, at least one $R^2$ is H. In some cases, each $R^2$ is H.

In various embodiments, $R^5$ is H, methyl, or cyclopropyl. In some cases, $R^5$ is H.

In various embodiments, each $R^6$ independently is H, CH$_3$, or Cl. In some cases, each $R^6$ is CH$_3$.

In various, cases, $R^7$ is H, OH, OCH$_3$, Cl, or C(O)NH$_2$. In some embodiments, $R^7$ is OH.

In another aspect, the disclosure provides compounds selected from the group consisting of:

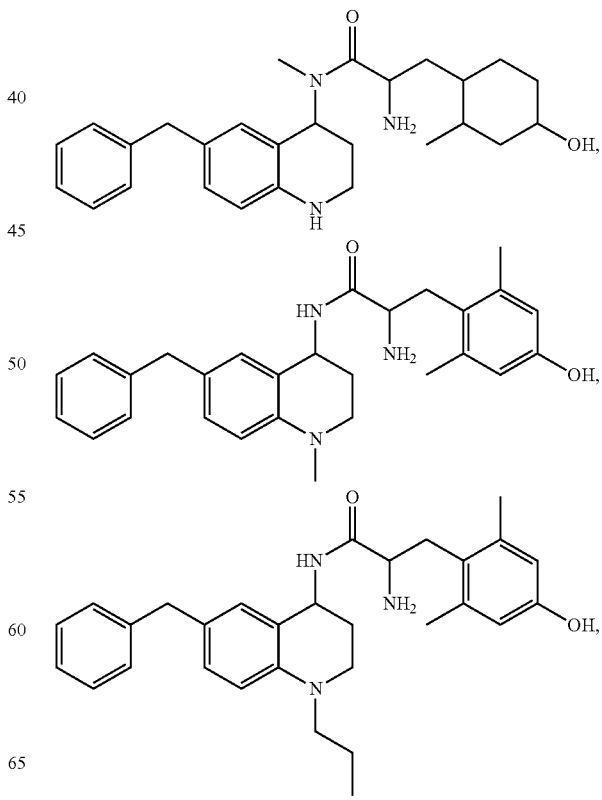

-continued
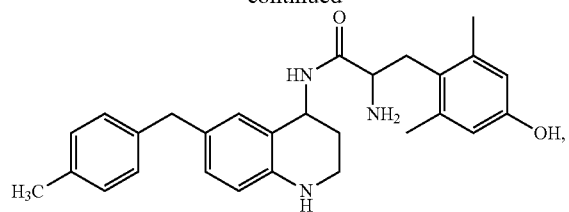
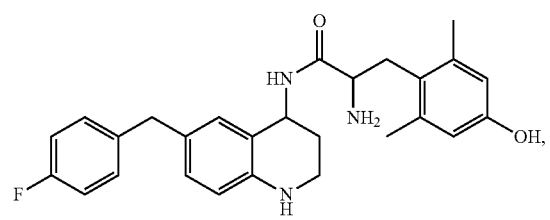
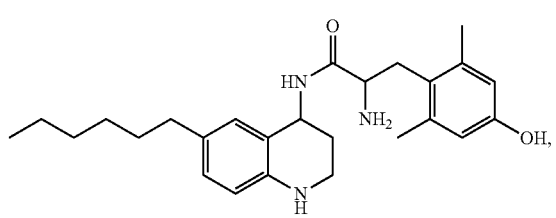
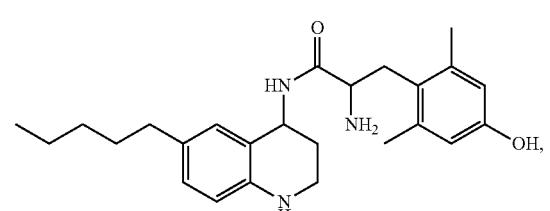
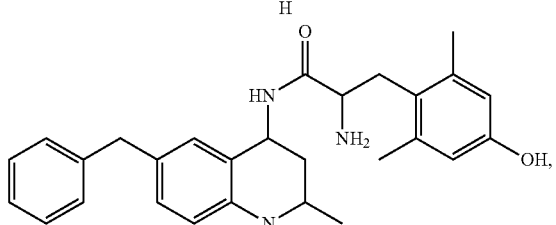
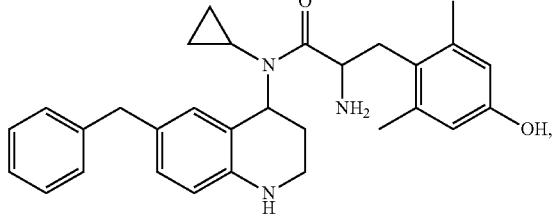
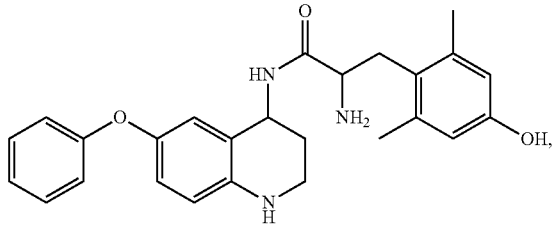
-continued
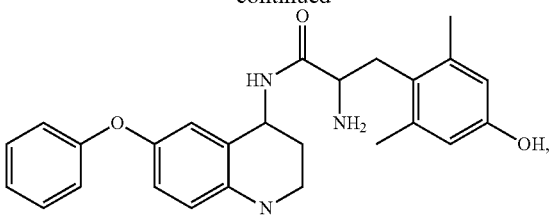
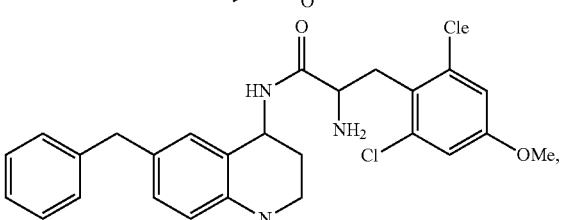
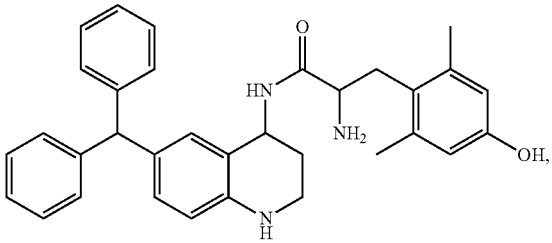
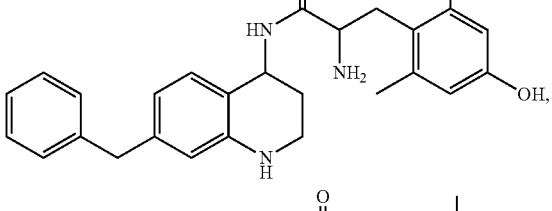
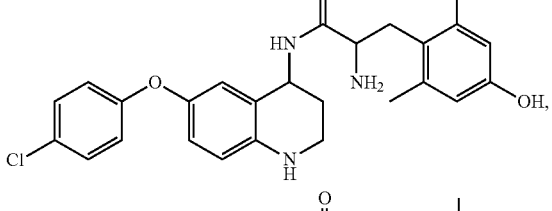
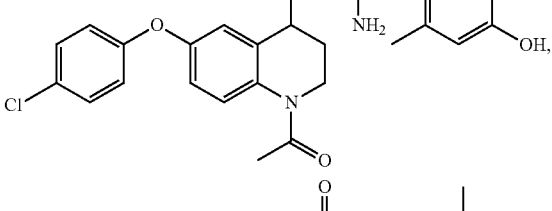
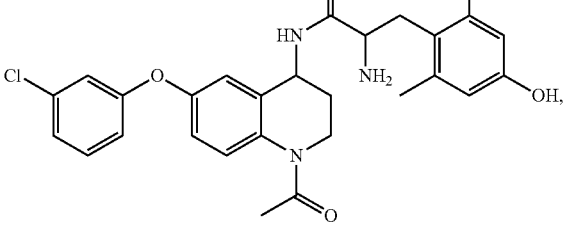

21
-continued
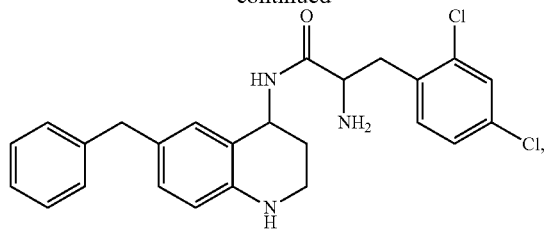
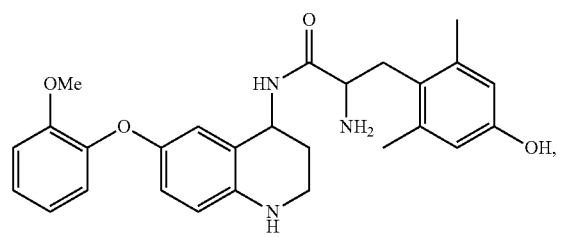
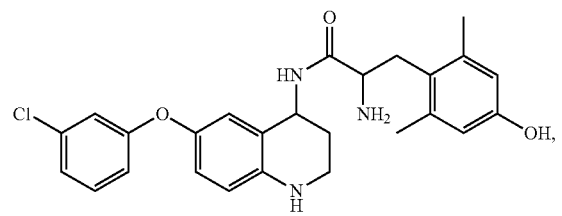
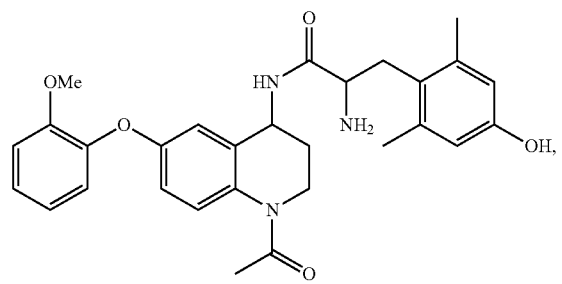
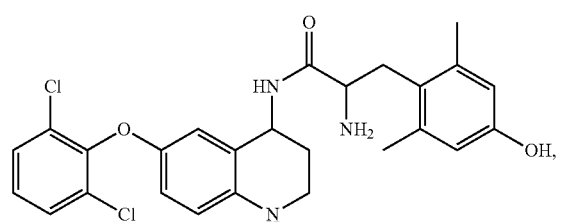
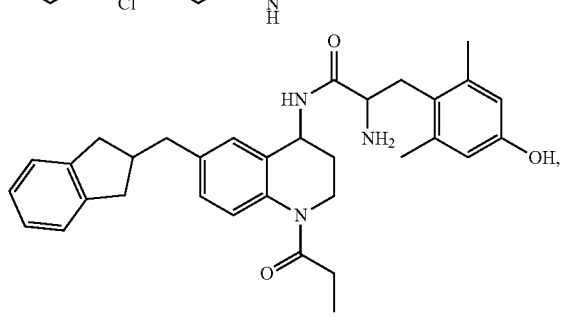
22
-continued
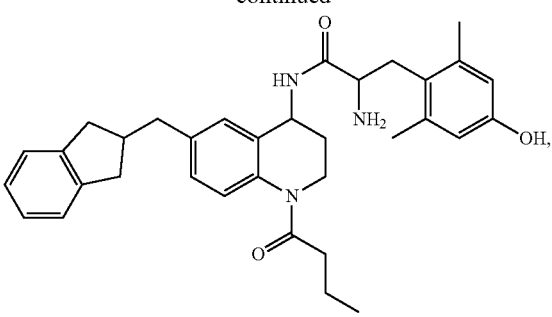
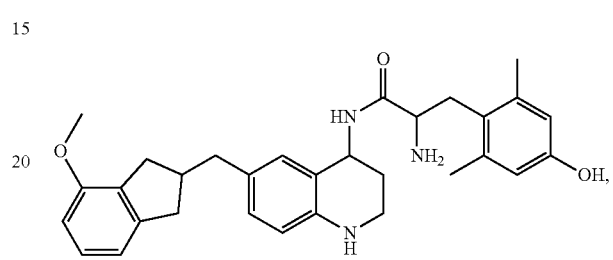
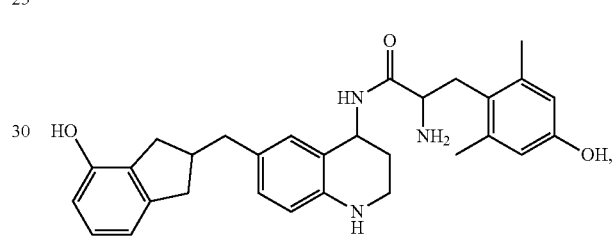
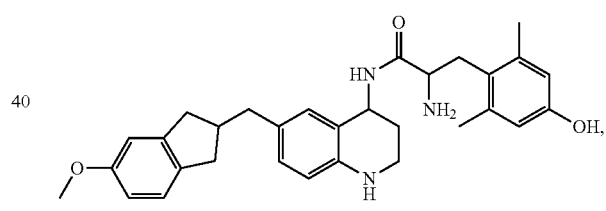
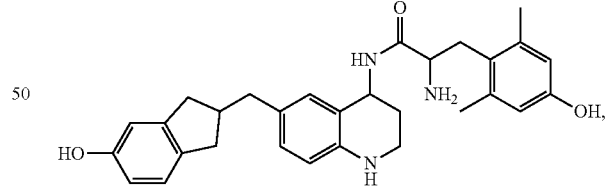
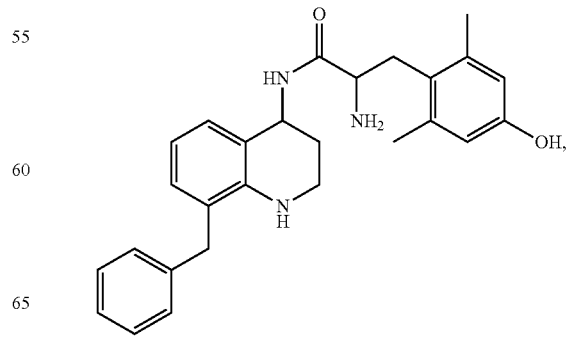

-continued
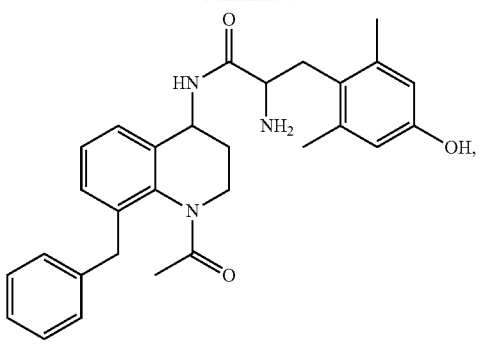
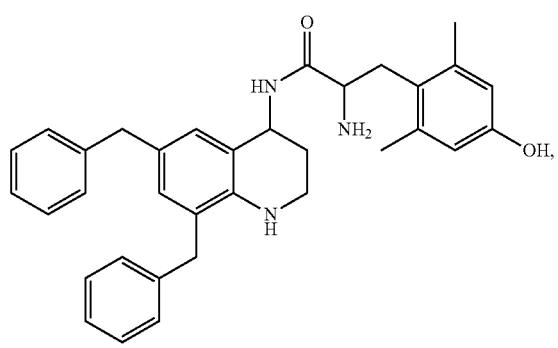
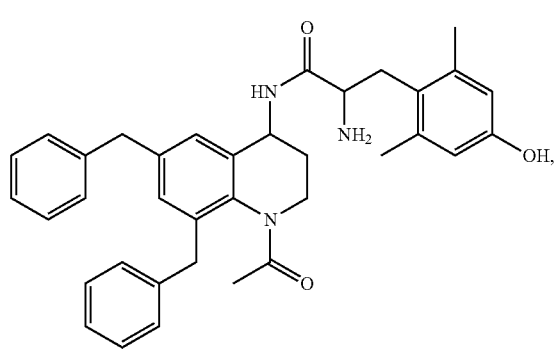
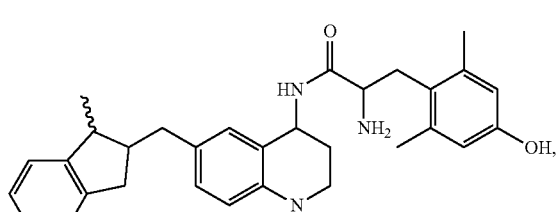
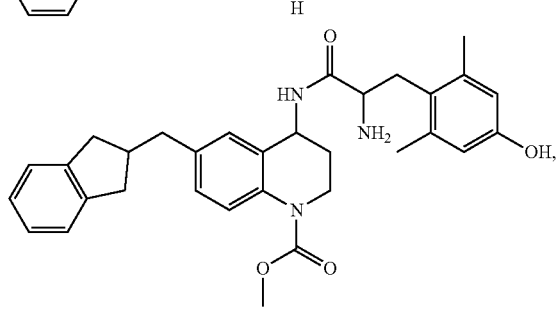
-continued
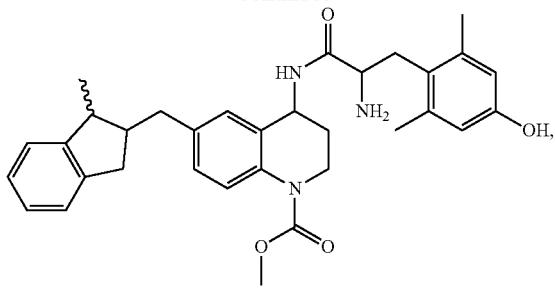
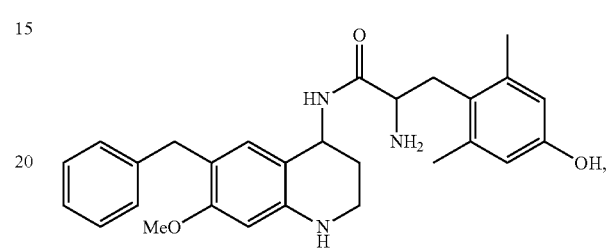
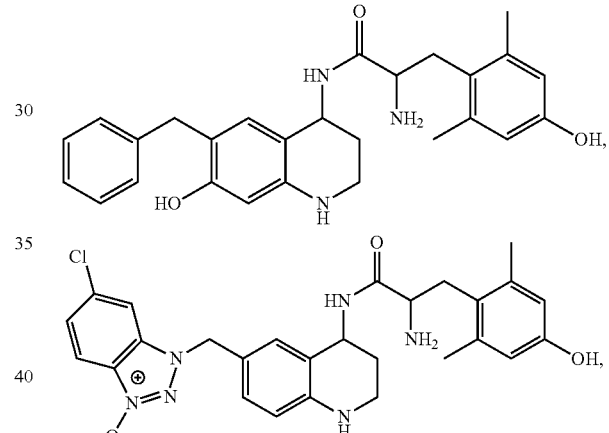
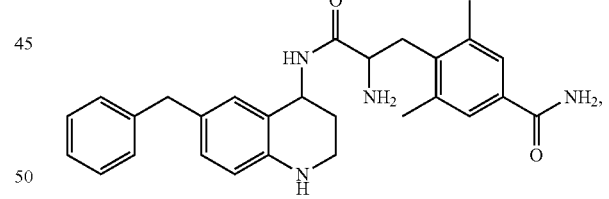
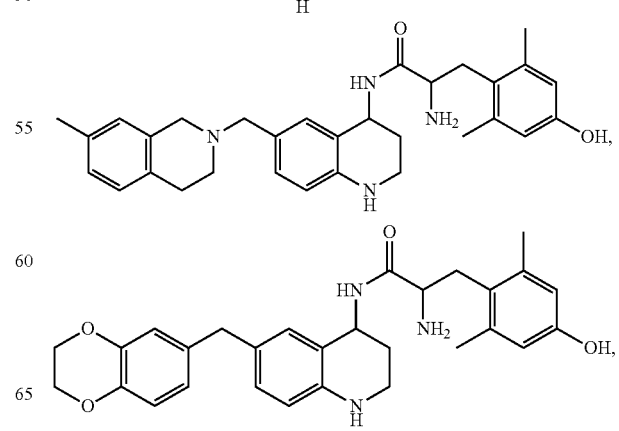

25
-continued
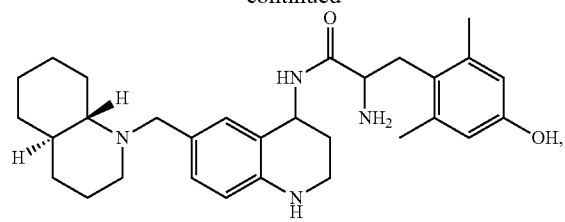
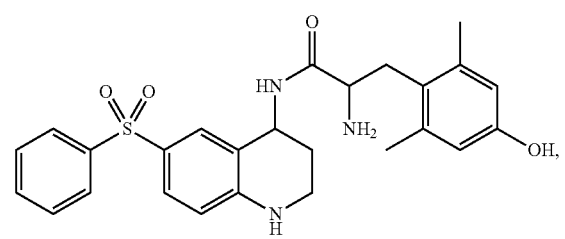
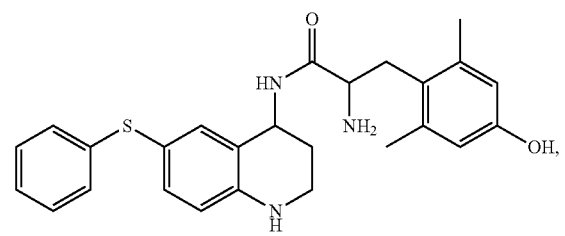
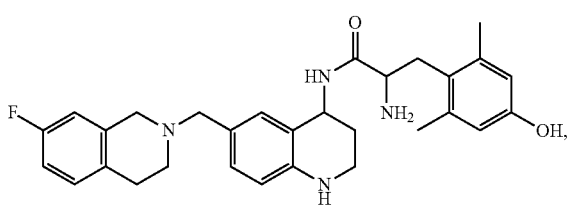
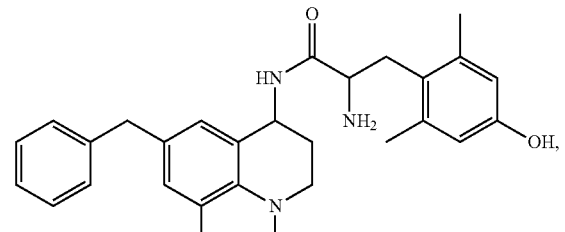
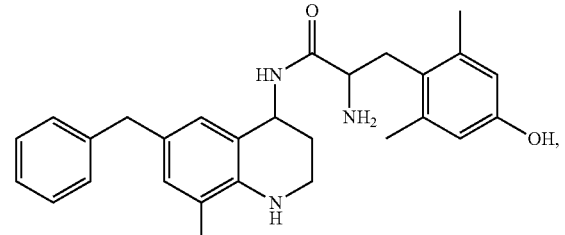
26
-continued
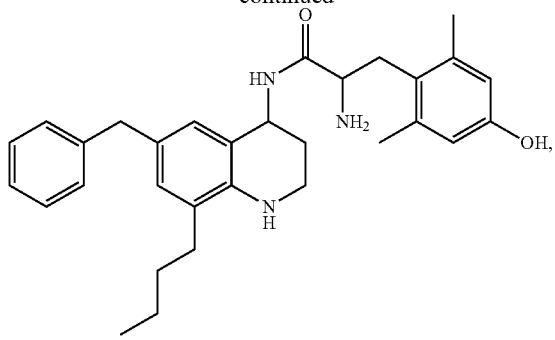
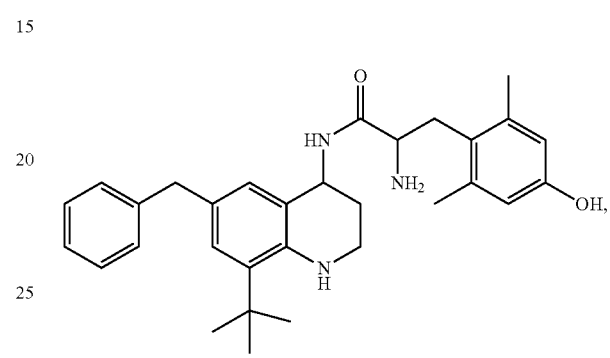
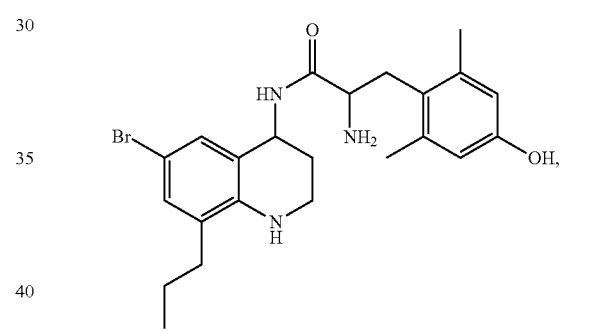
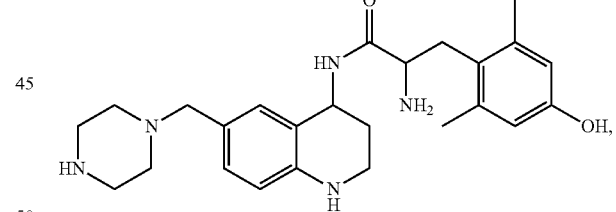
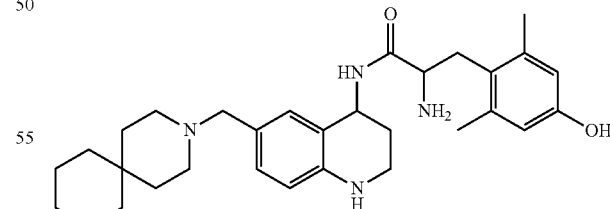
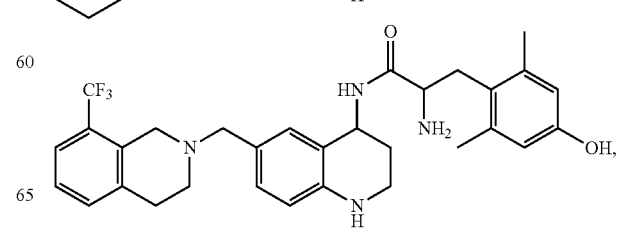

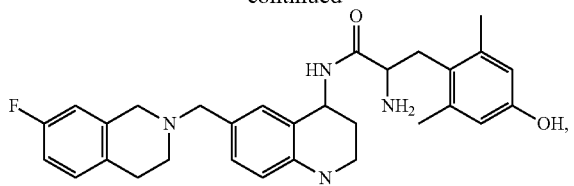
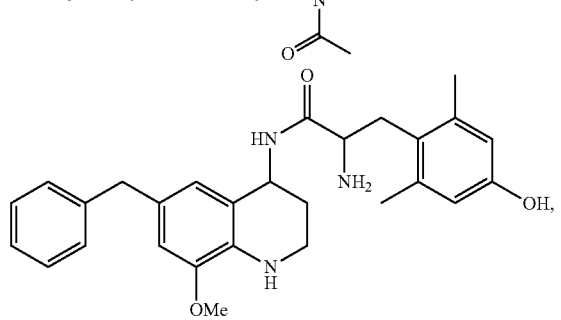
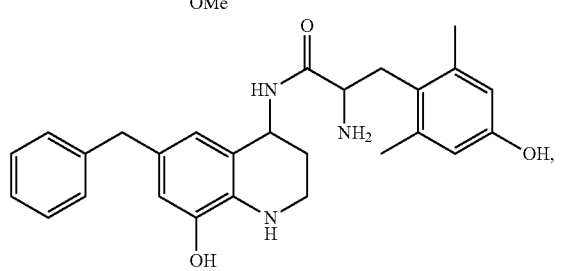
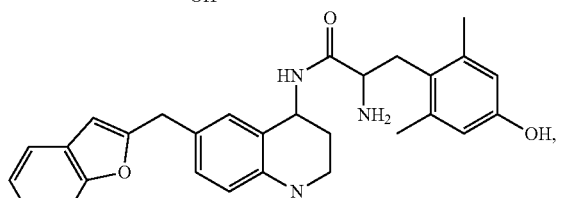
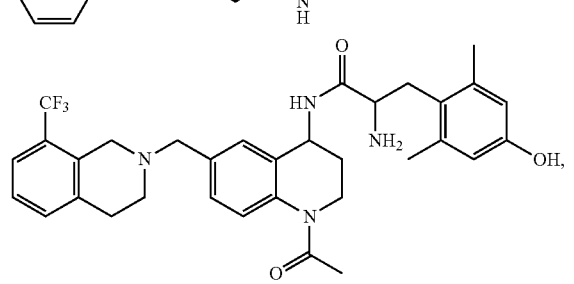
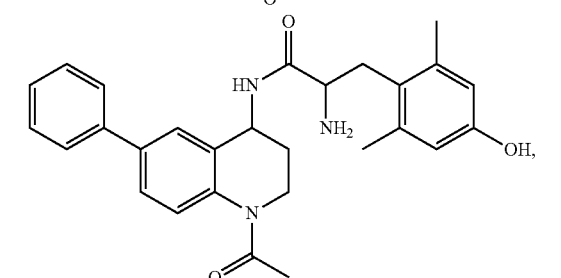
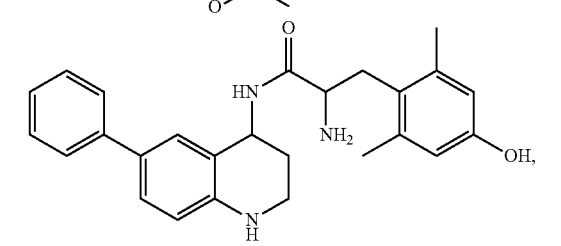
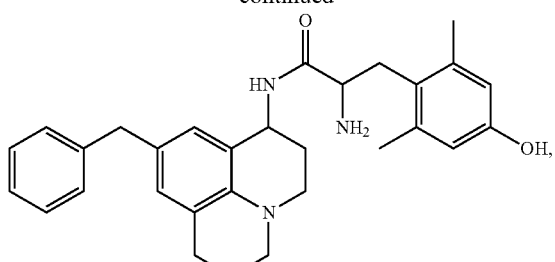
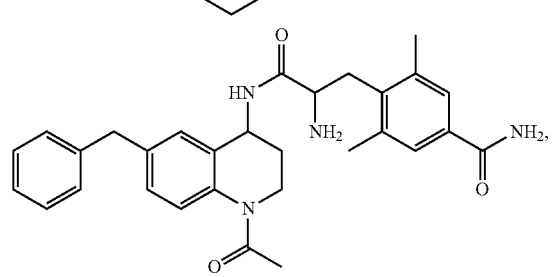
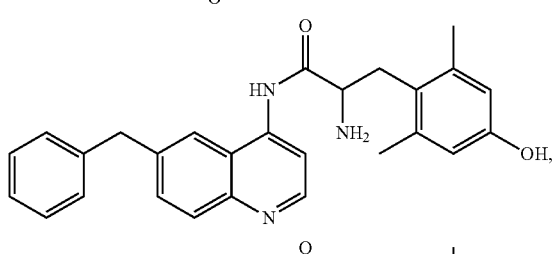
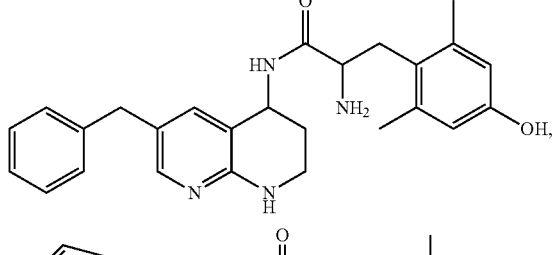
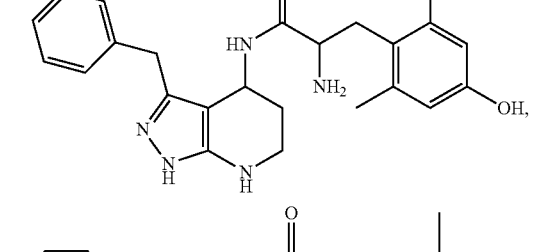
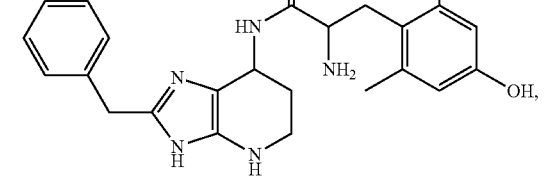
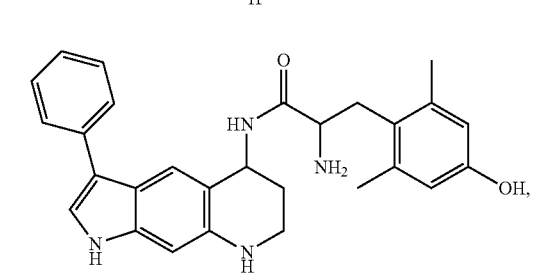

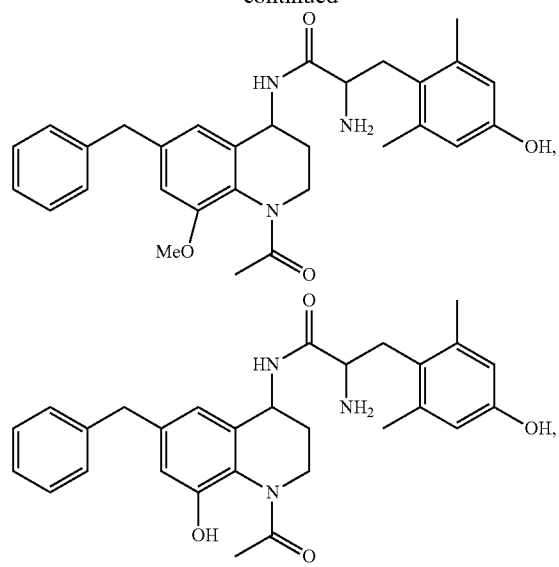
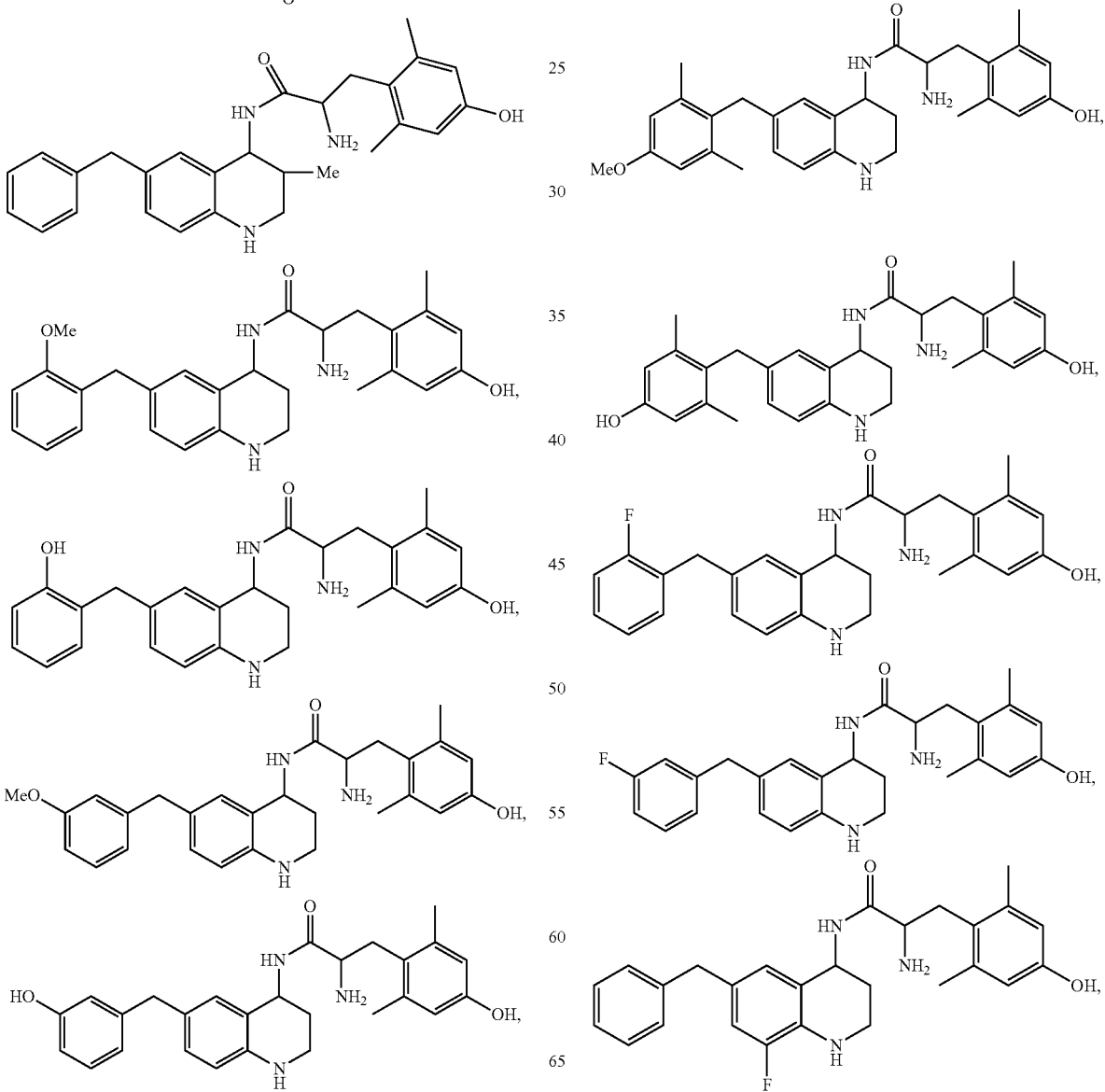

-continued
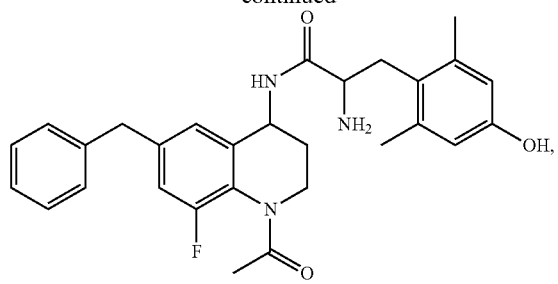
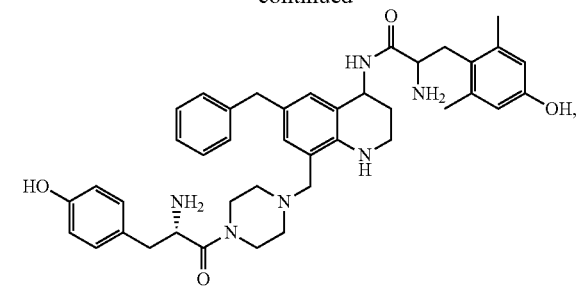
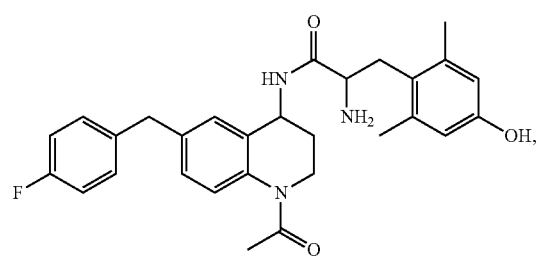
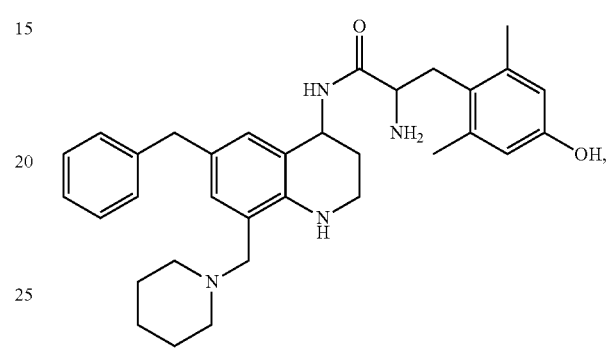
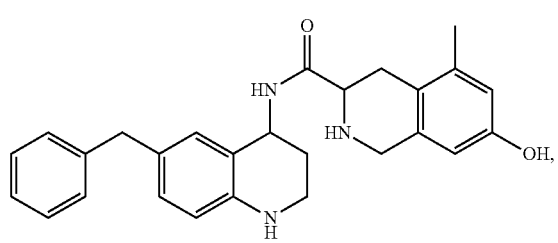
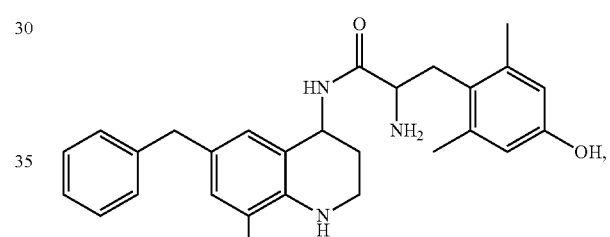
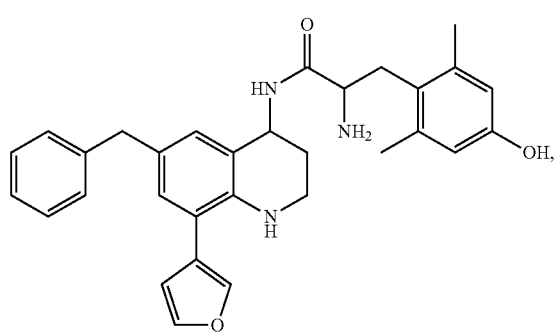
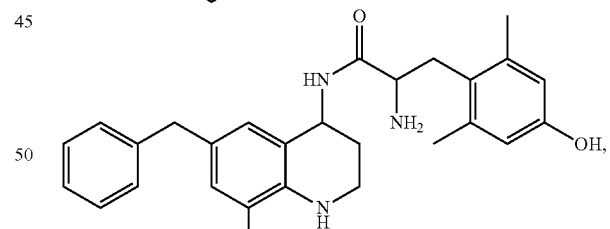
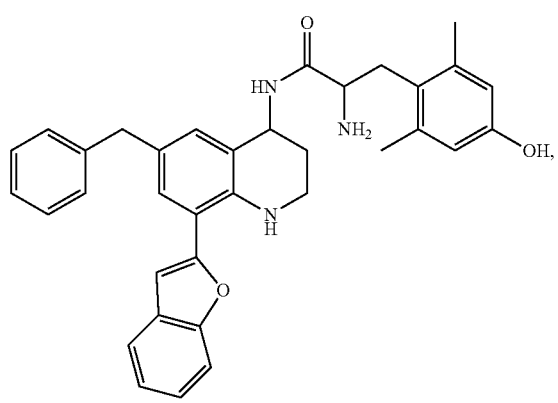
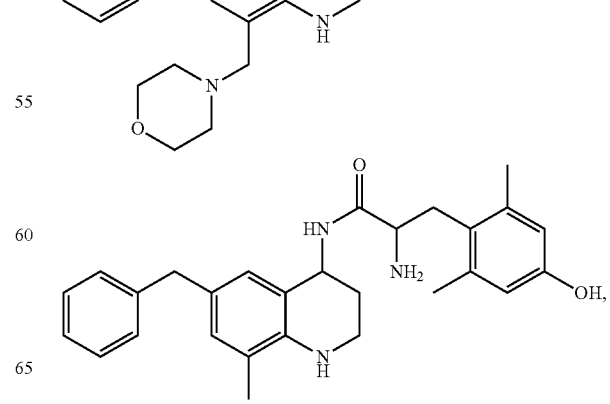

33
-continued
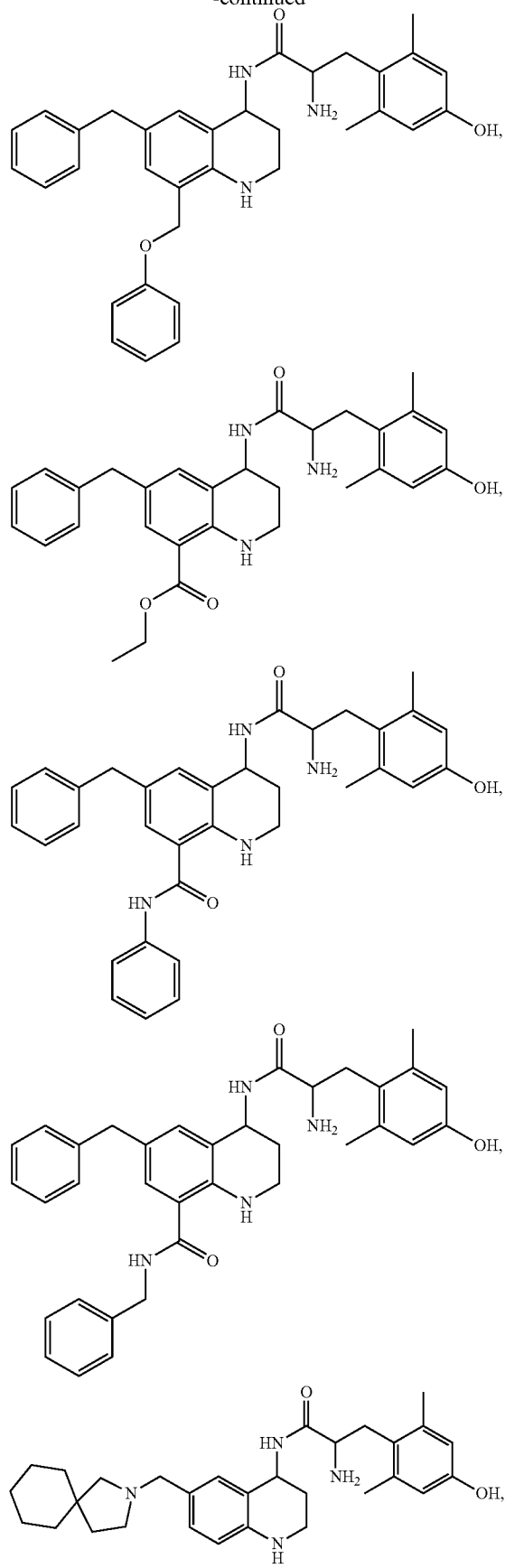
34
-continued
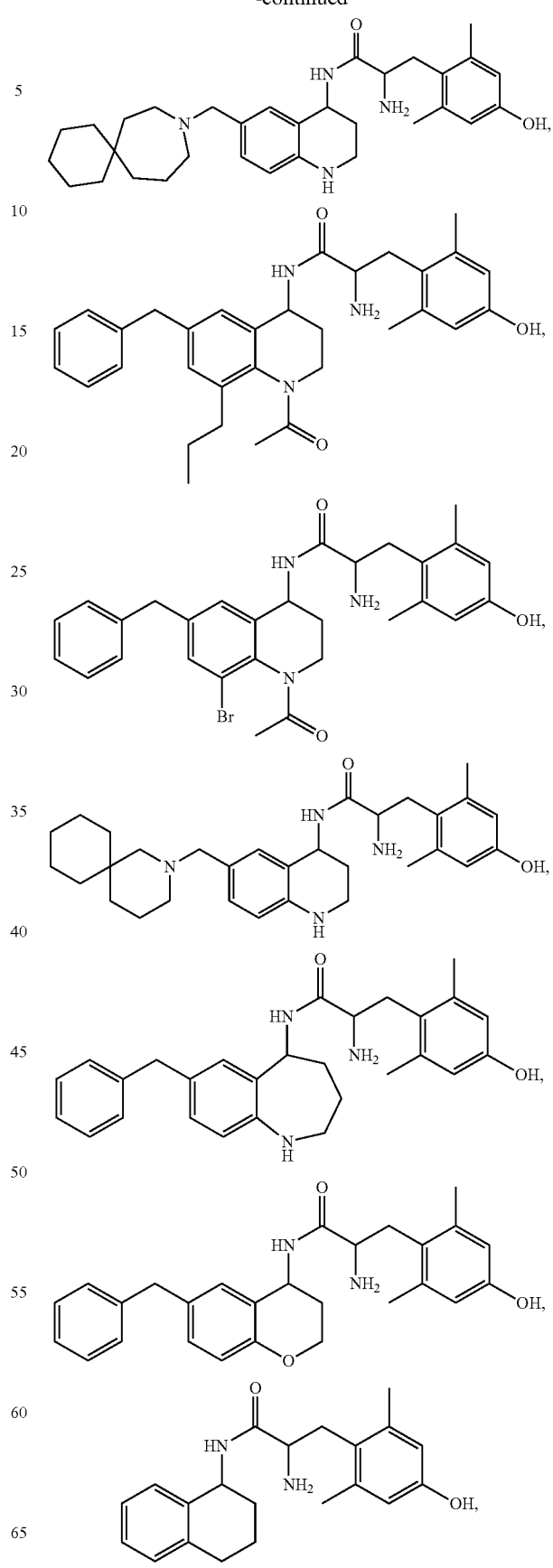

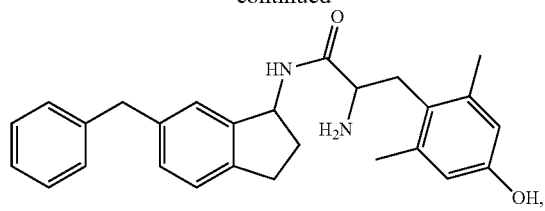
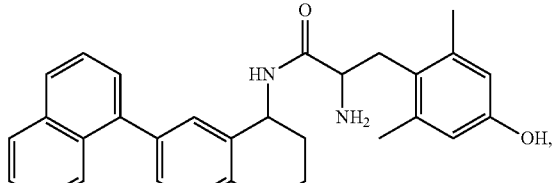
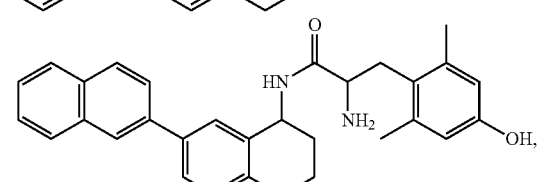
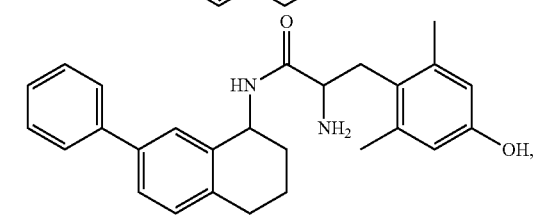
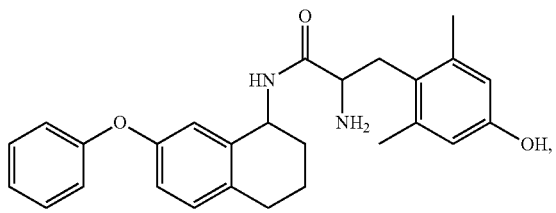
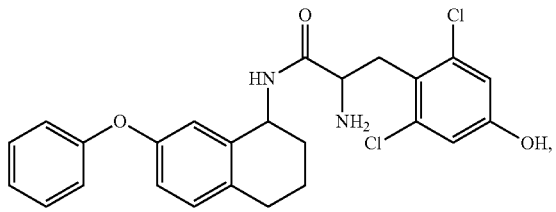
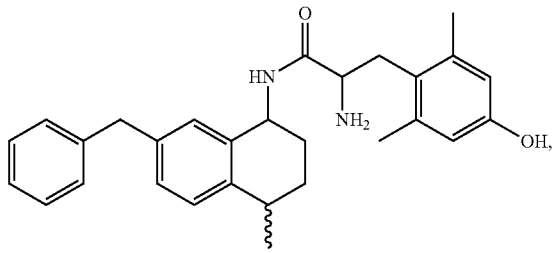
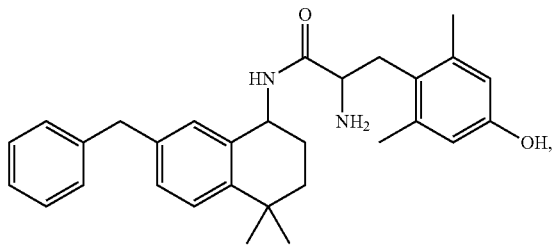
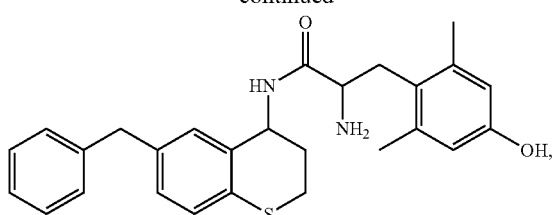
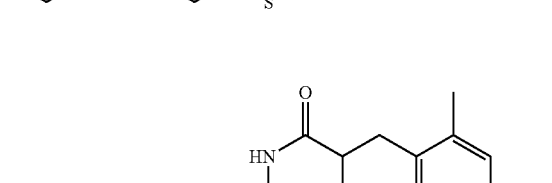
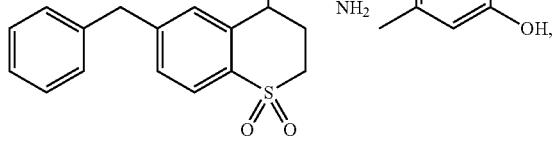
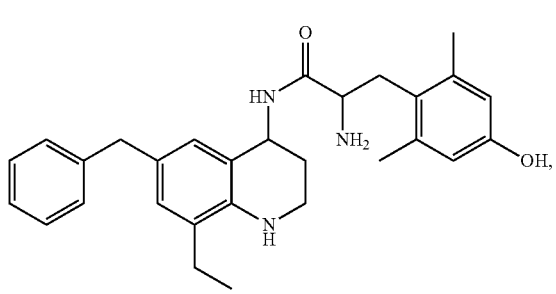
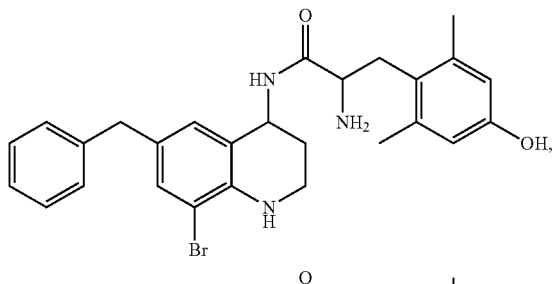
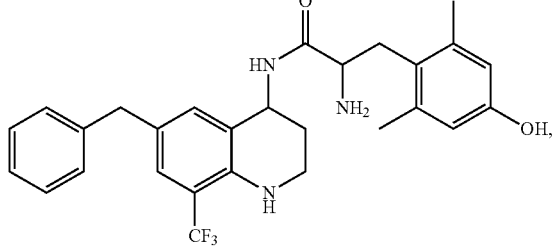
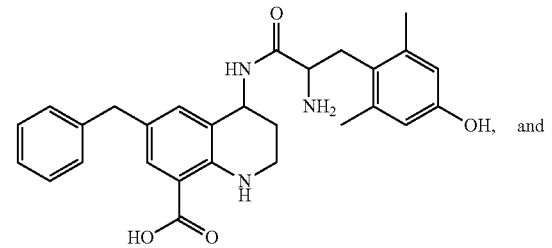
and -continued

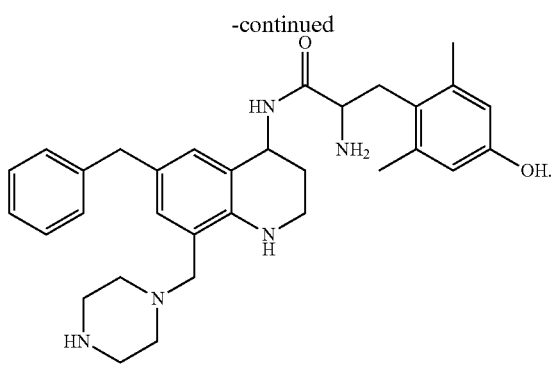

For example, the disclosure provides a compound is selected from the group consisting of compound 1001 to compound 1131.

Yet another aspect of the disclosure provides a pharmaceutical formulation that includes a compound as disclosed herein and a pharmaceutically acceptable excipient.

Still another aspect of the disclosure provides a method of modulating the MOR, the DOR, the KOR, or any combination thereof in a cell. In this method, the cell is contacted with a compound as disclosed herein, or a formulation as disclosed herein, in an amount effective to modulate MOR, DOR, KOR, or any combination thereof. In some cases, the MOR is modulated. In some embodiments, the DOR is modulated. In some cases, the KOR is modulated. In various cases, each of the MOR and KOR are modulated. In some cases, each of the MOR and DOR are modulated. In some embodiments, each of the MOR, DOR, and KOR are modulated. In some cases, the contacting occurs in vivo. In various embodiments, the contacting comprises administering to a subject in need thereof.

Another aspect of the disclosure provides a method of treating a subject suffering from pain. In this method, the subject is administered a therapeutically effective amount of a compound as disclosed herein or a pharmaceutical formulation as disclosed herein. In some embodiments, the pain is associated with a disease or condition selected from gastrointestinal motility disorders, seizures, depression, and cocaine abuse. In various cases, the gastrointestinal motility disorder is irritable bowel syndrome or constipation. In some cases, the subject is human.

Other aspects of the disclosure include a compound as disclosed herein for use in the preparation of a medicament for the treatment of pain, and the use of a compound as disclosed herein for the treatment of pain.

Further aspects and advantages will be apparent to those of ordinary skill in the art from a review of the following detailed description, taken in conjunction with the drawings.

DETAILED DESCRIPTION

Provided herein are peptidomimetic compounds that can act as mu-opioid receptor ("MOR") agonists, delta-opioid receptor ("DOR") antagonists, or as dual mu-opioid receptor agonist/delta-opioid receptor antagonist ("MOR agonist/ DOR antagonist") agents. These modulators can be used as analgesics to treat pain, and are advantageous for pain management over traditional opioids because they exhibit decreased or no side effects. These compounds can also act as kappa-opioid receptor ("KOR") modulators, either exclusively or simultaneously with MOR modulator activity. Such dual modulators can be used to treat cocaine or opioid abuse. The compound disclosed herein also can act as DOR/KOR dual modulators and MOR/DOR/KOR triplet modulators.

There is a growing body of evidence to suggest that the DOR plays a significant role in the modulation of the side effects related to the chronic use of opioid analgesics. Although the analgesic effects of traditional opioid agents such as morphine are associated with stimulation of the MOR, the coadministration of DOR antagonists has been shown to maintain the desired antinociceptive activity but with a reduced side-effect profile compared with a MOR agonist alone (Hepburn, M. J. et al. J. Pharm. Exp. Ther. 1997, 281:1350-1356; Abdelhamid, E. E. et al. J. Pharm. Exp. Ther. 1991, 258:299-303; Kest, B. et al. Brain Res. Bull. 1996, 39:185-188; Zhu, Y. et al. Neuron 1999, 24:243-252). Because the compounds disclosed herein target both the MOR and DOR, they advantageously provide pain relief without the side effects associated with traditional opioids. Additionally, such compounds with reduced affinity and efficacy at the KOR can treat pain while limiting hallucinogenic, dissociative, and/or stress-related side effects. Dual MOR/KOR modulators can be used to treat cocaine abuse and as antidotes for opioid overdose.

The compounds described herein have a structure of Formula (I):

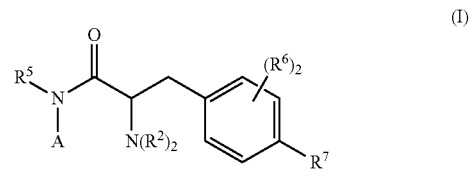

(I)

wherein the substituents are as described in detail below.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

The term "alkylene" used herein refers to an alkyl group having a substituent. For example, the term "alkylenearyl" refers to an alkyl group substituted with an aryl group. For example, an alkylene group can be —$CH_2CH_2$— or —$CH_2$—. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups. The terms "alkyloxy" and "alkylenearyloxy" refer to an alkyl group or alkylenearyl group substituted with an oxygen, respectively. Unless otherwise indicated, an alkylene group can be an unsubstituted alkylene group or a substituted alkylene group.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (e.g., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to eight carbon atoms.

As used herein, the term "heterocycloalkyl" is defined similarly as cycloalkyl, except the ring contains one to three heteroatoms independently selected from oxygen, nitrogen, and sulfur. In particular, the term "heterocycloalkyl" refers to a ring containing a total of three to eight atoms, of which 1, 2, 3 or three of those atoms are heteroatoms independently selected from the group consisting of oxygen, nitrogen, and sulfur, and the remaining atoms in the ring are carbon atoms. Nonlimiting examples of heterocycloalkyl groups include piperdine, pyrazolidine, tetrahydrofuran, tetrahydropyran, dihydrofuran, morpholine, and the like. Cycloalkyl and heterocycloalkyl groups can be saturated or partially unsaturated ring systems optionally substituted with, for example, one to three groups, independently selected alkyl, alkyleneOH, C(O)NH$_2$, NH$_2$, oxo (═O), aryl, haloalkyl, halo, and OH. Heterocycloalkyl groups optionally can be further N-substituted with alkyl, hydroxyalkyl, alkylenearyl, and alkyleneheteroaryl. The heterocycloalkyl groups described herein can be isolated or fused to another heterocycloalkyl group, a cycloalkyl group, an aryl group, and/or a heteroaryl group. When a heterocycloalkyl group is fused to another heterocycloalkyl group, then each of the heterocycloalkyl groups can contain three to eight total ring atoms, and one to three heteroatoms.

As used herein, the term "aryl" refers to a monocyclic aromatic group, such as phenyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like. Throughout, the abbreviation "Ph" refers to phenyl and "Bn" refers to benzyl (i.e., CH$_2$phenyl).

As used herein, the term "heteroaryl" refers to a monocyclic aromatic ring having five or six total ring atoms, and containing one to three heteroatoms selected from nitrogen, oxygen, and sulfur atom in the aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, ON, NC, OH, alkoxy, amino, CO$_2$H, CO$_2$alkyl, aryl, and heteroaryl. In some cases, the heteroaryl group is substituted with one or more of alkyl and alkoxy groups. Heteroaryl groups can be isolated (e.g., pyridyl) or fused to another heteroaryl group (e.g., purinyl), a cycloalkyl group (e.g., tetrahydroquinolinyl), a heterocycloalkyl group (e.g., dihydronaphthyridinyl), and/or an aryl group (e.g., benzothiazolyl and quinolyl). Examples of heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. When a heteroaryl group is fused to another heteroaryl group, then each heteroaryl group can contain five or six total atoms and one to three heteroatoms in its aromatic ring.

As used herein, the term "alkoxy" or "alkoxyl" as used herein refers to a "—O-alkyl" group. The alkoxy or alkoxyl group can be unsubstituted or substituted.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, ether, polyether, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds (e.g., an opioid receptor modulator or combination of opioid receptor modulators) that ameliorates, attenuates or eliminates one or more symptoms of a particular disease or condition (e.g., heart disease), or prevents or delays the onset of one of more symptoms of a particular disease or condition.

As used herein, the terms "patient" and "subject" may be used interchangeably and mean animals, such as dogs, cats, cows, horses, and sheep (e.g., non-human animals) and humans. Particular patients or subjects are mammals (e.g., humans). The terms patient and subject includes males and females.

As used herein, the term "pharmaceutically acceptable" means that the referenced substance, such as a compound of the present disclosure, or a formulation containing the compound, or a particular excipient, are safe and suitable for administration to a patient or subject. The term "pharmaceutically acceptable excipient" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

Compounds of Formula (I)

Provided herein are compounds of Formula (I), or pharmaceutically acceptable salts thereof:

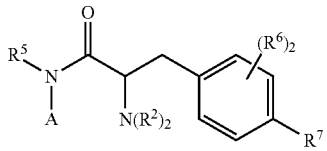

(I)

wherein:
A is a formula selected from the group consisting of:

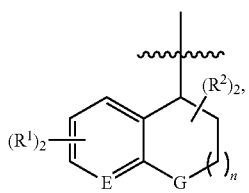

(B)

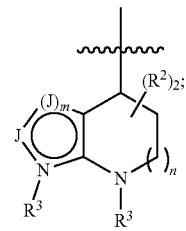

(C)

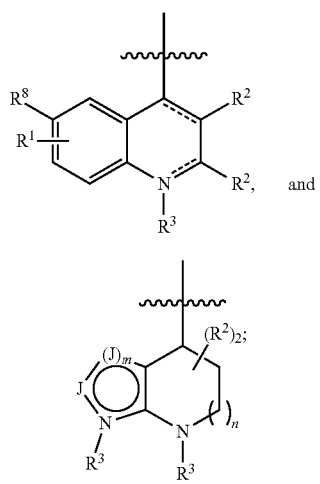

(D)

E is CR¹ or N;
G is C(R²)₂, O, S, or SO₂;
each J independently is CR¹ or NR³;
m is 1 or 2;
n is 0, 1, or 2;
---- indicates an optional double bond;
each R¹ independently is H, halo, $C_{1-6}$alkyl, $C_{1-6}$haloalkyl, $C_{0-6}$alkylenearyl, $C_{0-6}$alkyleneheteroaryl, $C_{0-6}$alkylenecycloalkyl, $C_{1-6}$alkyleneheterocycloalkyl, $C_{0-3}$alkyleneOR⁴, SR⁴, SO₂R⁴, C(O)N(R⁴)₂, C(O)OR⁴, or C(O)SR⁴; and wherein for formula (B), at least one R¹ is other than H;
each R² independently is H or $C_{1-6}$alkyl;
R³ is H, $C_{1-6}$alkyl, $C_{0-3}$alkyleneC(O)R⁴, $C_{0-3}$alkyleneC(O)OR⁴, $C_{0-3}$alkyleneC(O)NHR⁴, or absent;
when A is formula (C), R³ and R¹ can connect to form a 5-7-membered ring;
R⁴ is H, $C_{1-6}$alkyl, $C_{0-3}$alkylene-$C_{3-6}$cycloalkyl, $C_{1-3}$alkylene-OC$_{1-3}$alkyl, or $C_{0-3}$alkylenearyl; R⁵ is H, $C_{1-3}$ alkyl, or $C_{3-6}$cycloalkyl;
each R⁶ independently is H, $C_{1-3}$alkyl, OH, $C_{1-3}$alkoxy, halo, or C(O)N(R³)₂, and at least one R⁶ is not H;
R⁷ is H, $C_{1-3}$alkyl, OH, $C_{1-3}$alkoxy, halo, or C(O)N(R³)₂; and
R⁸ is H, halo, $C_{1-6}$alkyl, $C_{0-6}$alkylenearyl, $C_{1-6}$alkyleneheteroaryl, $C_{1-6}$alkylenecycloalkyl, $C_{1-6}$alkyleneheterocycloalkyl, O-aryl, S-aryl, or SO₂-aryl;

with the proviso that (a) when A is

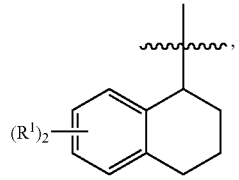

then R¹ is not CH₂naphthyl, CH₂phenyl, or CH₂cyclohexyl; and (b) when (i) A is formula (C), (ii) each ---- indicates a single bond, (iii) R³ is H or $C_{0-3}$alkyleneC(O)R₄, (iv) R⁵ is H, R⁷ is H or OH, and (v) R⁸ is unsubstituted CH₂aryl, unsubstituted CH₂CH₂aryl, unsubstituted CH₂heteroaryl, unsubstituted CH₂cycloalkyl, or unsubstituted CH₂heterocycloalkyl, then at least one of R¹ and R² is other than H.

In some cases, A is

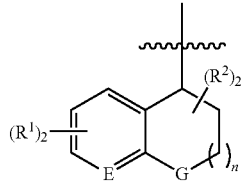

(B)

and at least one R¹ is other than H. In some cases, E is N. In some cases, E is CR¹. R¹ can be unsubstituted or substituted. In some of these cases, at least one R¹ is substituted. Examples of substituents for R¹ include $C_{1-4}$alkyl (e.g., methyl, ethyl, propyl, or butyl), hydroxyl, $C_{1-4}$alkoxy (e.g., methoxy, ethoxy, propoxy, or butoxy), halo (e.g., F, Cl, Br, or I), aryl (e.g., phenyl), haloalkyl (e.g., CF₃), cyano, nitro, and amino.

In some embodiments, E is CR¹ and R¹ is halo (e.g., F, Cl, Br, or I). For example, E can be CF, CCl, CBr, or CI. In various embodiments, E is CR¹ and R¹ is $C_{1-6}$alkyl or $C_{1-3}$ alkyl, such as methyl, ethyl, propyl, butyl (e.g., sec-butyl, isobutyl, or tert-butyl), pentyl, or hexyl. For example, E can be CMe, CEt, or C$^t$Bu. In various cases, E is CR¹ and R¹ is $C_{0-6}$alkylenearyl or $C_{0-2}$alkylenearyl (e.g., aryl, $C_1$alkylenearyl, $C_2$alkylenearyl, $C_2$alkylenearyl, $C_3$alkylenearyl, $C_4$alkylenearyl, $C_5$alkylenearyl, or $C_6$alkylenearyl). Aryl can include a monocyclic or polycyclic aromatic group. Nonlimiting examples of the aryl group include phenyl, naphthyl, tetrahydronaphthyl, anthryl, phenanthryl, indenyl, indanyl, fluorenyl, and azulenyl. In some embodiments, the aryl group can be phenyl, naphthyl, chlorophenyl, fluorophenyl, hydroxyphenyl, methylphenyl, methoxyphenyl, trifluoromethylphenyl, nitrophenyl, 2,4-methoxychlorophenyl, or 4-hydroxy-2,6-dimethylphenyl (e.g., E can be C-phenyl, C-naphthyl, C-chlorophenyl, C-fluorophenyl, C-hydroxyphenyl, C-methylphenyl, C-methoxyphenyl, C-trifluoromethylphenyl, C-nitrophenyl, C-2,4-methoxychlorophenyl, or C-4-hydroxy-2,6-dimethylphenyl). In some cases, E can be C-phenyl, C-benzyl, C-phenethyl, C-naphthyl, C—CH₂naphthyl, or C—CH(phenyl)₂. For example, E can be C—CH₂Ph or C—CH₂CH₂Ph.

In some cases, E is CR¹ and R¹ is $C_{0-6}$alkyleneheteroaryl, $C_{0-3}$alkyleneheteroaryl or $C_{4-6}$alkyleneheteroaryl (e.g., heteroaryl, $C_1$alkyleneheteroaryl, $C_2$alkyleneheteroaryl, $C_3$alkyleneheteroaryl, $C_4$alkyleneheteroaryl, $C_5$alkyleneheteroaryl, or $C_6$alkyleneheteroaryl). Heteroaryl can be a monocyclic or polycyclic (e.g., fused bicyclic and fused tricyclic) aromatic ring system containing one to three nitrogen, oxygen, or sulfur atoms. Nonlimiting examples of the heteroaryl group include thienyl, furanyl, benzofuranyl, pyridyl, pyrrolyl, pyrazolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, pyridazinyl, thiazolyl, and thiadiazolyl. In some cases, the heteroaryl group is selected from the group consisting of furanyl, benzofuranyl, pyridyl, triazolyl, quinolyl, or isoquinolyl. For example, the heteroaryl group can include furanyl, benzofuranyl, or quinolinyl (e.g., E can be C-furanyl, C-benzofuranyl, or C-quinolinyl). In some cases, E is C-furanyl.

In some cases, E is $CR^1$ and $R^1$ is $C_{0-6}$alkylenecycloalkyl, or $C_{0-2}$alkylenecycloalkyl, or $C_{3-6}$alkylenecycloalkyl (e.g., cycloalkyl, $C_1$alkylenecycloalkyl, $C_2$alkylenecycloalkyl, $C_3$alkylenecycloalkyl, $C_4$alkylenecycloalkyl, $C_5$alkylenecycloalkyl or $C_6$alkylenecyloalkyl). Nonlimiting examples of the cycloalkyl group include cyclopropyl, cyclobutyl, cyclopentyl, and cyclohexyl. For example, the cycloalkyl group can be cyclopentyl or cyclohexyl. In some embodiments, E can be C—$CH_2$cyclopentyl, C—$CH_2$cyclohexyl, C—$CH_2CH_2$cyclopentyl, or C—$CH_2CH_2$cyclohexyl. For example, E can be C—$CH_2$cyclohexyl or C—$CH_2$cyclopentyl.

In some cases, E is $CR^1$ and $R^1$ is $C_{0-6}$alkyleneheterocycloalkyl or $C_{0-3}$alkyleneheterocycloalkyl or $C_{4-6}$alkyleneheterocycloalkyl (e.g., heterocycloalkyl, $C_1$alkyleneheterocycloalkyl, $C_2$alkyleneheterocycloalkyl, $C_3$alkyleneheterocycloalkyl, $C_4$alkyleneheterocycloalkyl, $C_5$alkyleneheterocycloalkyl, or $C_6$alkyleneheterocycloalkyl). Nonlimiting examples of the heterocycloalkyl group include piperidinyl, piperazinyl, azepinyl, pyrrolidinyl, dithianyl, morpholino, or dioxanyl. In some embodiments, the heterocycloalkyl group is selected from the group consisting of piperidinyl, piperazinyl, morpholino, and pyrrolidinyl. For example, E can be C—$CH_2$piperidinyl, C—$CH_2$piperazinyl, C—$CH_2$pyrrolidinyl, or C—$CH_2$azepinyl.

In some cases, E is $CR^1$ and $R^1$ is $C_{0-3}$alkyleneOR$^4$, SR$^4$, SO$_2$R$^4$, C(O)N(R$^4$)$_2$, C(O)OR$_4$, or C(O)SR$^4$. In some of these cases, $R^4$ is H. For example, E can be C—$C_{0-3}$alkyleneOH, SH, SO$_2$H, C(O)NH$_2$, or C(O)OH. In some of these embodiments, $R^4$ is $C_{1-6}$alkyl, $C_{1-4}$ alkyl, or $C_{5-6}$alkyl (e.g., methyl, ethyl, n-propyl, isopropyl, n-butyl, isobutyl, sec-butyl, or tert-butyl). For example, E is C—$C_{0-3}$alkyleneOMe, C—$C_{0-3}$alkyleneOEt, C—$C_{0-3}$alkyleneOPr, SMe, SEt, SPr, SO$_2$Me, SO$_2$Et, SO$_2$Pr, C(O)NMe$_2$, C(O)NEt$_2$, C(O)NPr$_2$, C(O)OMe, C(O)OEt, or C(O)OPr. In some cases, $R^4$ is $C_{0-3}$alkylenearyl (e.g., aryl, $C_1$alkylenearyl, $C_2$alkylenearyl, or $C_3$alkylenearyl). For example, E can be C-phenyl or C—$CH_2$phenyl.

In various cases, G is $C(R^2)_2$. In some embodiments, G is $CH_2$. In various embodiments, one $R^2$ is H and the other $R^2$ is $C_{1-6}$alkyl, for example, $C_{1-4}$ alkyl or $C_{5-6}$alkyl (e.g., methyl, ethyl, n-propyl, isopropyl, n-butyl, isobutyl, sec-butyl, or tert-butyl). For example, G can be CHMe, CHEt, or CH$^t$Bu. In some cases, each $R^2$ independently is $C_{1-6}$alkyl. For example, G can be $C(Me)_2$, CMeEt, $C(Et)_2$, or $C(^tBu)_2$. In various embodiments, G is O. In some cases, G is S. In various cases, G is SO$_2$.

In some cases, n is 0. In various embodiments, n is 1. In some cases, n is 2.

In some embodiments, E is CH, G is $CH_2$, and n is 0. In various embodiments, E is CH, G is $CH_2$, and n is 1. In some cases, E is CH, G is CHMe, and n is 1. In some cases, E is CH, G is CMe$_2$, and n is 1. In various cases, E is CH, G is O, and n is 1. In some embodiments, E is CH, G is S, and n is 1. In various cases, E is CH, G is SO$_2$, and n is 1.

In embodiments where A is formula (B):

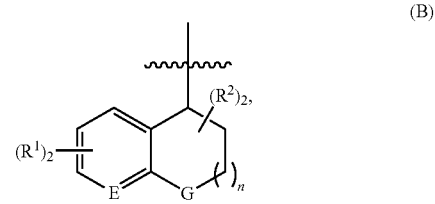

each $R^1$ is other than H. In various cases, one $R^1$ is H and the other $R^1$ is other than H. Specifically contemplated options for $R^1$ include those as described above for $R^1$ when E is $CR^1$. In some embodiments, at least one $R^1$ is H, Ph, $CH_2$Ph, OPh, or naphthyl.

In cases when A is formula (B):

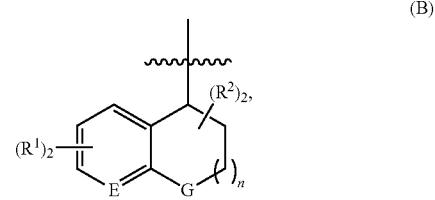

each $R^2$ is H. In various cases, one $R^2$ is H and the other $R^2$ is other than H. In some embodiments, each $R^2$ is other than H. In various cases, at least one $R^2$ is $C_{1-6}$alkyl (e.g., methyl, ethyl, n-propyl, isopropyl, n-butyl, isobutyl, sec-butyl, or tert-butyl). In various embodiments, one $R^2$ is H and the other is $C_{1-6}$alkyl. In some cases, at least one $R^2$ is methyl.

In some cases, E is CH, G is $CH_2$, n is 1, one $R^1$ is benzyl and the other $R^1$ is H, and each $R^2$ is H. In various embodiments, E is CH, G is O, n is 1, one $R^1$ is benzyl and the other $R^1$ is H, and each $R^2$ is H. In some embodiments, E is CH, G is S, n is 1, one $R^1$ is benzyl and the other $R^1$ is H, and each $R^2$ is H. In various cases, E is CH, G is $CH_2$, n is 0, one $R^1$ is benzyl and the other $R^1$ is H, and each $R^2$ is H. In some cases, E is CH, G is $CH_2$, n is 1, one $R^1$ is naphthyl and the other $R^1$ is H, and each $R^2$ is H.

For example, A is formula (B) and is selected from the group consisting of:

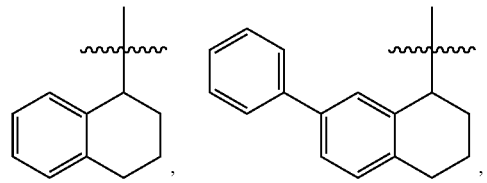

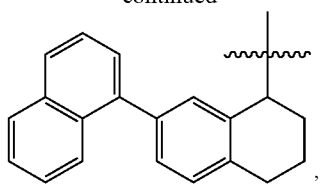,
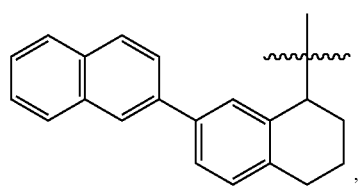,
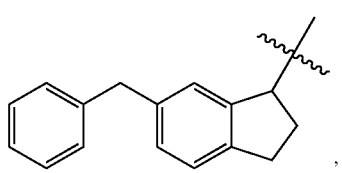,
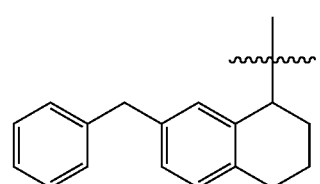,
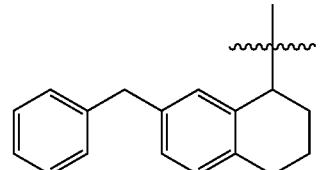,
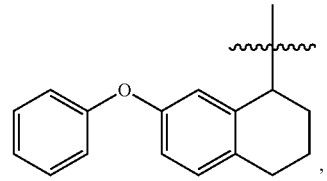,
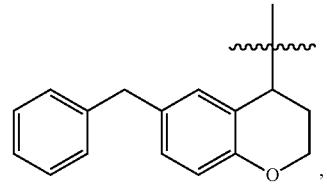,
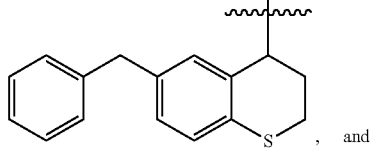, and
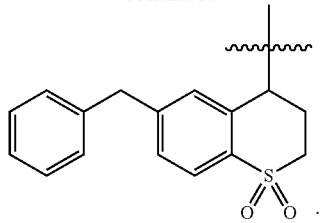.
In some cases, A is formula(C):
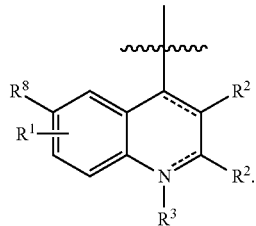 (C)
In some cases when ---- indicates a double bond, formula (C) is a structure selected from the group consisting of
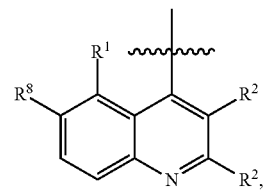,
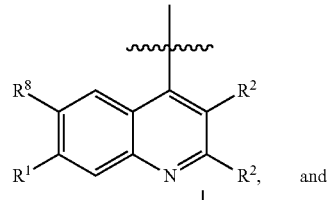, and
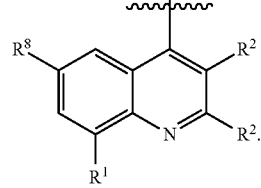.
In some embodiments when ---- indicates a single bond, formula (C) is a structure selected from the group consisting of
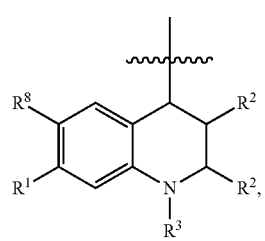,

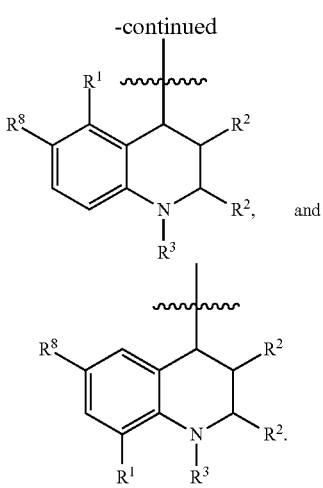

In some embodiments, when formula (C) is

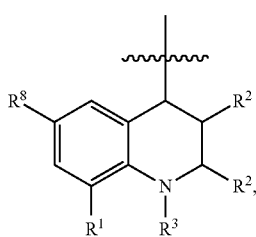

$R^1$ and $R^3$ can connect to form a 5-7 membered ring (e.g., a 6-membered ring).

$R^1$ has been previously described above for when A includes a structure (B). For example, $R^1$ can be OH, $OCH_3$, COOH, $CO_2Et$, $CH_2OPh$, C(O)NHPh, C(O)NHBn,

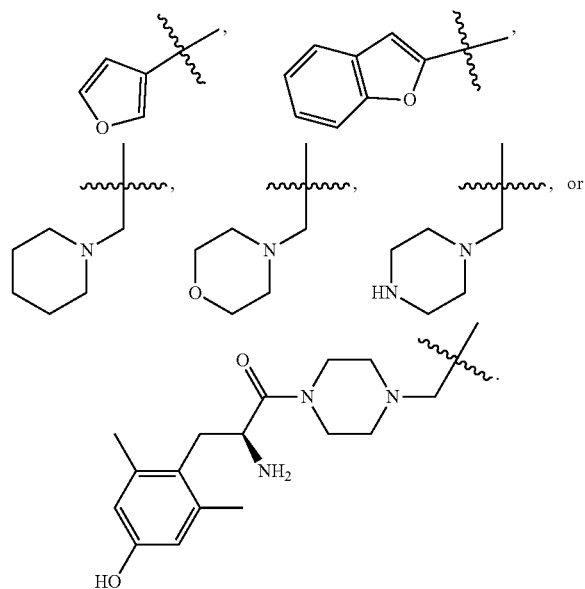

$R^2$ is as previously described herein when A is formula (B). For example, $R^2$ can be H, methyl, ethyl, or propyl.

In some embodiments, ---- indicates a double bond and $R^3$ is absent. In various embodiments, ---- indicates a single bond and $R^3$ is present. In some cases, $R^3$ is H. In various cases, $R^3$ is $C_{1-6}$alkyl or $C_{1-4}$ alkyl or $C_{5-6}$ alkyl (e.g., methyl, ethyl, n-propyl, isopropyl, n-butyl, isobutyl, sec-butyl, or tert-butyl). For example, $R^3$ can be methyl or propyl. In various cases, $R^3$ is $C_{0-3}$alkyleneC(O)$R^4$ or $C_{0-3}$alkyleneC(O)O$R^4$ or $C_{0-3}$alkyleneC(O)O$R^4$ or $C_{0-3}$alkyleneC(O)NH$R^4$. In some of these cases the alkylene group is absent (e.g., C0alkylene). In some of these embodiments, the alkylene group is $C_1$alkylene or $C_2$alkylene or $C_3$alkylene or $C_4$alkylene or $C_5$alkylene or $C_6$alkylene. In some of these cases, $R^4$ is H. For example, $R^3$ can be C(O)H, $CH_2$C(O)H, C(O)OH, or $CH_2$C(O)OH. In some of these embodiments, $R^4$ is $C_{1-6}$alkyl or $C_{1-4}$ alkyl or $C_{5-6}$alkyl (e.g., methyl, ethyl, n-propyl, isopropyl, n-butyl, isobutyl, sec-butyl, or tert-butyl). For example, $R^3$ can be C(O)Me, $CH_2$C(O)Me, C(O)OMe, $CH_2$C(O)Me, C(O)Et, $CH_2$C(O)Et, C(O)OEt, $CH_2$C(O)Et, C(O)Pr, $CH_2$C(O)Pr, C(O)OPr, or $CH_2$C(O)Pr. In some cases, $R^4$ is $C_{0-3}$alkylenearyl (e.g., aryl or $C_1$alkylenearyl). Examples of aryl groups have been previously described herein with respect to substituent $R^1$. For example, $R^3$ can be C(O)Ph, $CH_2$C(O)Ph, C(O)OPh, $CH_2$C(O)Ph, C(O)$CH_2$Ph, $CH_2$C(O) $CH_2$Ph, C(O)O$CH_2$Ph, or $CH_2$C(O)$CH_2$Ph.

In various cases, $R^8$ is H. In some cases, $R^8$ is halo (e.g., F, Cl, Br, or I). For example, $R^8$ is Br. In some cases, $R^8$ is $C_{1-6}$alkyl or $C_{1-4}$ alkyl or $C_{5-6}$ alkyl (e.g., methyl, ethyl, n-propyl, isopropyl, n-butyl, isobutyl, sec-butyl, or tert-butyl). For example, $R^8$ can be pentyl or hexyl. In some embodiments, $R^8$ is $C_{0-6}$alkylenearyl (e.g., $CH_2$-aryl, $CH_2CH_2$-aryl, $CH_2CH_2CH_2$-aryl $CH_2CH_2CH_2CH_2$-aryl, $CH_2CH_2CH_2CH_2CH_2$-aryl, or $CH_2CH_2CH_2CH_2CH_2CH_2$-aryl). In various embodiments, $R^8$ is $C_{0-1}$alkylenearyl. Non-limiting examples of aryl groups have been previously described herein. In some cases, $R^8$ is phenyl, CH(phenyl)$_2$, or $CH_2$phenyl. For example, $R^8$ can be phenyl, benzyl,

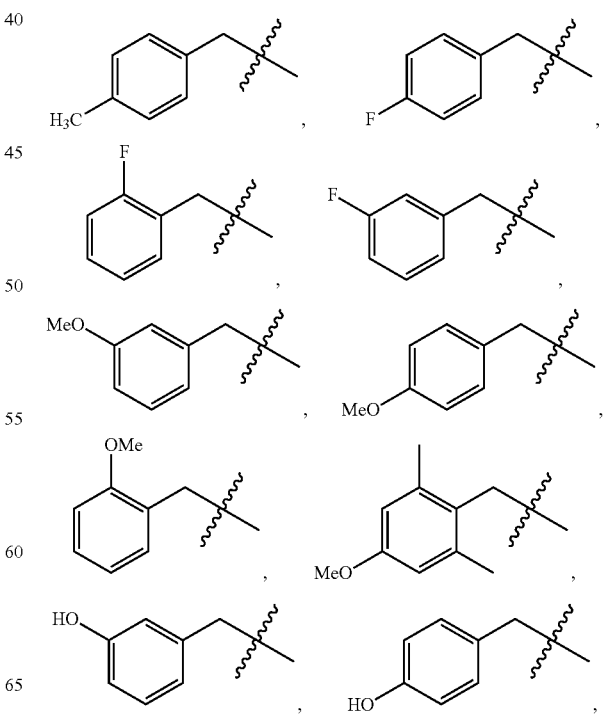

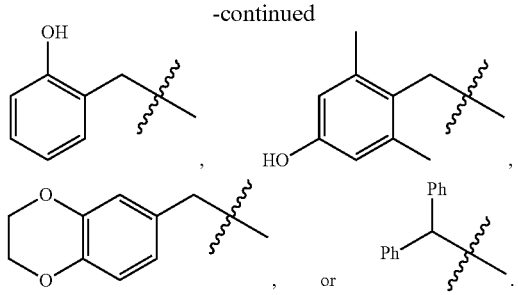

In some cases, $R^8$ is $C_{1-6}$alkyleneheteroaryl (e.g., $C_1$alkyleneheteroaryl, $C_2$alkyleneheteroaryl, $C_3$alkyleneheteroaryl, $C_4$alkyleneheteroaryl, $C_5$alkyleneheteroaryl, or $C_6$alkyleneheteroaryl). In various cases, $R^8$ is thienyl, furanyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. In various embodiments, $R^8$ is furanyl, triazolyl, pyridyl, or quinolyl. In some cases, $R^8$ is furanyl or triazolyl. For example, $R^8$ is

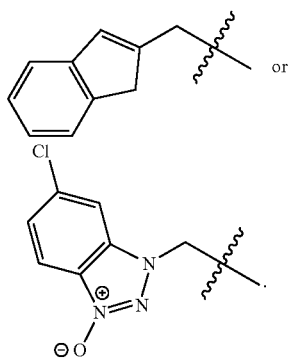

In some cases, $R^8$ is $C_{1-6}$alkylenecycloalkyl or $C_{1-2}$alkylenecycloalkyl or $C_{3-6}$alkylenecycloalkyl. Nonlimiting examples of the cycloalkyl group include cyclopropyl, cyclobutyl, cyclopentyl, cyclohexyl, cycloheptyl, or cyclooctyl). In various cases, $R^8$ is cyclopentyl or $CH_2$cyclopentyl. For example, $R^8$ is

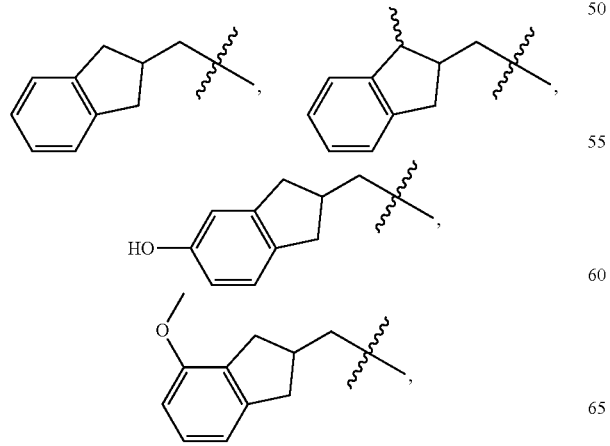

In some cases, $R^8$ is $C_{1-6}$alkyleneheterocycloalkyl or $C_{0-3}$alkyleneheterocycloalkyl or $C_{4-6}$alkyleneheterocycloalkyl. Nonlimiting examples of the heterocycloalkyl group include piperidinyl, piperazinyl, azepinyl, pyrrolidinyl, dithianyl, morpholino, or dioxanyl. In some cases, $R^8$ is $CH_2$piperidinyl, $CH_2$piperazinyl, $CH_2$pyrrolidinyl, or $CH_2$azepinyl. For example, $R^8$ is

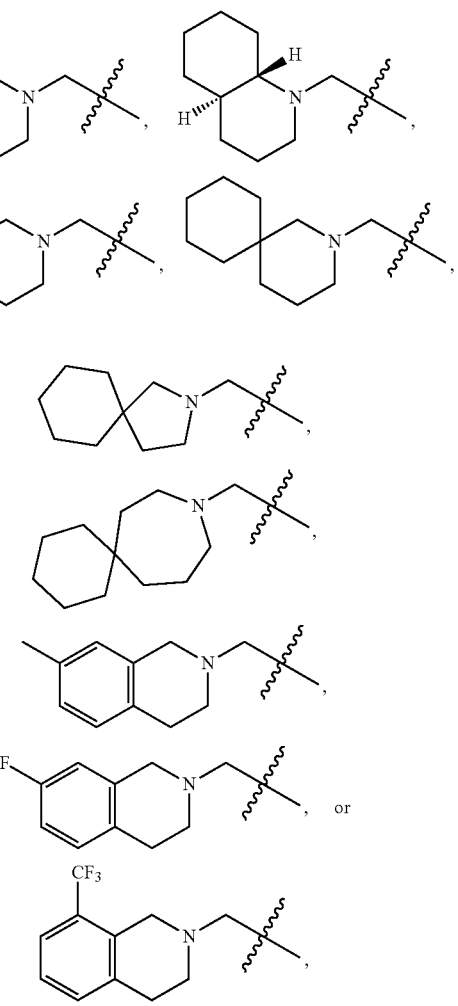

In some cases, $R^8$ is O-aryl. In some cases, $R^8$ is S-aryl. In some cases, $R^8$ is $SO_2$-aryl. Examples of suitable aryl groups have been previously described, e.g., for $R^1$. For example, $R^8$ is OPh, SPh, $SO_2$Ph,

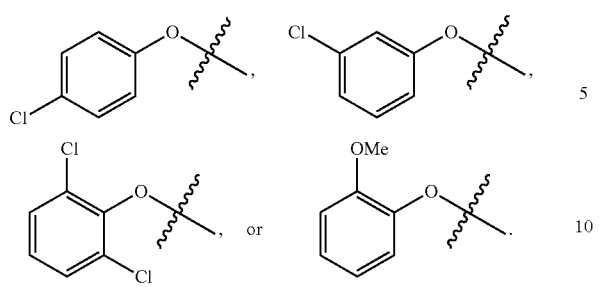

In some of these cases, $R^8$ can be unsubstituted. In various cases, $R^8$ can be substituted. Examples of substituents for $R^8$ include $C_{1-4}$alkyl (e.g., methyl, ethyl, propyl, or butyl), hydroxyl, $C_{1-4}$alkoxy (e.g., methoxy, ethoxy, propoxy, or butoxy), halo (e.g., F, Cl, Br, or I), aryl (e.g., phenyl), haloalkyl (e.g., $CF_3$), cyano, nitro, and amino.

For example, A can be formula (C) and have a structure selected from:

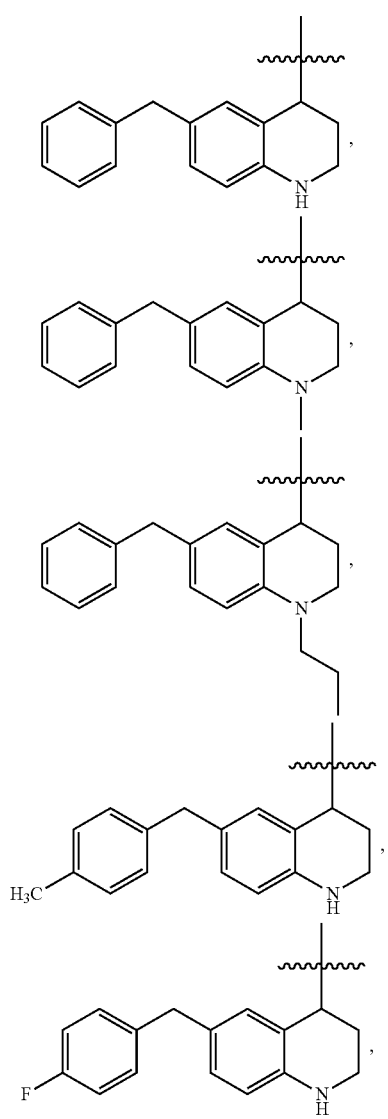

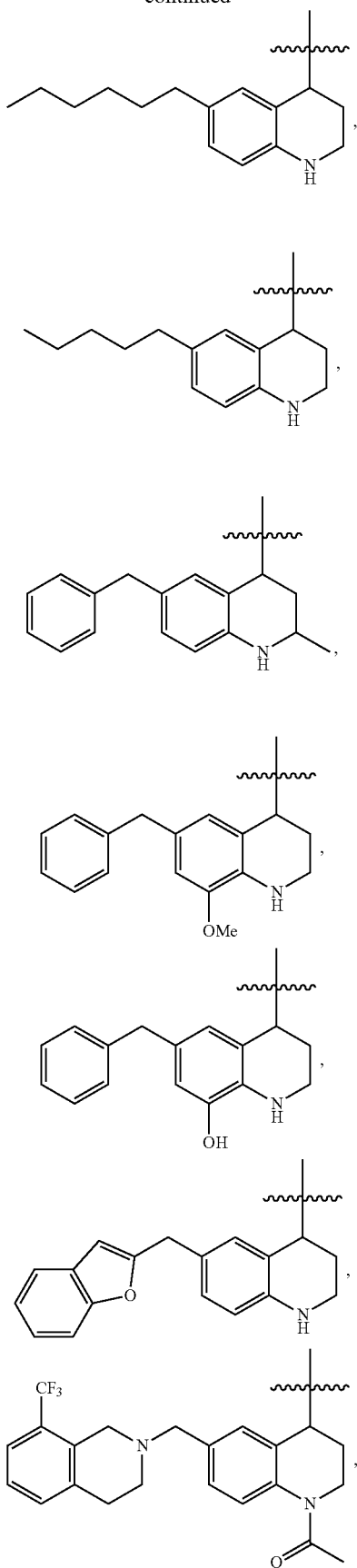

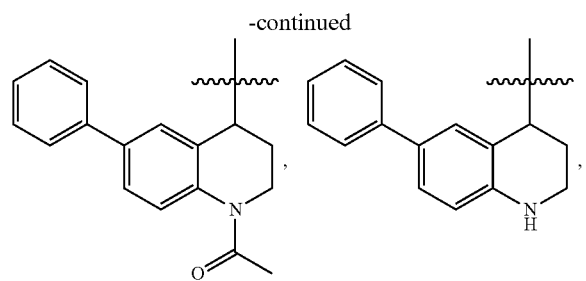
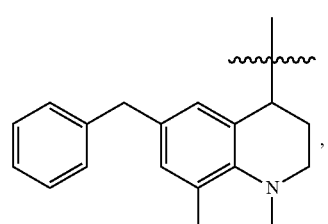
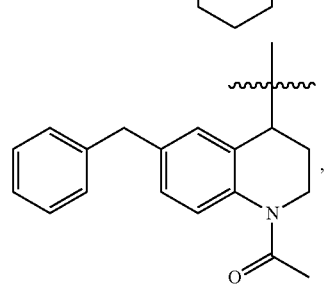
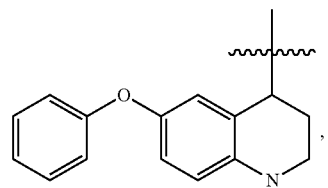
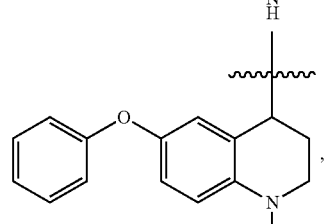
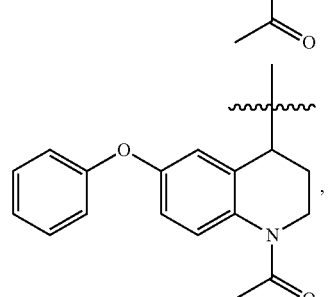
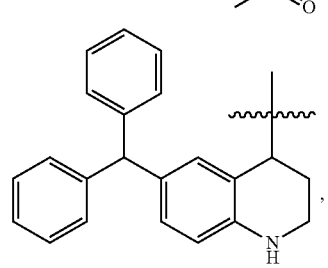
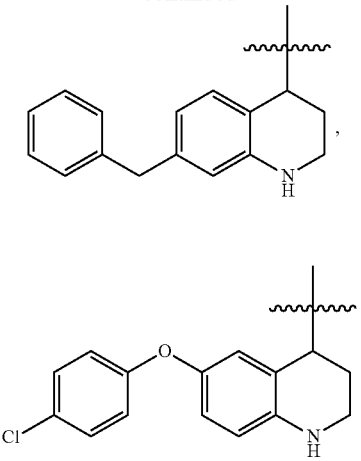
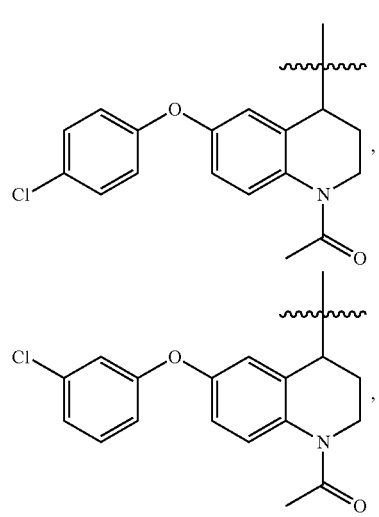
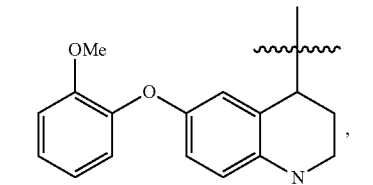
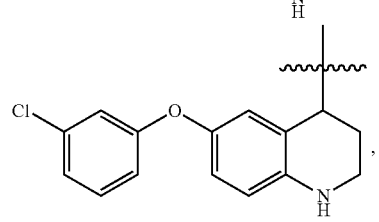
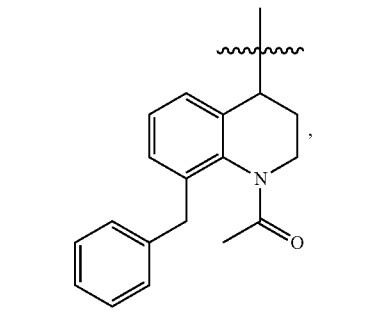

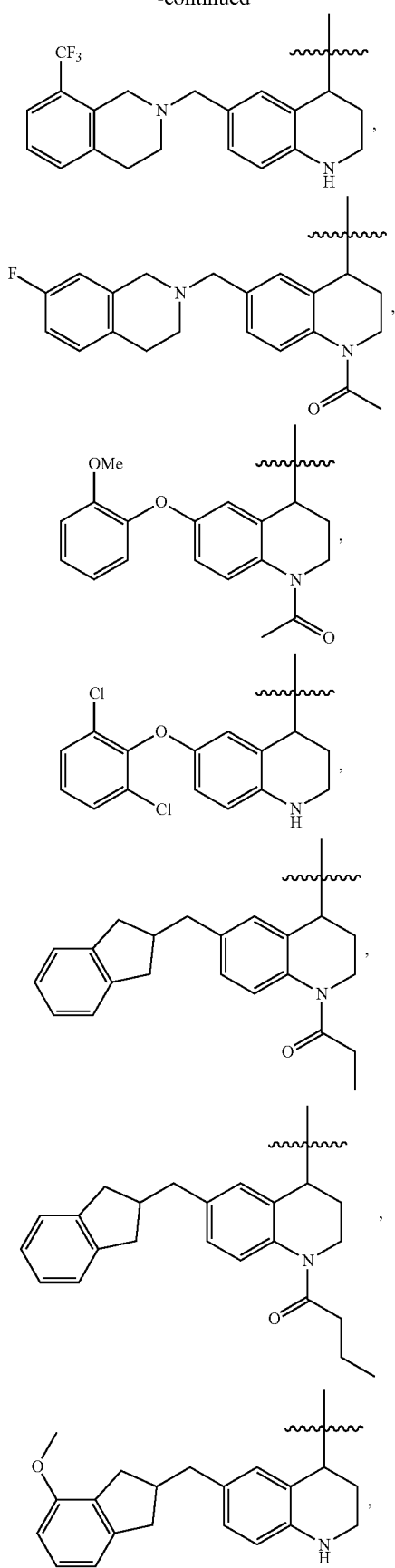
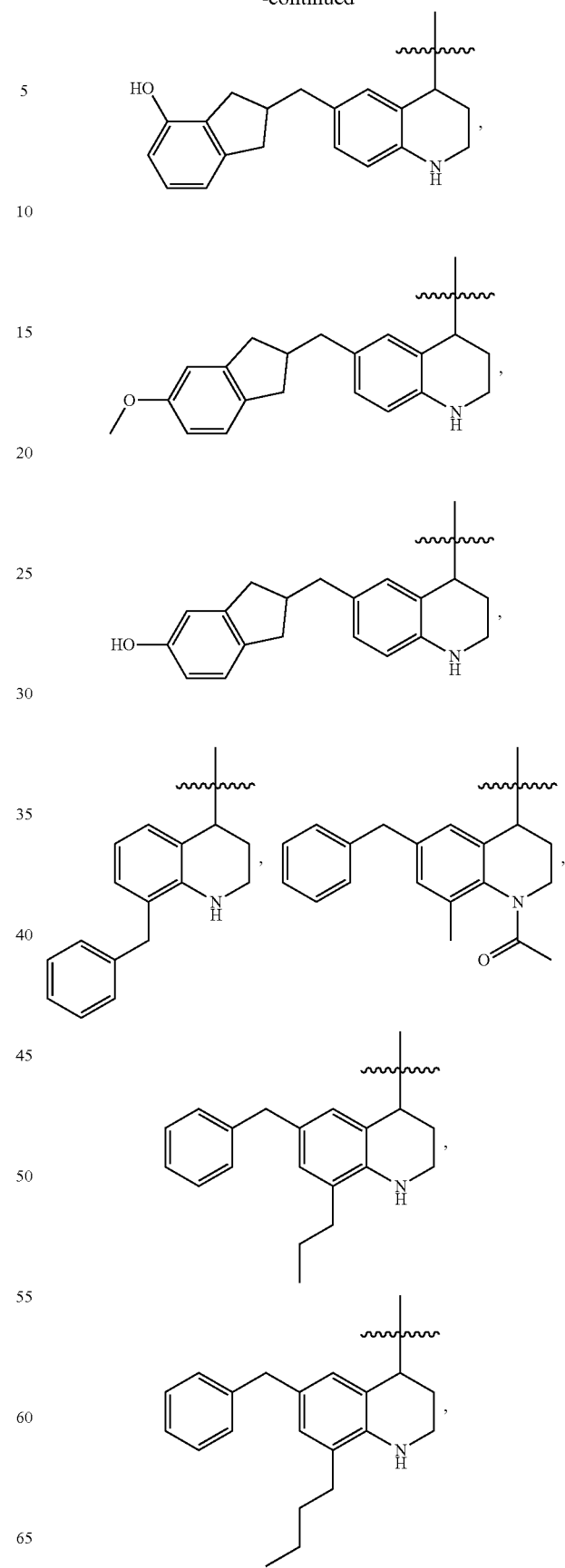

57
-continued
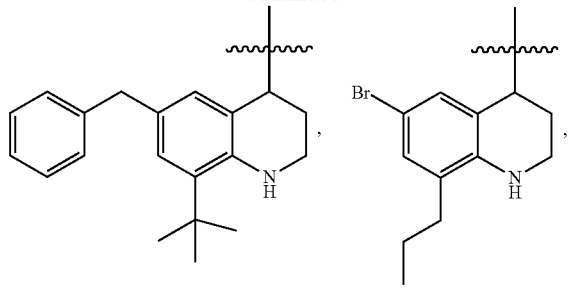
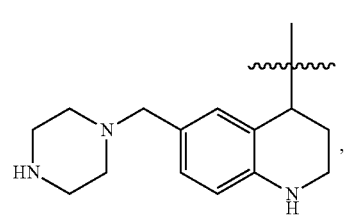
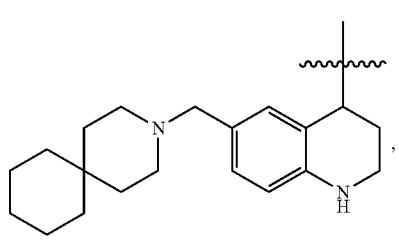
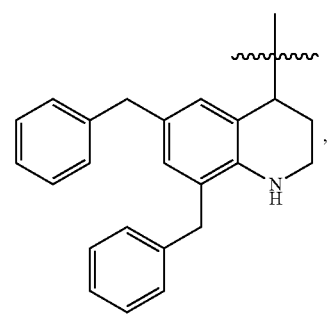
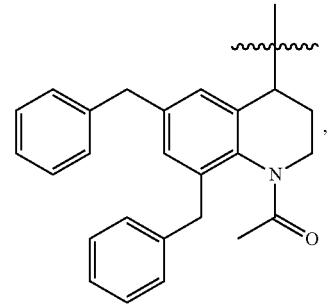
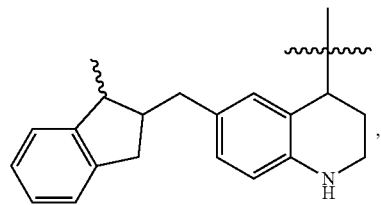
58
-continued
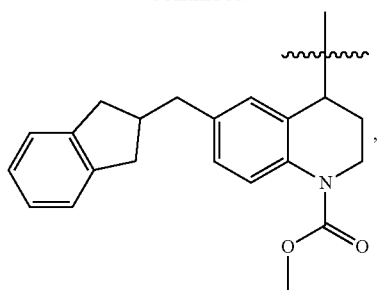
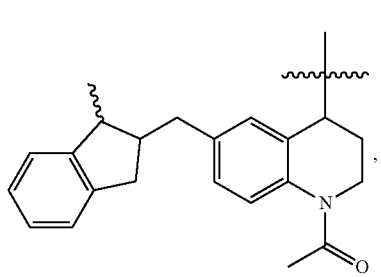
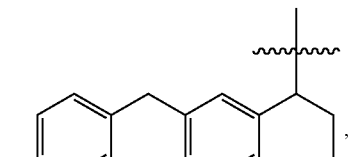
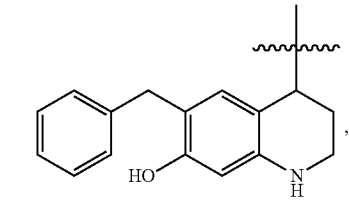
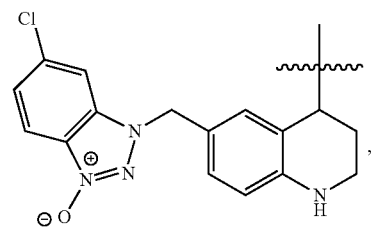
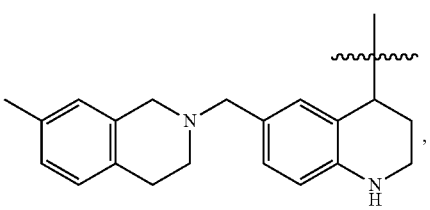
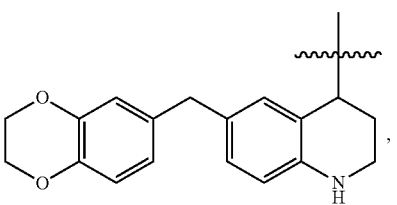

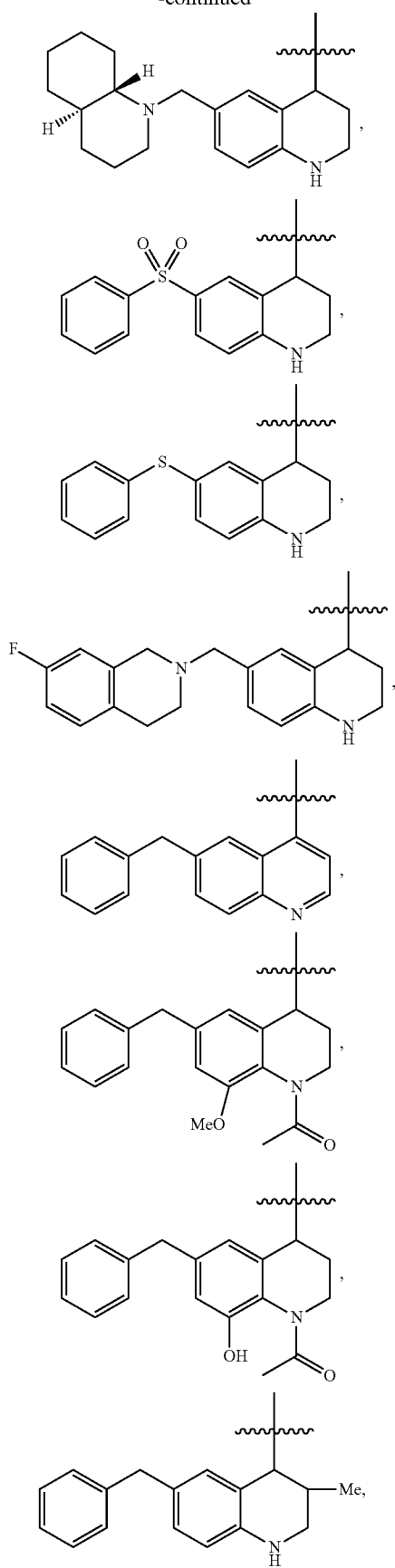
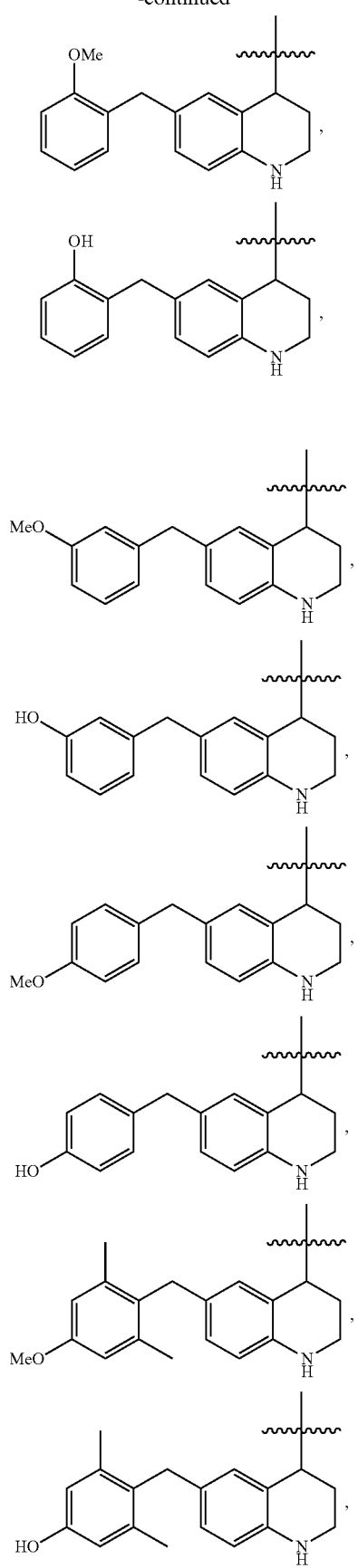

61
-continued
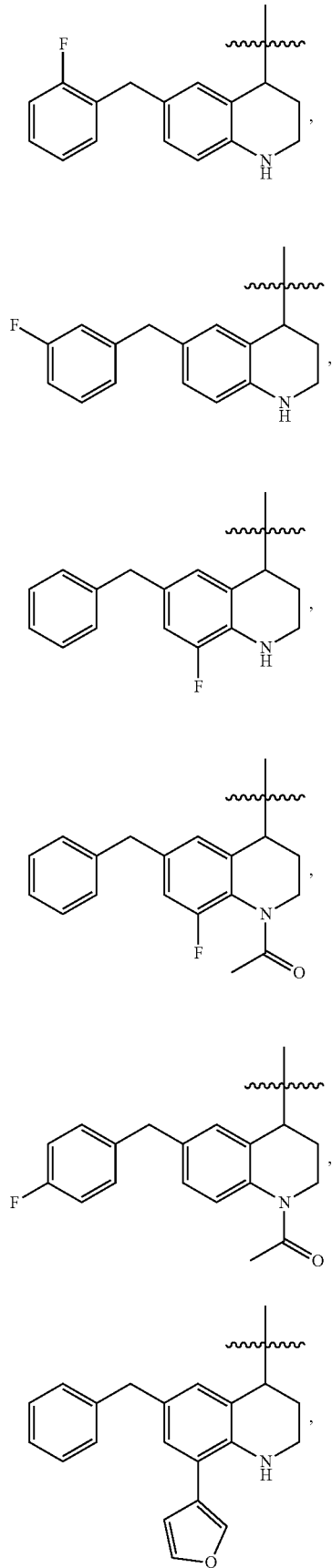
62
-continued
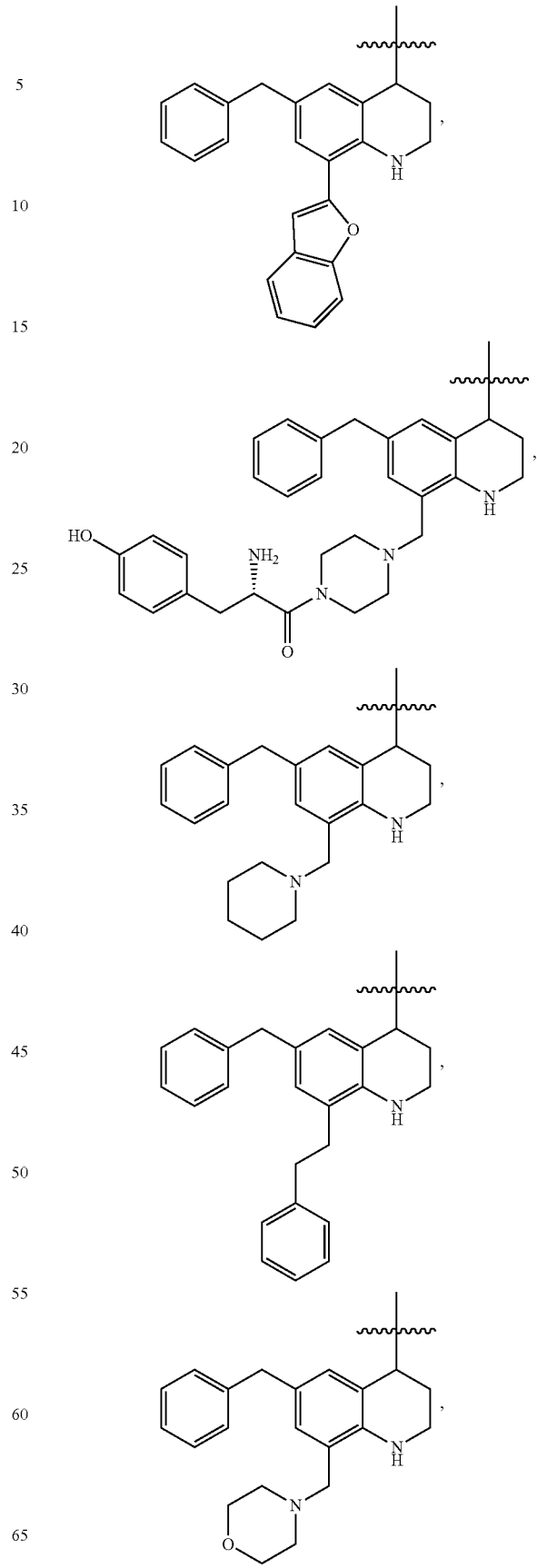

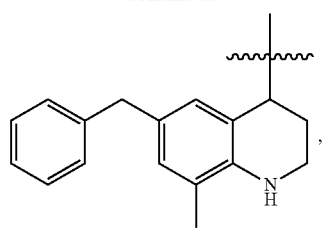,
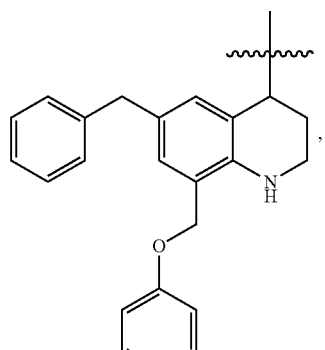,
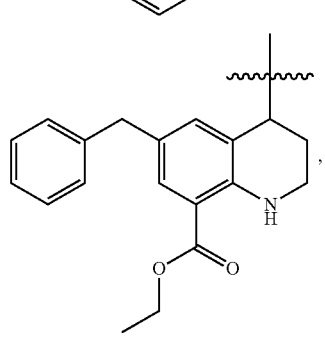,
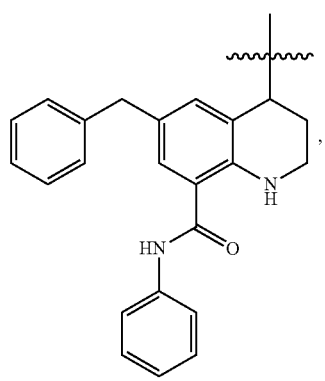,
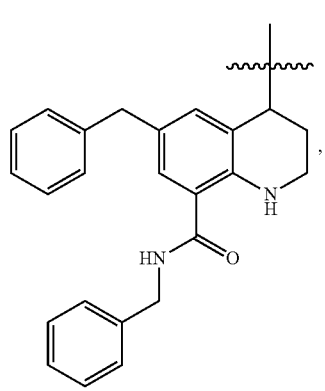,
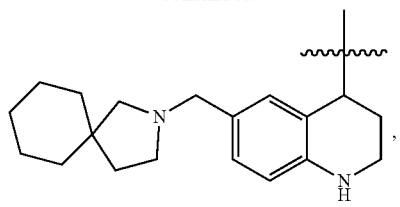,
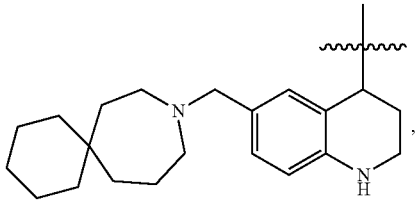,
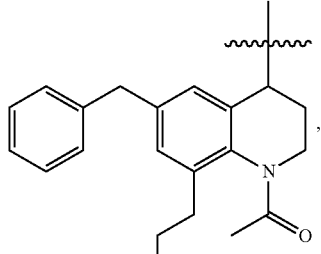,
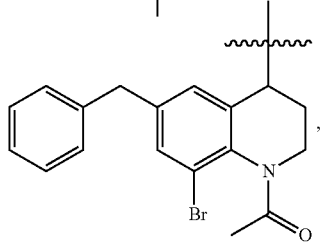,
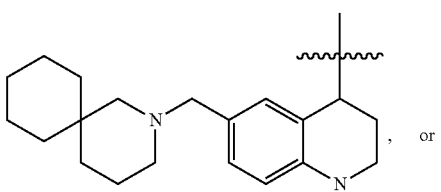, or
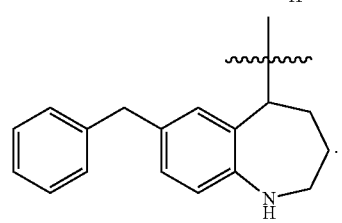.
In some cases, A is formula (D):
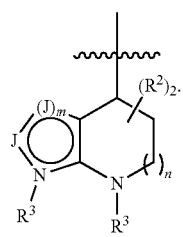
(D)

In various cases, m is 1. In some cases, m is 2. In various embodiments, n is 0. In some cases, n is 1. In various cases, n is 2. In some embodiments, m is 1 and n is 1. In some cases, m is 2 and n is 1.

Each of $R^2$ and $R^3$ are as previously described herein for compounds in which A includes structure (B) or (C). For example, $R^2$ can include H. Suitable $R^3$ groups include H.

In some embodiments, at least one J is $NR^3$. In various cases, at least one J is $CR^1$ and at least one J is $NR^3$. In some embodiments, $R^3$ is absent and J is N. In various embodiments, at least one J is $CR^1$. In some cases, each J is $CR^1$. $R^1$ is as previously described herein for compounds in which A is formula (B) or (C). In some embodiments, J can be NMe, or NPr. In various embodiments, J can be NC(O)H, $NCH_2C(O)H$, NC(O)OH, or $NCH_2C(O)OH$. In some cases, J can be NC(O)Me, $NCH_2C(O)Me$, NC(O)OMe, $NCH_2C(O)Me$, NC(O)Et, $NCH_2C(O)Et$, NC(O)OEt, $NCH_2C(O)Et$, NC(O)Pr, $NCH_2C(O)Pr$, NC(O)OPr, or $NCH_2C(O)Pr$. In various embodiments, J can be NC(O)Ph, $NCH_2C(O)Ph$, NC(O)OPh, $NCH_2C(O)Ph$, $NC(O)CH_2Ph$, $NCH_2C(O)$, $NCH_2Ph$, $NC(O)OCH_2Ph$, or $NCH_2C(O)CH_2Ph$. In some embodiments, J is CH. In various embodiments, J can be CF, CCl, CBr, or CI. In some cases, J can be CMe, CEt, CPr, or $C^tBu$. In some embodiments, J can be C-phenyl, C-chlorophenyl, C-fluorophenyl, C-hydroxyphenyl, C-methylphenyl, C-methoxyphenyl, C-2,4-methoxychlorophenyl, or C-4-hydroxy-2,6-dimethylphenyl. In some cases, J can be C-phenyl, C-benzyl, C-phenethyl, C-naphthyl, C—$CH_2$naphthyl, or C—CH(phenyl)$_2$. For example, J can be C—$CH_2$Ph or C—$CH_2CH_2$Ph. In some embodiments, J can be C-furanyl, C-benzofuranyl, or C-quinolinyl, such as C-furanyl. In some cases, J can be C-piperidinyl, C-piperazinyl, C-morpholino, or C-pyrrolidinyl. In various embodiments, J is C-piperidinyl, C-morpholino, or C-piperazinyl. For example, J can be C—$CH_2$piperidinyl, C—$CH_2$piperazinyl, C—$CH_2$pyrrolidinyl, or C—$CH_2$azepinyl. In some cases, J is C—$C_{0-3}$alkyleneOH, SH, $SO_2H$, $C(O)NH_2$, or C(O)OH. In some embodiments, J is C—$C_{0-3}$alkyleneOMe, C—$C_{0-3}$alkyleneOEt, C—$C_{0-3}$alkyleneOPr, SMe, SEt, SPr, $SO_2Me$, $SO_2Et$, $SO_2Pr$, $C(O)NMe_2$, $C(O)NEt_2$, $C(O)NPr_2$, C(O)OMe, C(O)OEt, or C(O)OPr. In some cases, J can be C-phenyl or C—$CH_2$phenyl.

For example, A is formula (D) and is

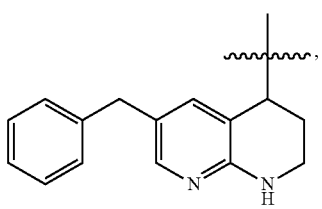,

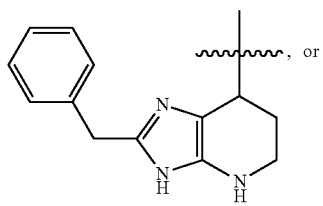, or

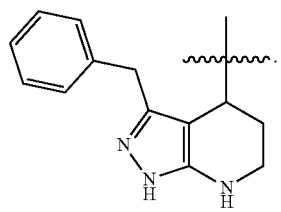.

In various cases, $R^5$ is H. In some cases, $R^5$ is $C_{1-3}$ alkyl (e.g., methyl, ethyl, propyl, or isopropyl). In some cases, $R^5$ is methyl. In some cases, $R^5$ is $C_{3-6}$cycloalkyl (e.g., cyclopropyl, cyclobutyl, cyclopentyl, or cyclohexyl). In some cases, $R^5$ is cyclopropyl.

In various cases, each $R^6$ independently is H. In some embodiments, one $R^6$ is H and one $R^6$ is other than H. In various embodiments, each $R^6$ is other than H. In some cases, at least one $R^6$ is $C_{1-3}$alkyl (e.g., methyl, ethyl, or propyl), such as $CH_3$. In some embodiments, each $R^6$ group is $CH_3$. In some cases, at least one $R^6$ is OH. In various cases, at least one $R^6$ is $C_{1-3}$alkoxy (e.g., O-methyl, O-ethyl, or O-propyl), such as O-methyl. In some cases, each $R^6$ group is O-methyl. In various cases, at least one $R^6$ is halo (e.g., F, Cl, Br, or I), such as Cl. In some cases, each $R^6$ is halo. In various cases, at least one $R^6$ independently is $C(O)N(R^3)_2$, where $R^3$ is as previously described herein. In some embodiments, each $R^6$ group is $C(O)N(R^3)_2$. In some cases, each $R^6$ independently is H, $CH_3$, or Cl. In some embodiments, each $R^6$ is meta to $R^7$. In some of these cases, each $R^6$ is $CH_3$ and $R^7$ is OH.

In some cases, $R^7$ is H. In various cases, $R^7$ is $C_{1-3}$alkyl (e.g., methyl, ethyl, or propyl), such as $CH_3$. In some cases, $R^7$ is OH. In various cases, $R^7$ is $C_{1-3}$alkoxy (e.g., O-methyl, O-ethyl, or O-propyl), such as O-methyl. In various cases, $R^7$ is halo (e.g., F, Cl, Br, or I), such as Cl. In various cases, $R^7$ is $C(O)N(R^3)_2$, wherein $R^3$ is as previously described herein. In some cases, $R^7$ is $C(O)NH_2$. In some cases, $R^7$ is OH, $OCH_3$, Cl, or $C(O)NH_2$.

Specific compounds contemplated herein include

1001

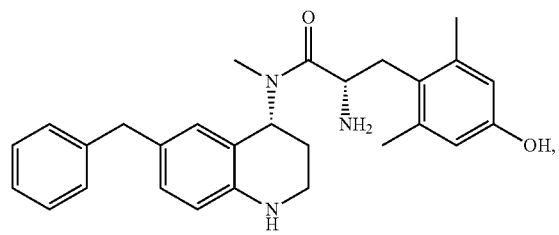

1002

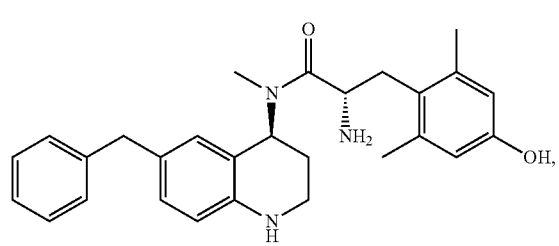

1003
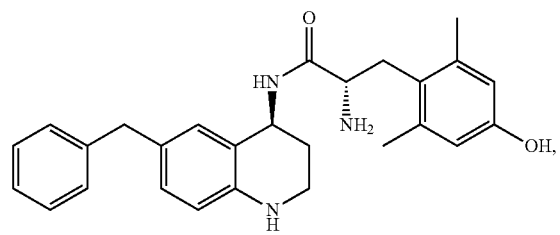
1004
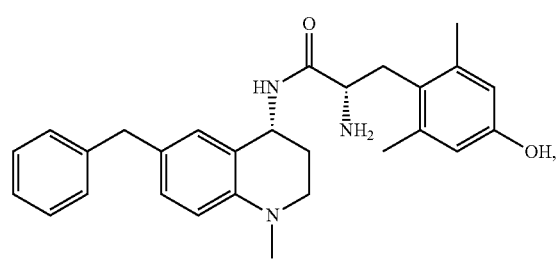
1005
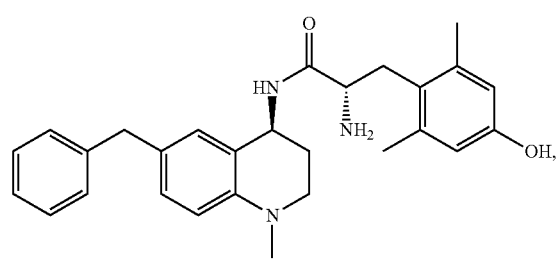
1006
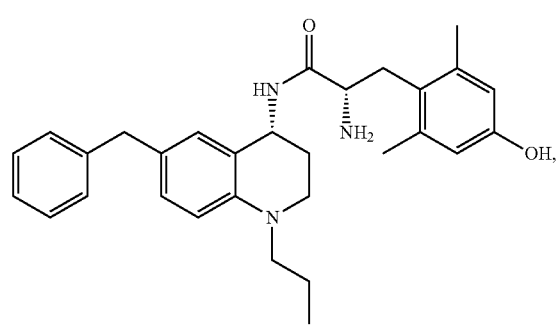
1007
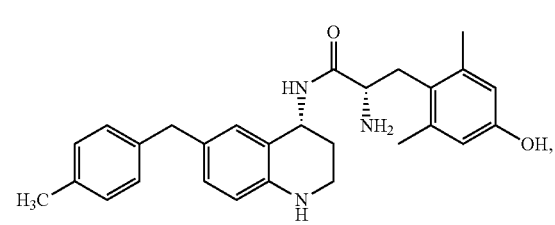
1008
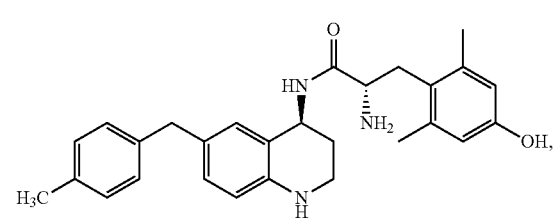
1009
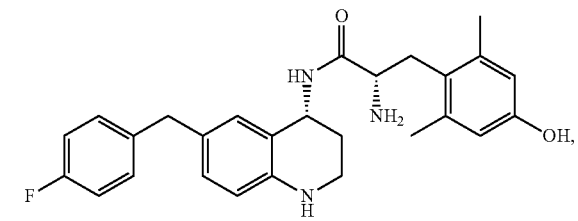
1010
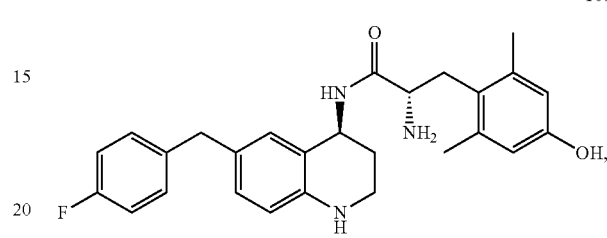
1011
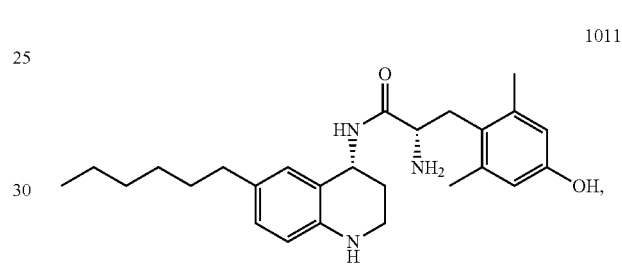
1012
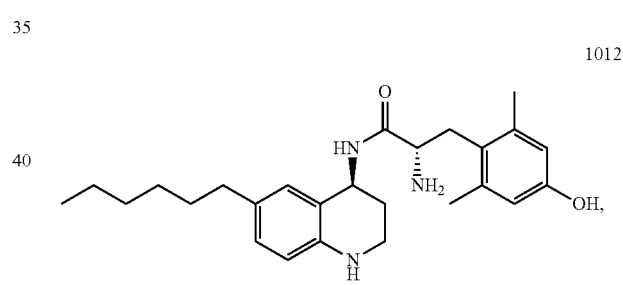
1013
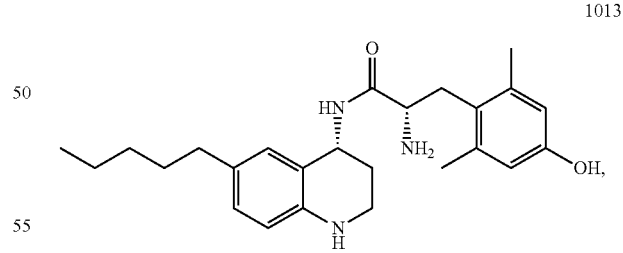
1014
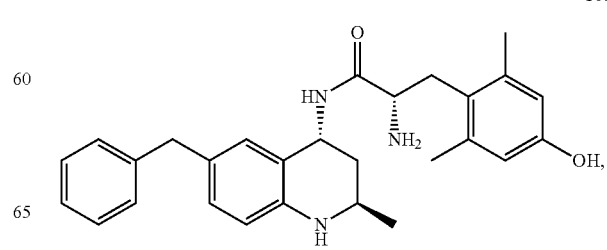

1015
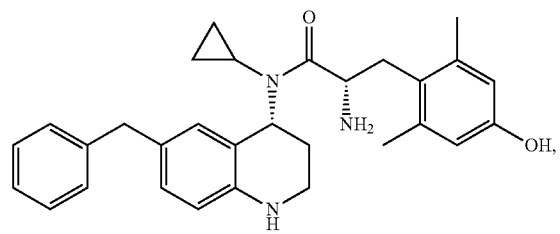
1021
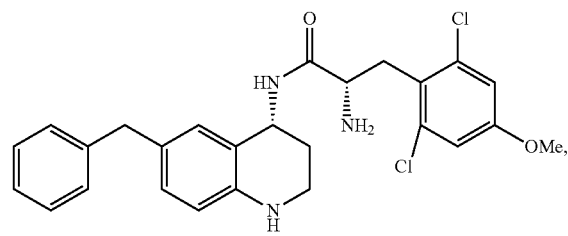
1016
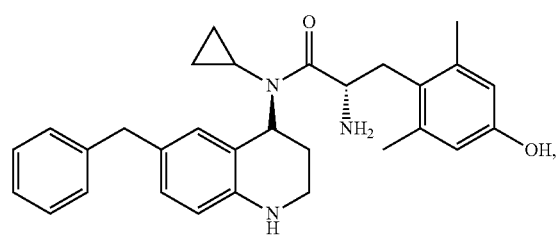
1022
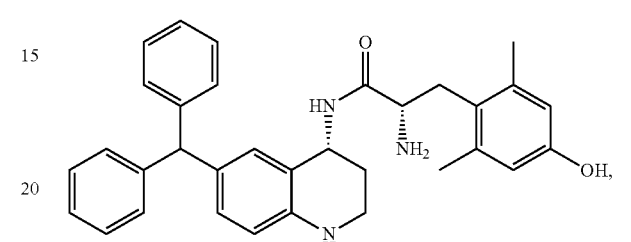
1017
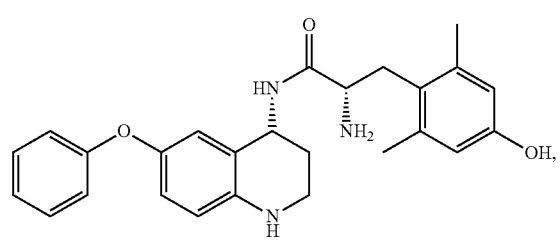
1023
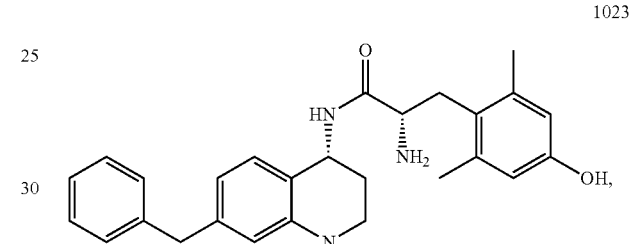
1018
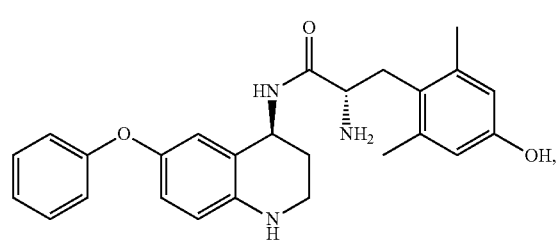
1024
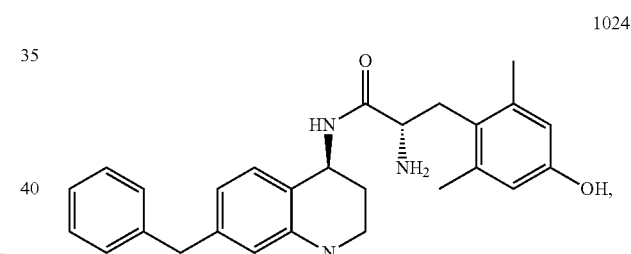
1019
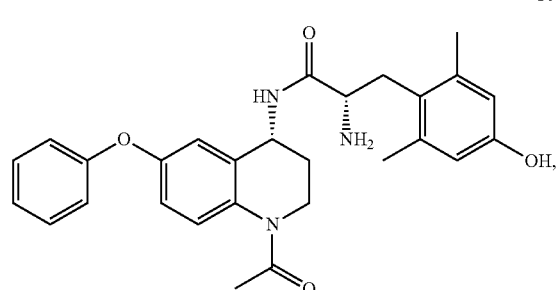
1025
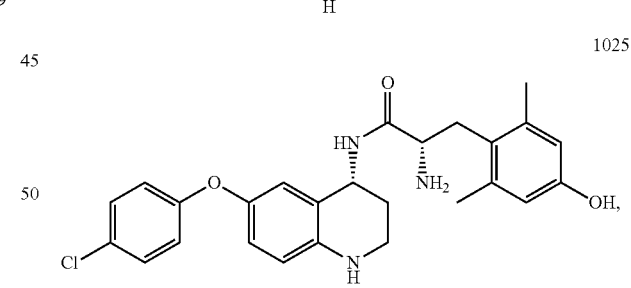
1020
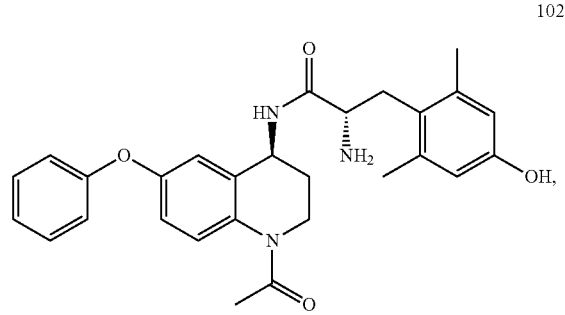
1026
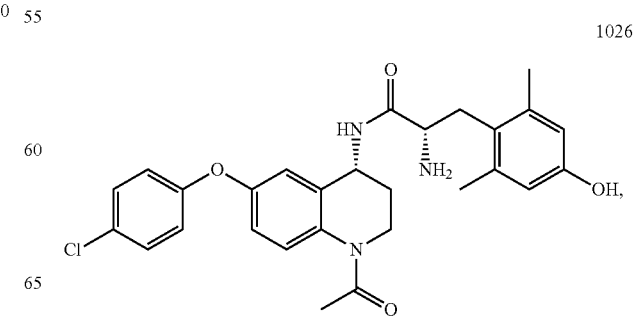

1027
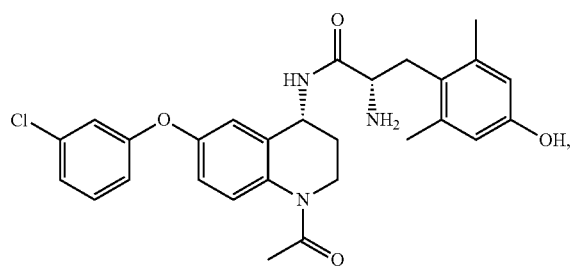
1028
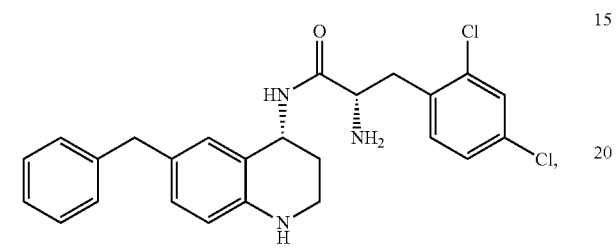
1029
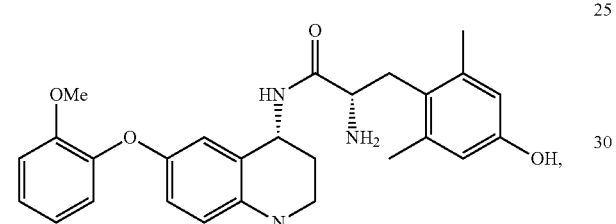
1030
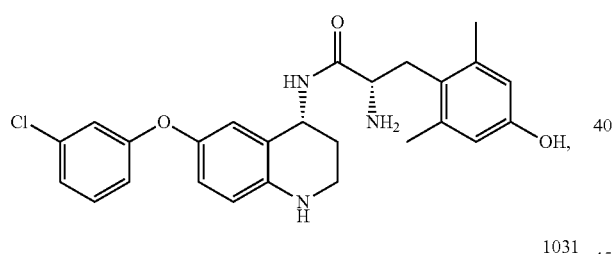
1031
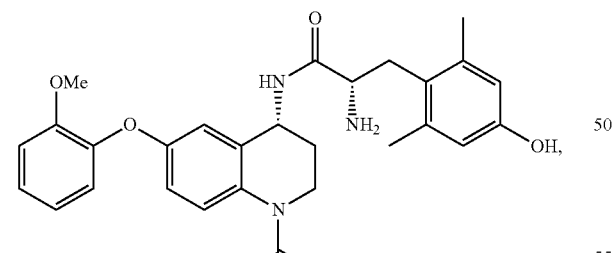
1032
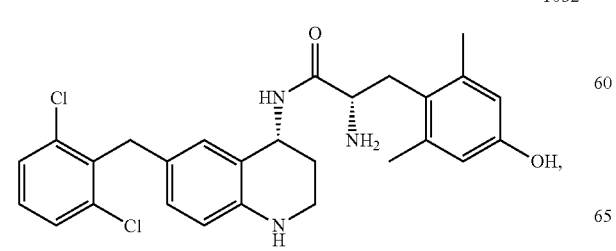
1033
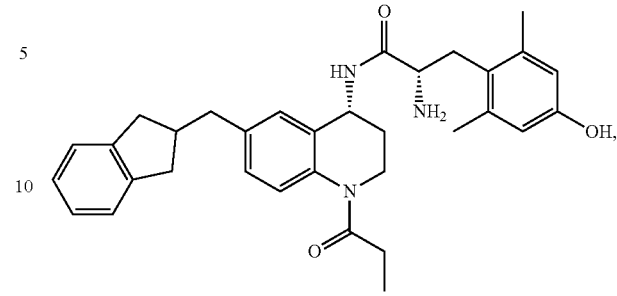
1034
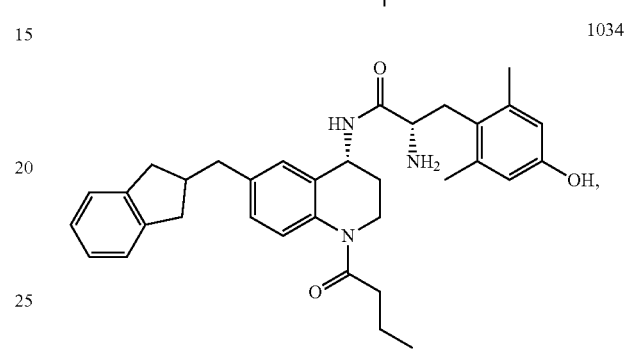
1035
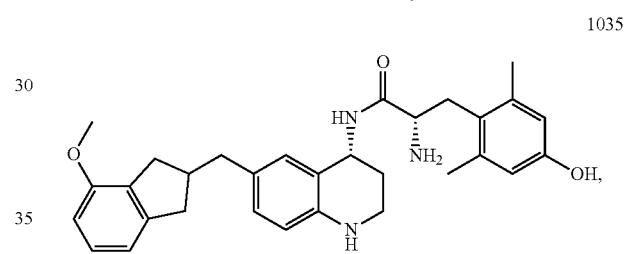
1036
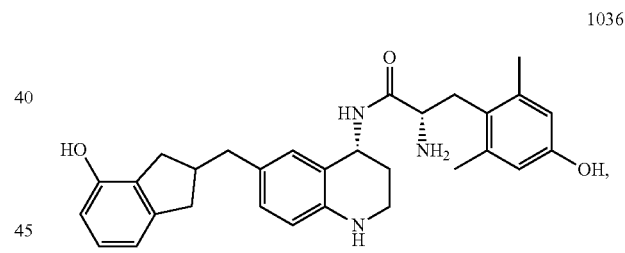
1037
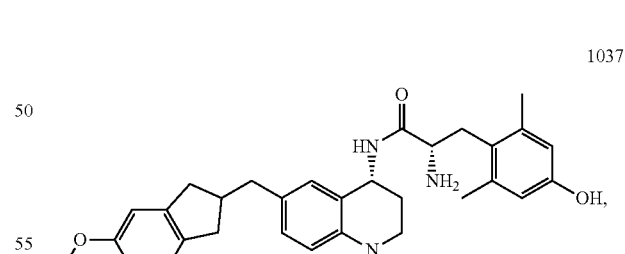
1038
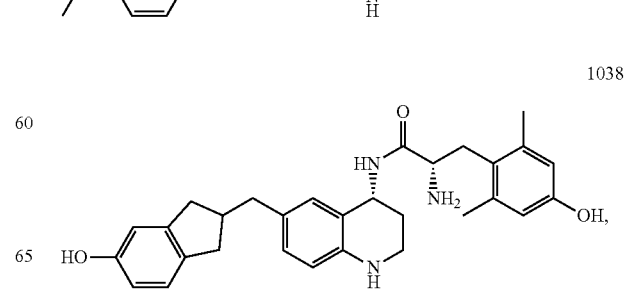

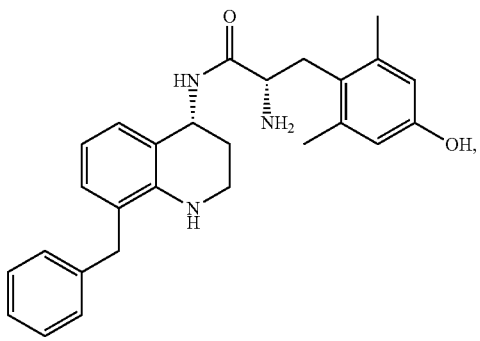
1039
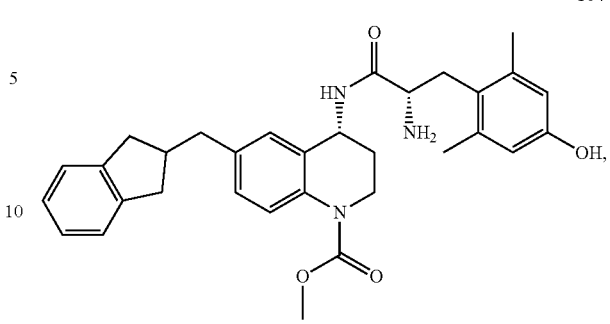
1044
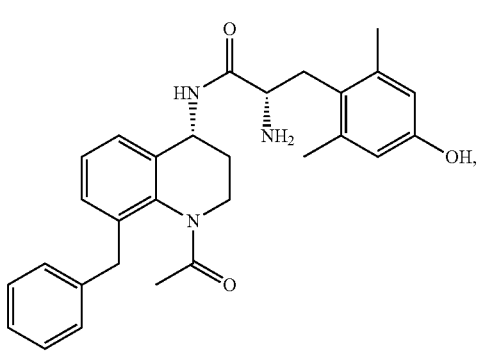
1040
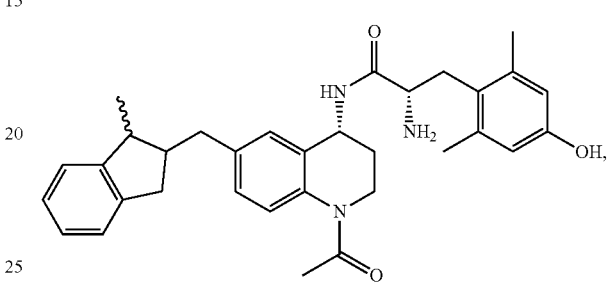
1125
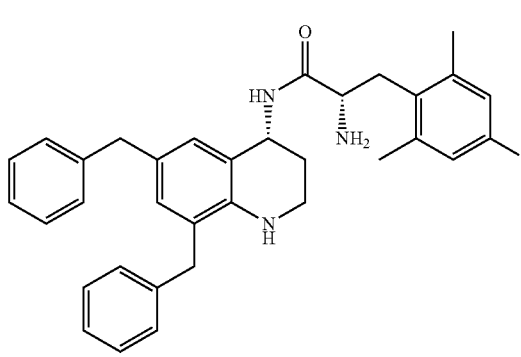
1041
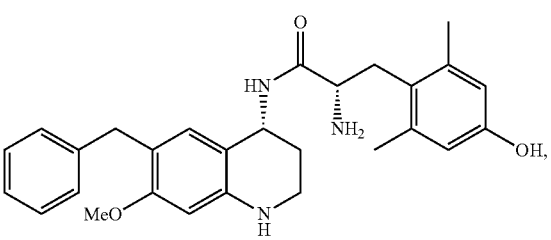
1045
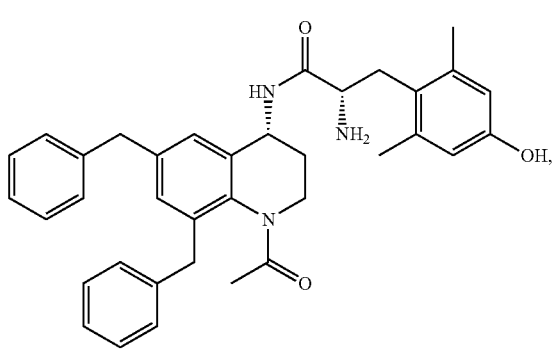
1042
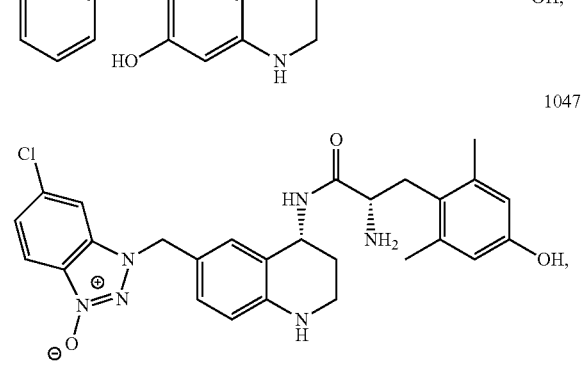
1046
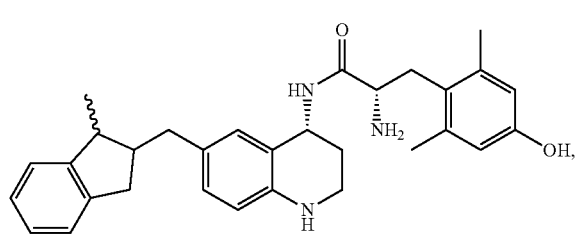
1043
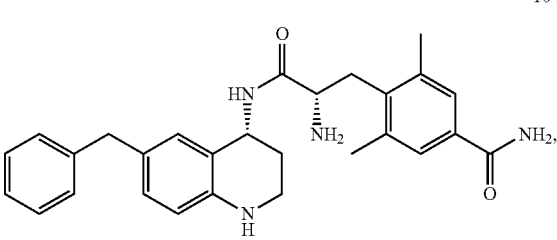
1047

1049
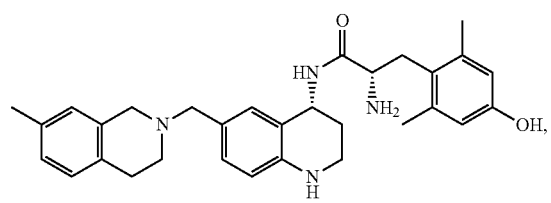
1050
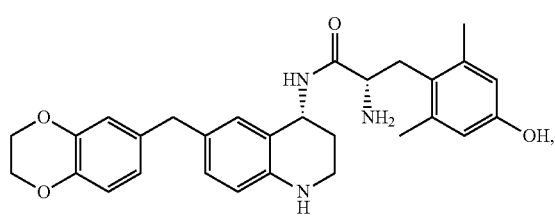
1051
1052
1053
1054
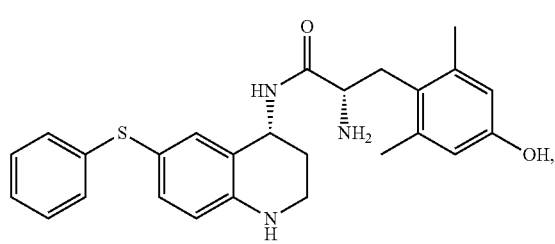
1055
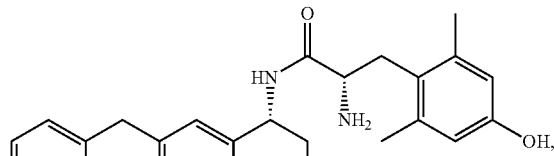
1056
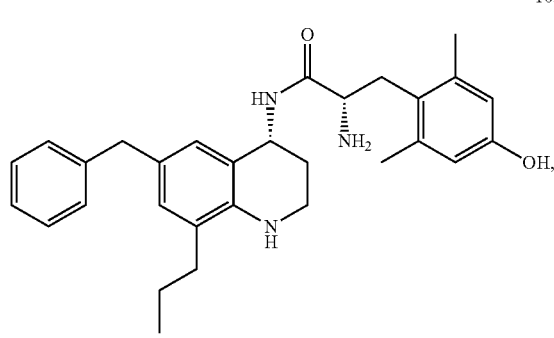
1126
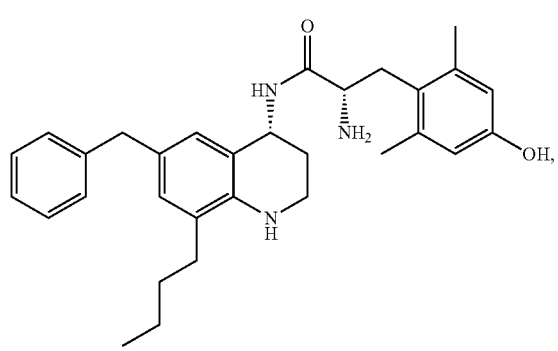
1057
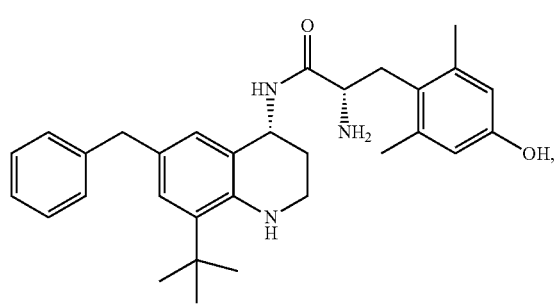
1058
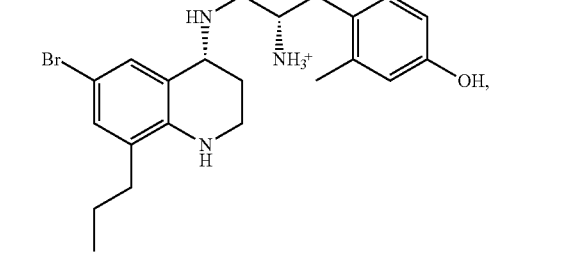

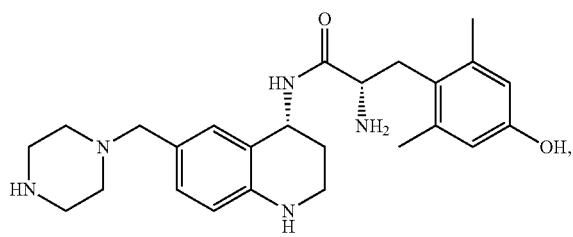
1059
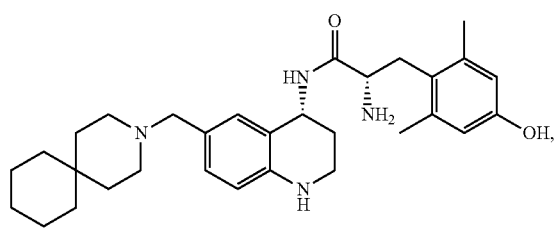
1060
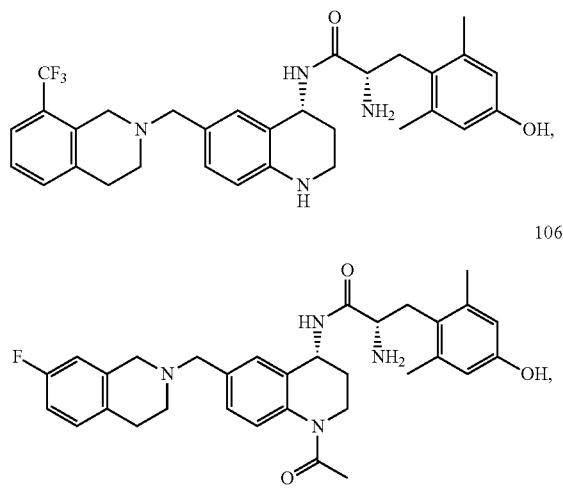
1061
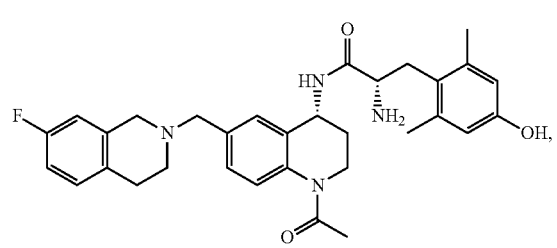
1062
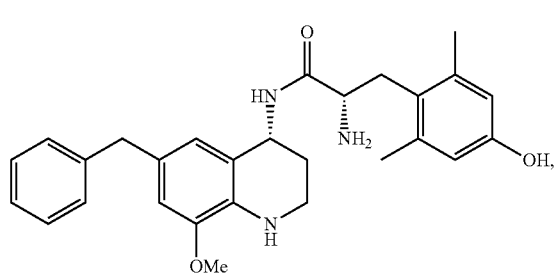
1063
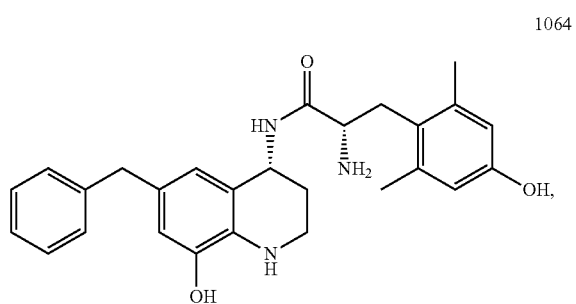
1064
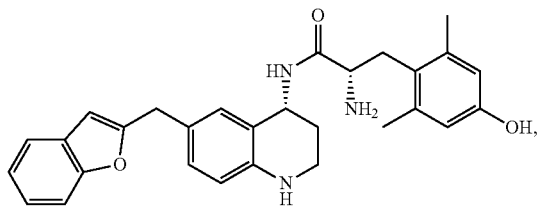
1065
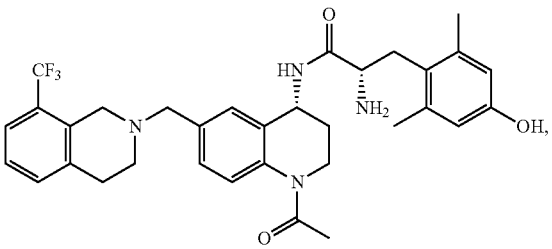
1066
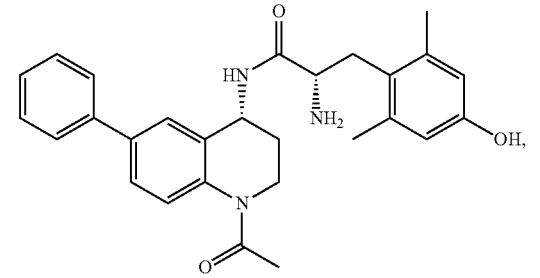
1067
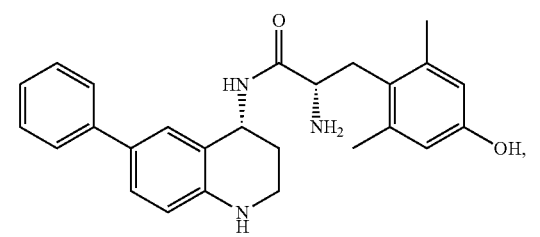
1068
1069

1070 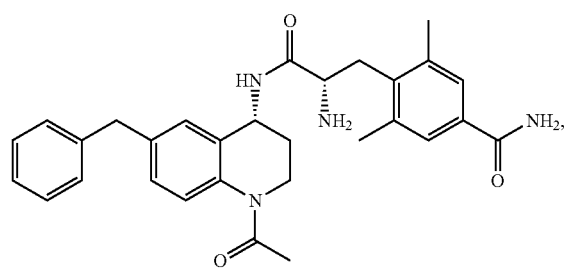
1071 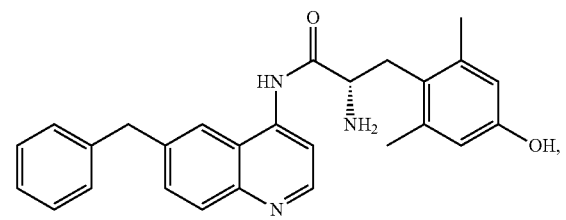
1072 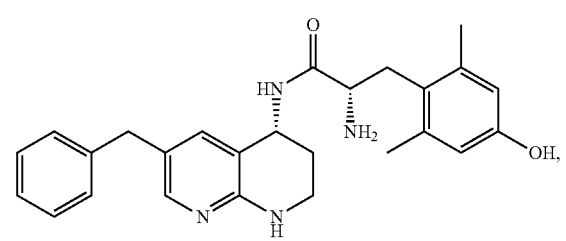
1073 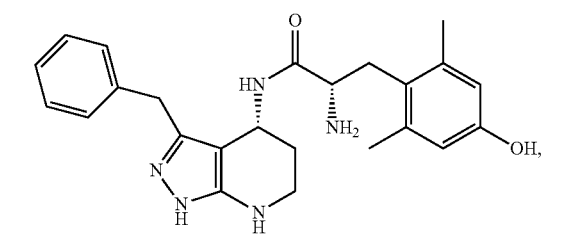
1074 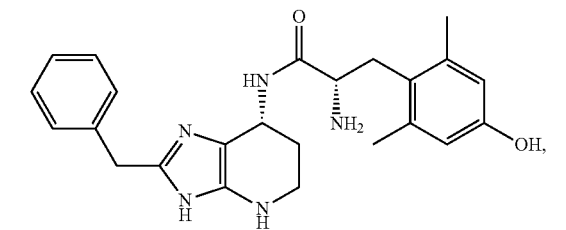
1075 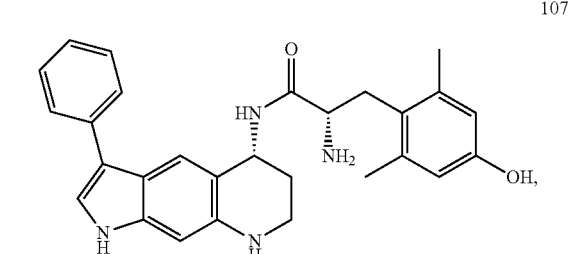
1076 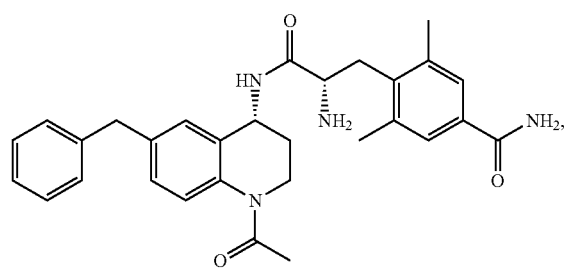
1077 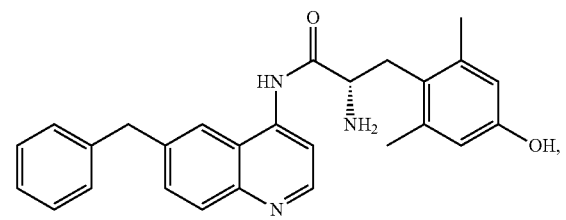
1078 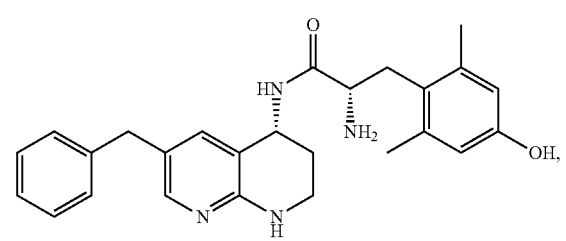
1079 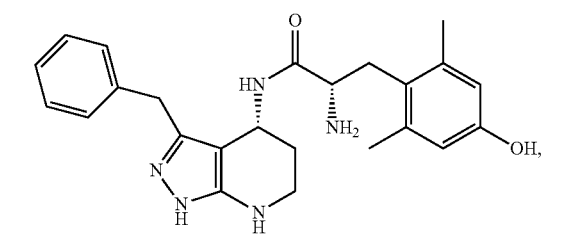
1080 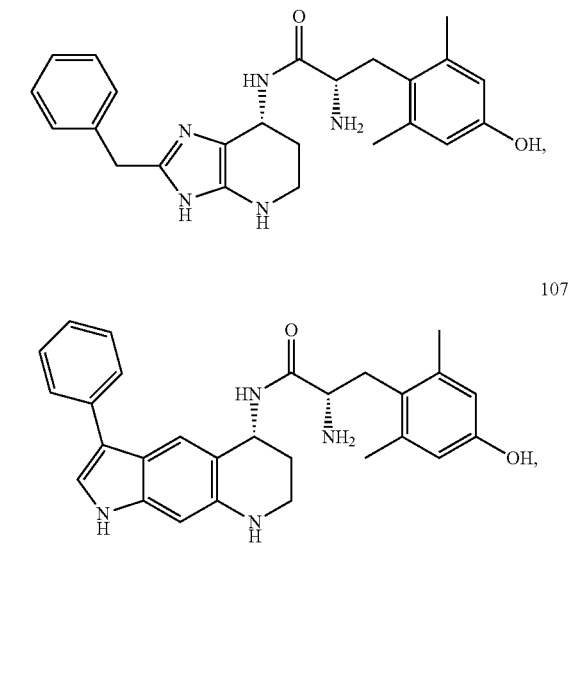

1081
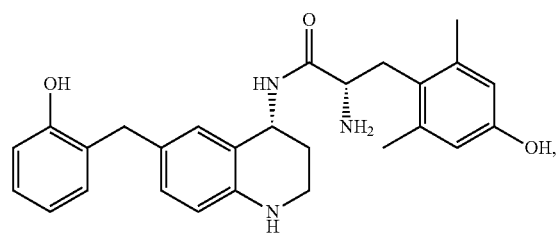
1082
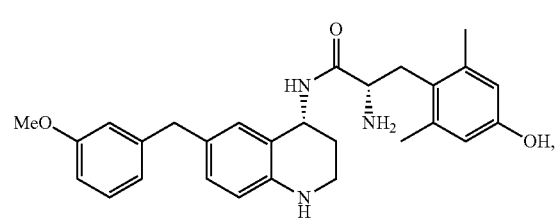
1083
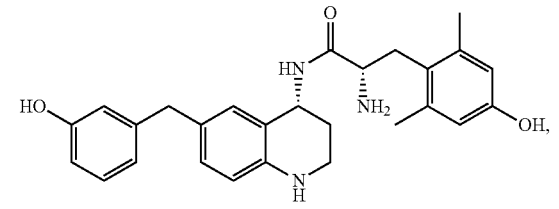
1084
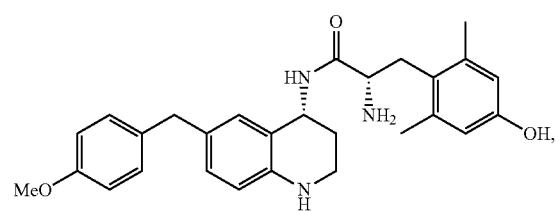
1085
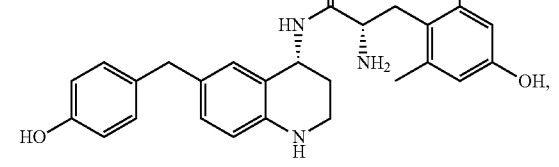
1086
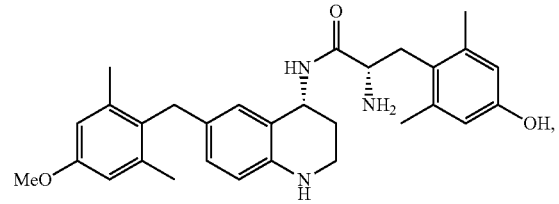
1087
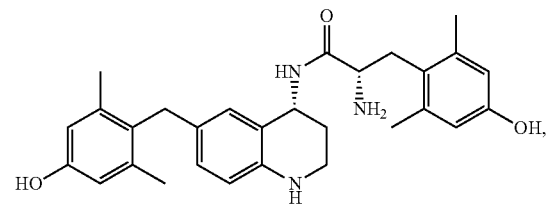
1088
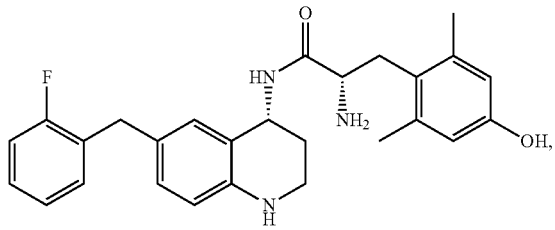
1089
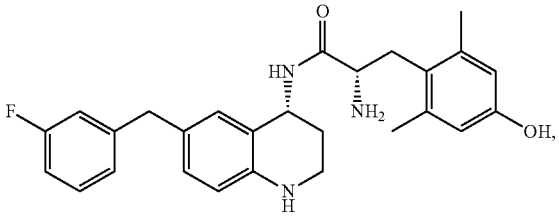
1090
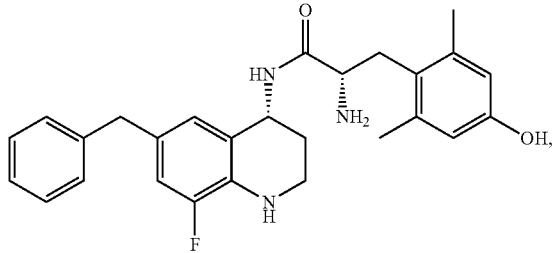
1091
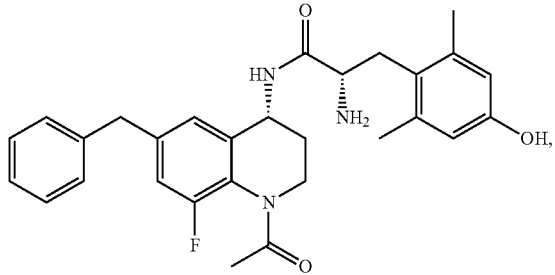
1092
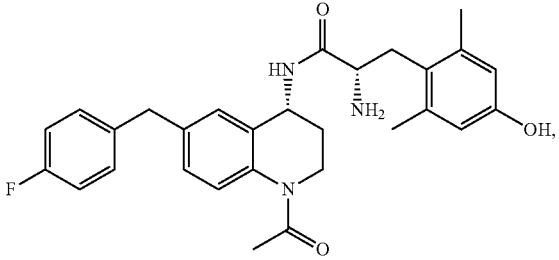

1093
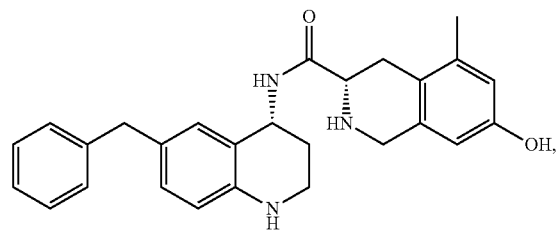
1094
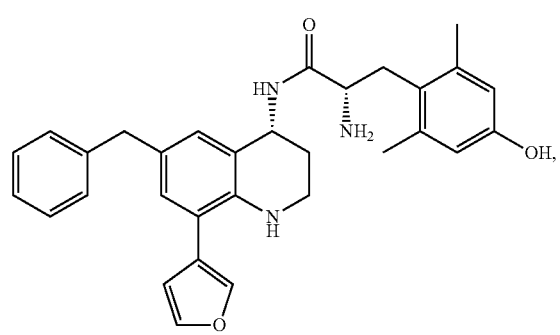
1095
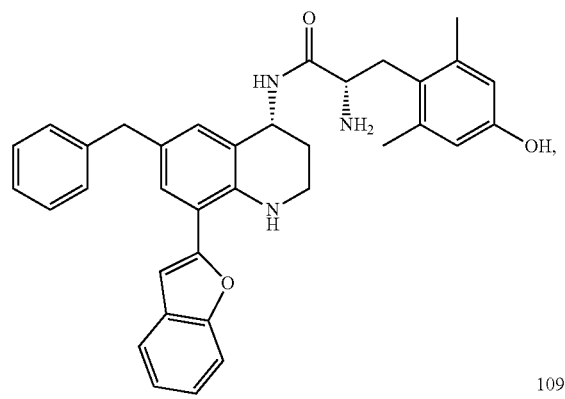
1096
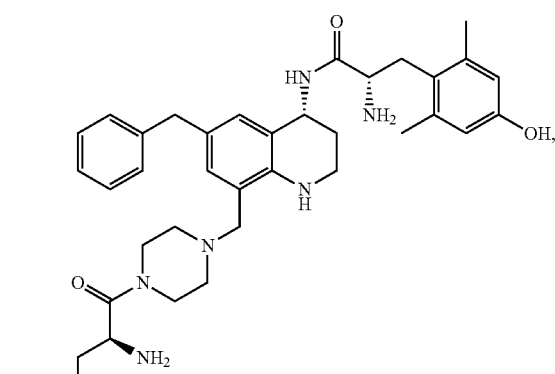
1097
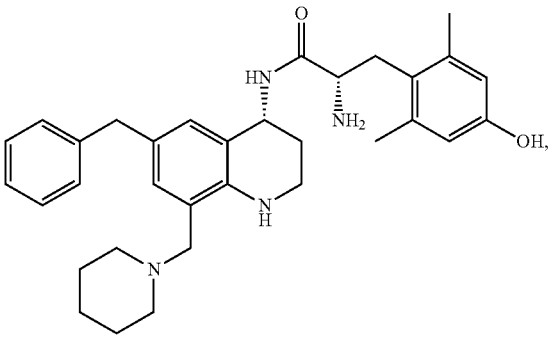
1098
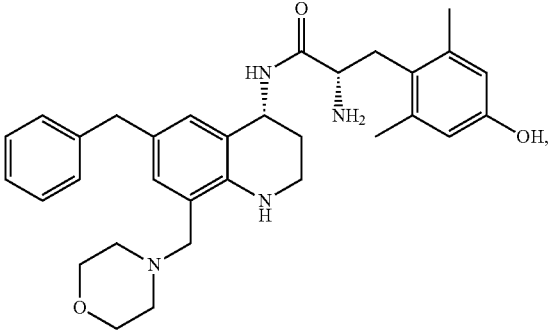
1099
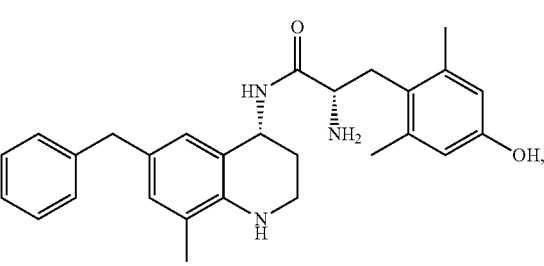
1100

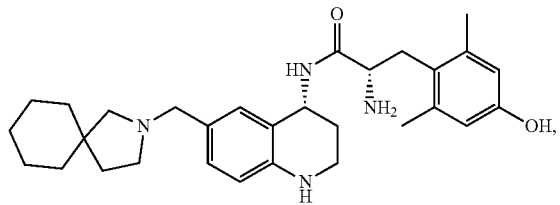
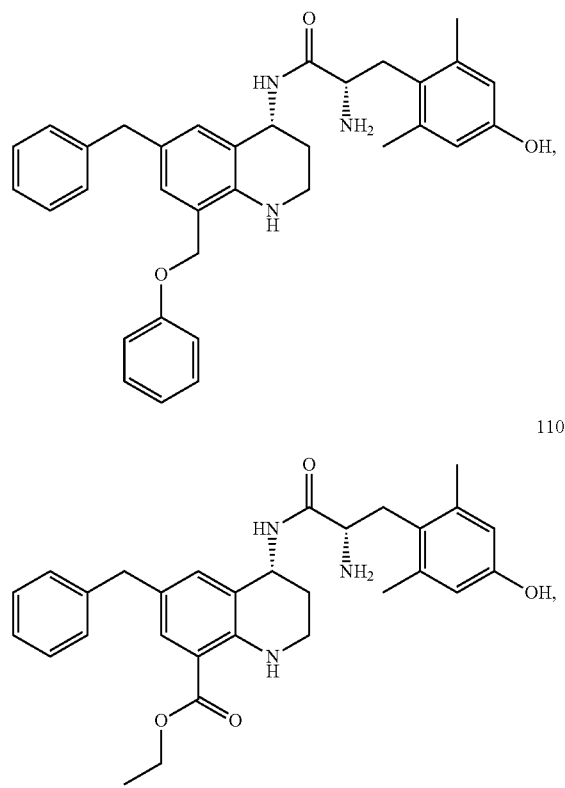
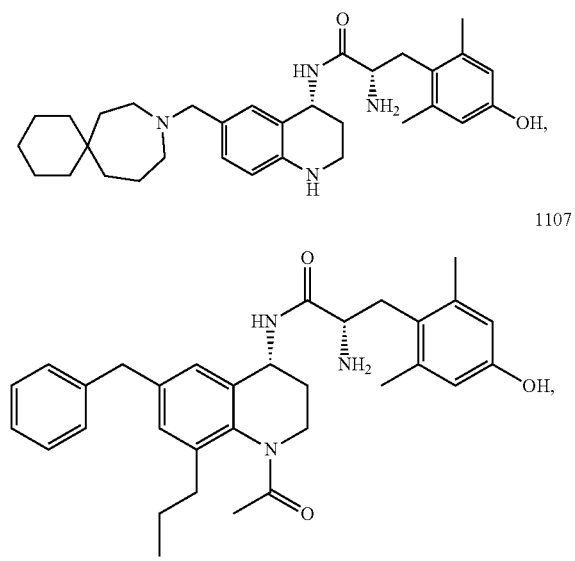
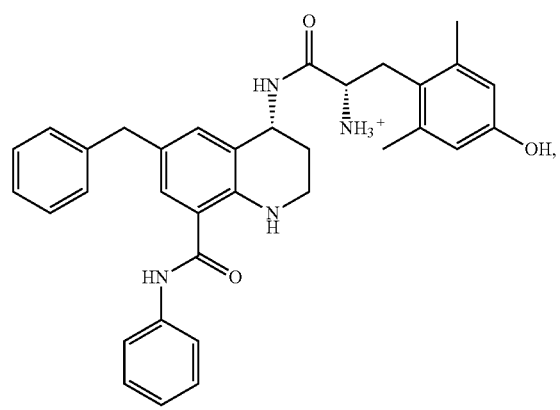
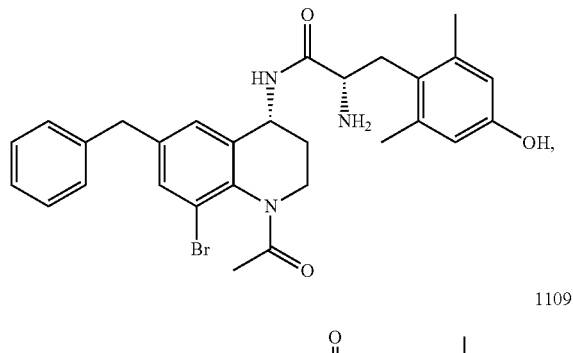
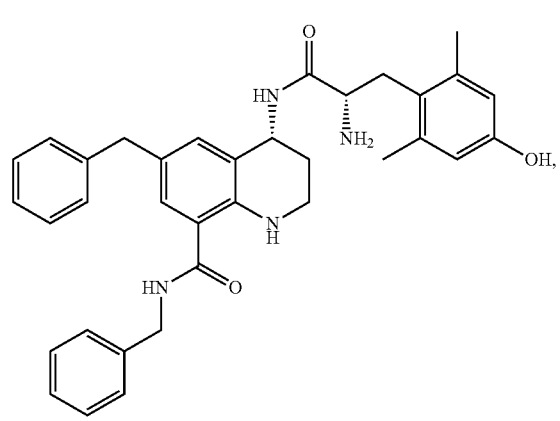
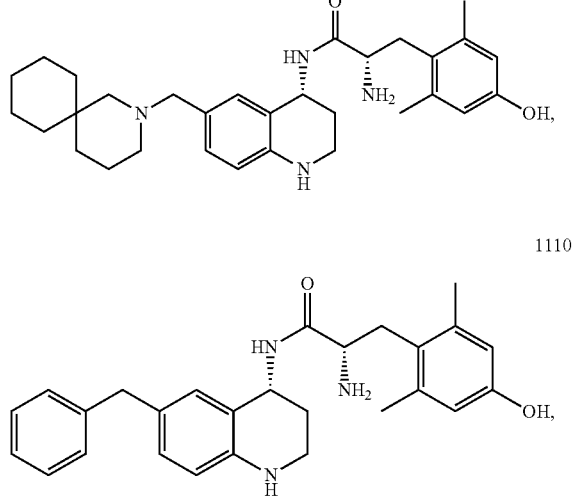

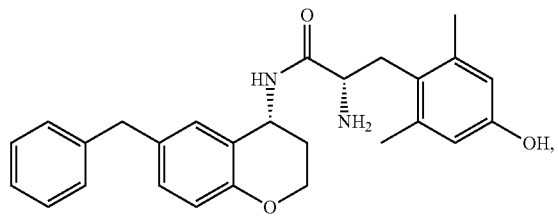
1111
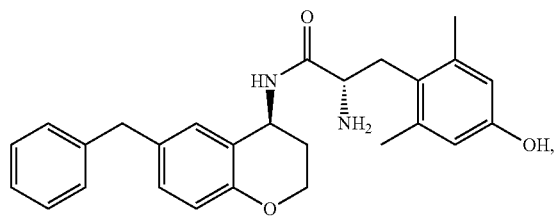
1112
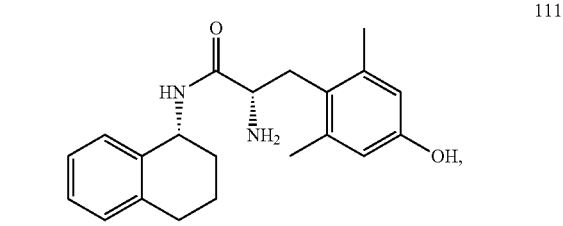
1113
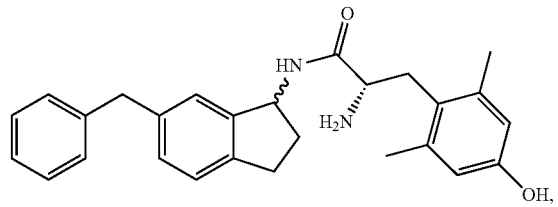
1114
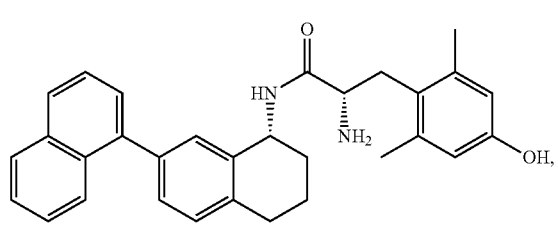
1115
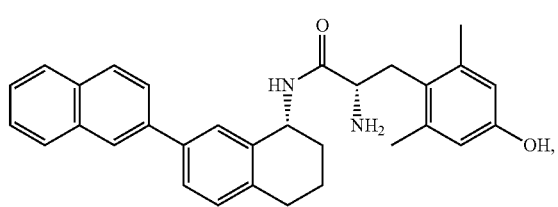
1116
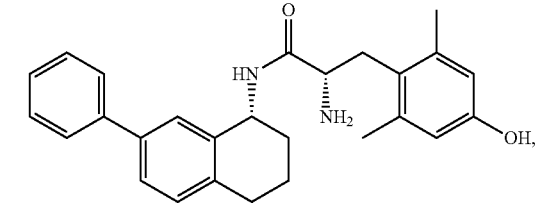
1117
1118
1119
1120
1121
1122
1123

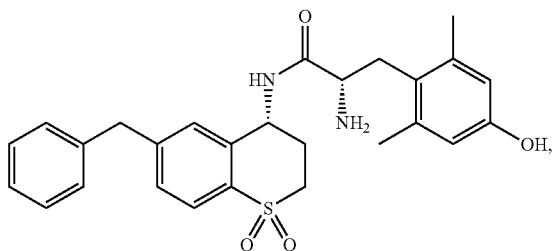

1124

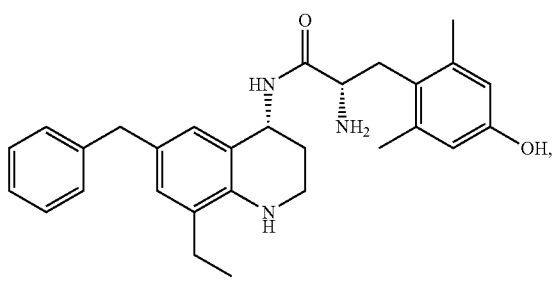

1127

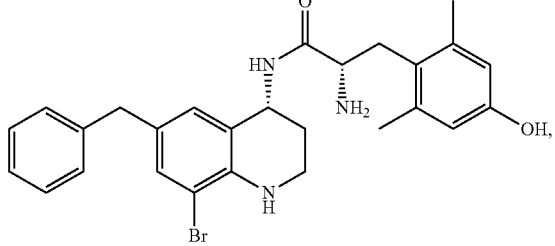

1128

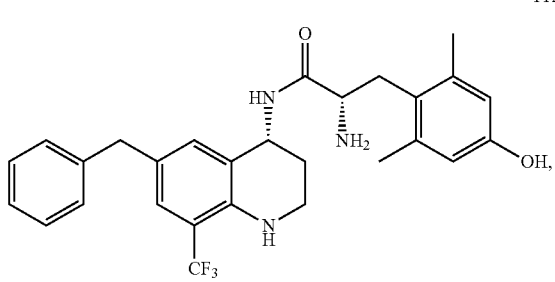

1129

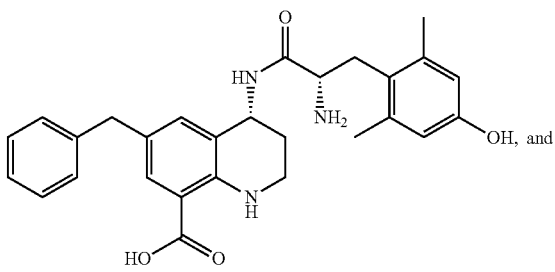

1130

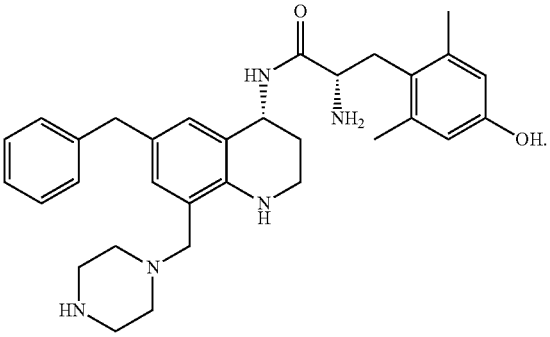

1131

Synthesis of compounds of Formula (I)

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5$^{th}$ edition, John Wiley & Sons: New York, 2001 and Greene, T.W., Wuts, P.G. M., Protective Groups in Organic Synthesis, 3$^{rd}$ edition, John Wiley & Sons: New York, 1999, are useful and recognized reference textbooks of organic synthesis known to those in the art. For example, the compounds disclosed herein can be synthesized by solid phase synthesis techniques including those described in Merrifield, J. Am. Chem. Soc. 1963; 85:2149; Davis et al., Biochem. Intl. 1985; 10:394-414; Larsen et al., J. Am. Chem. Soc. 1993; 115: 6247; Smith et al., J. Peptide Protein Res. 1994; 44: 183; O'Donnell et al., J. Am. Chem. Soc. 1996; 118:6070; Stewart and Young, Solid Phase Peptide Synthesis, Freeman (1969); Finn et al., The Proteins, 3rd ed., vol. 2, pp. 105-253 (1976); and Erickson et al., The Proteins, 3rd ed., vol. 2, pp. 257-527 (1976). The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, ester or prodrug thereof.

In general, the compounds of Formula (I) can be synthesized according to Scheme 1.

Scheme 1

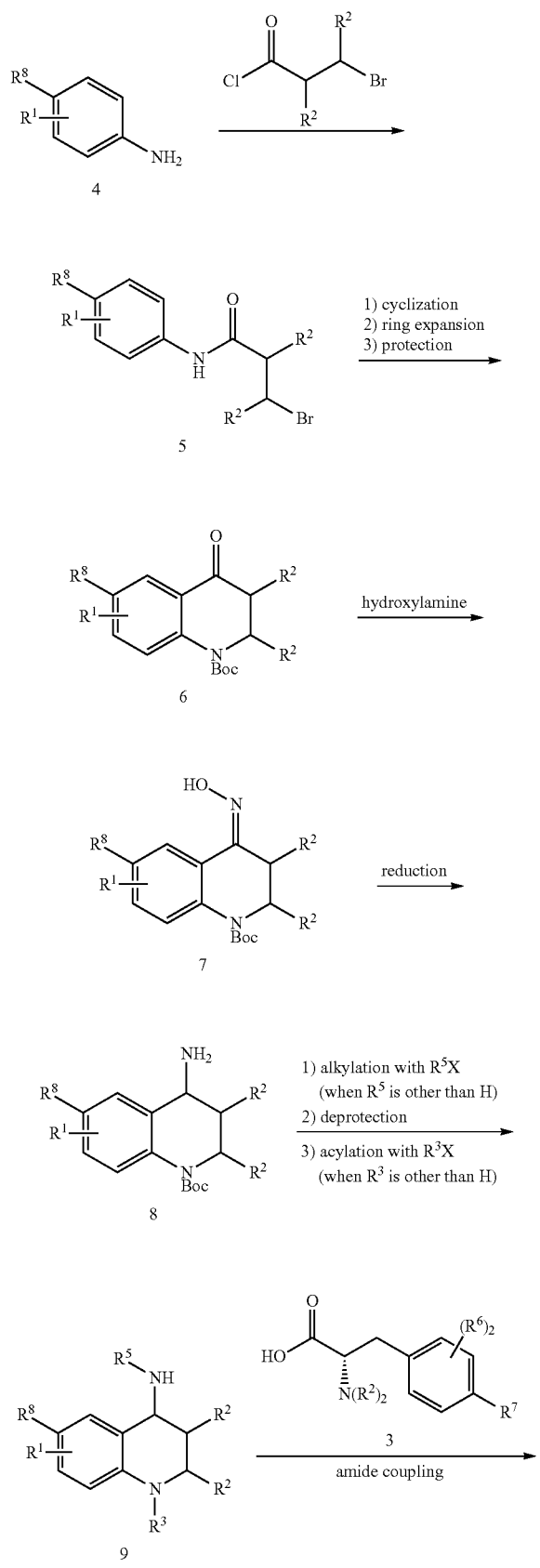

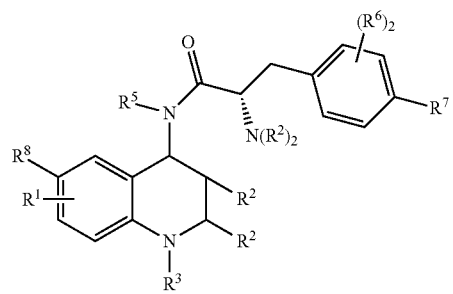

Amines 9 can be synthesized using the procedure shown in Scheme 1. Acylation of substituted anilines 4 with an optionally substituted acyl chloride produces 5. Subsequent intramolecular cyclization and acid-catalyzed ring expansion gives ketones 6. Reductive amination via oxime intermediates 7 produces amines 8. Optional alkylation of the aliphatic amine, optionally followed by acylation or alkylation of the aromatic amine, can produce 9, which can be coupled with 3 to produce compounds as described herein. For this and all other synthetic schemes in this application, X is defined as any suitable leaving group, for example, Cl, Br, I, OTf, or OMs.

Amino acids 3 can be synthesized using procedures such as the one shown in Scheme 2.

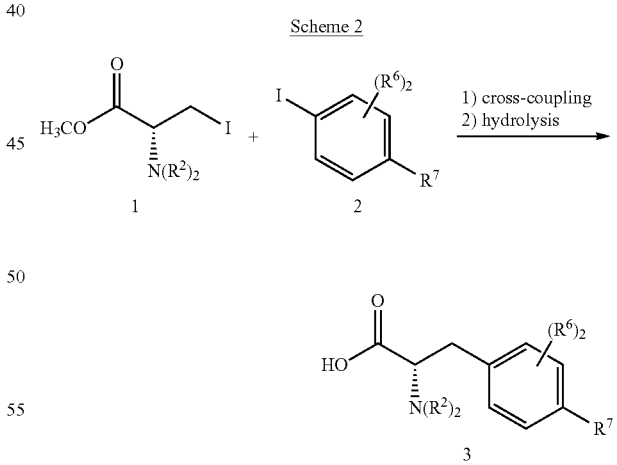

Protected, halogenated amino esters 1 may be cross-coupled, with a metal catalyst and optionally a ligand, to halogenated, substituted aryl groups 2 and subsequently hydrolyzed to produce amino acids 3.

Specific stereoisomers of compound 8 (designated 8') can be obtained as shown in Scheme 3.

Scheme 3

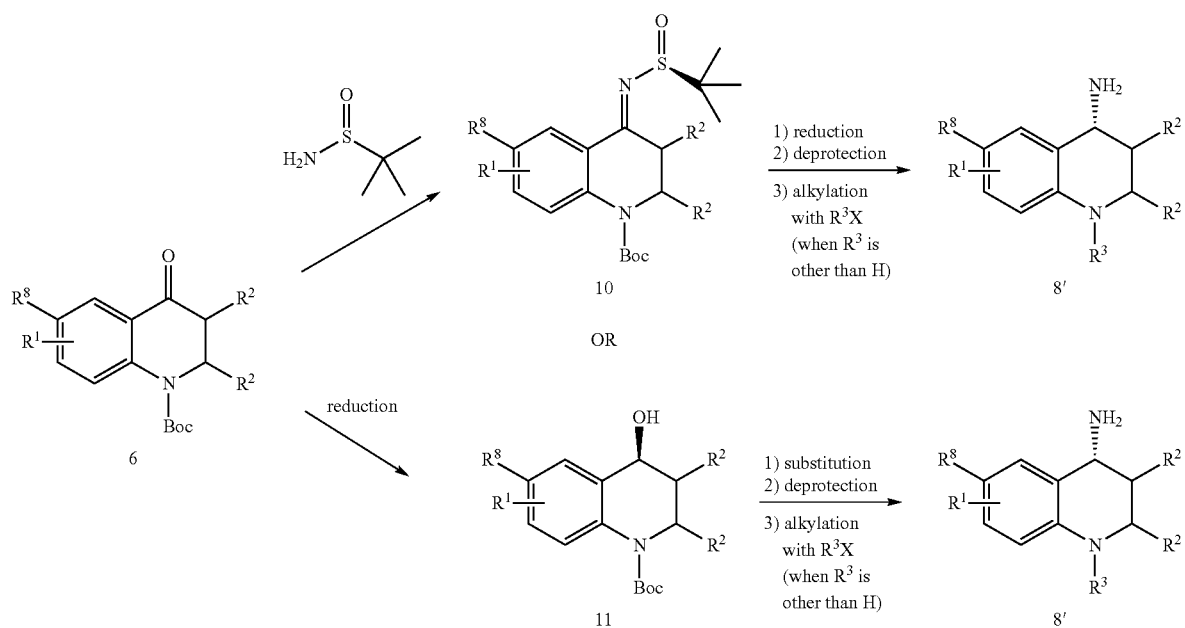

Scheme 3 provides two different pathways for obtaining compound 8'. In the first pathway, compound 6 is treated with tert-butanesulfinamide to produce 10. Reduction and deprotection of 10 gives 8'. In the second pathway, ketone 6 can be asymmetrically reduced using a chiral reducing agent, such as CBS oxazaborolidine, to provide chiral alcohol 11. Alcohol 11 can then be converted to the desired amino group using phthalimide under Mitsunobu conditions. Subsequent deprotection provides 8'. Compound 8' may then be processed in a manner similar to 8 to obtain compounds as described herein.

In some cases, compounds of Formula (I) can be synthesized according to Scheme 4

Scheme 4

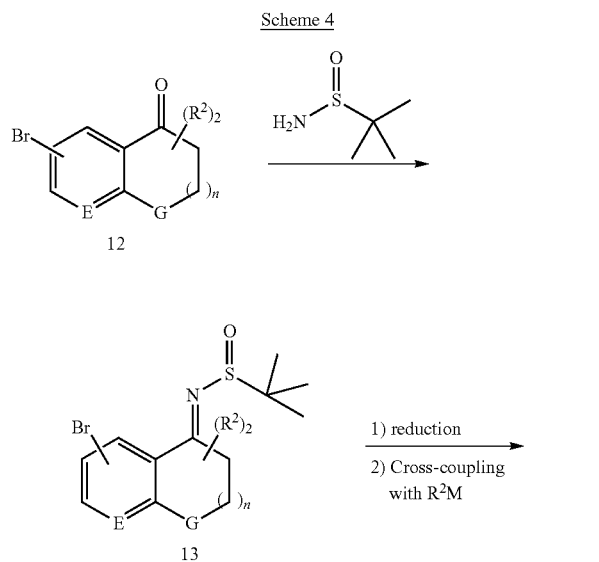

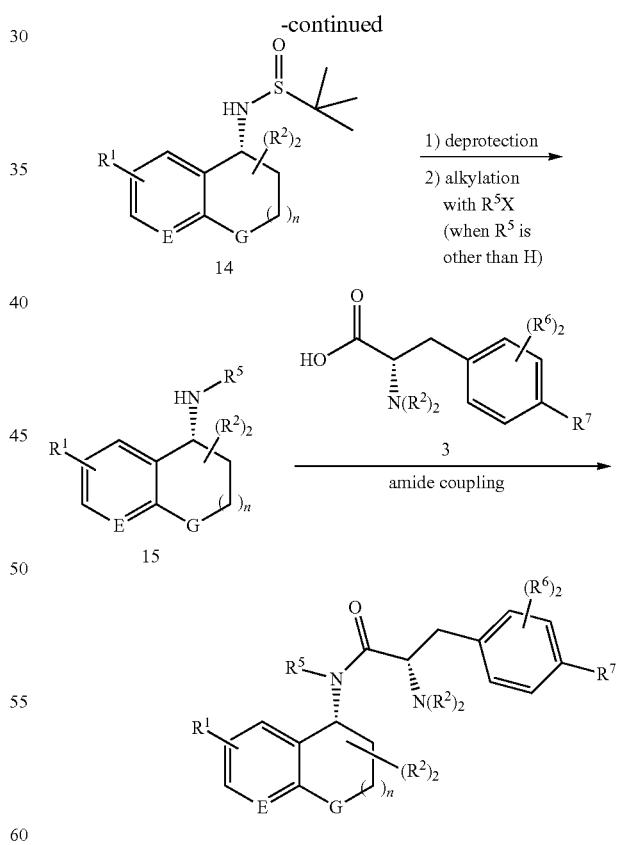

Commercially available bromide 12 can be treated with tert-butylsulfinamide to produce 13. Reduction and subsequent cross-coupling can produce compound 14. In this scheme, M can be any metal or metalloid that is suitable for cross-coupling, e.g., $B(OH)_2$, $SnBu_3$, $ZnBr$, or $SiEt_3$. Deprotection of the aliphatic amine followed by optional alkylation furnishes 15. Amide coupling with 3 can produce compounds as disclosed herein.

Additional synthetic procedures for preparing the compounds disclosed herein can be found in the Examples section.

Pharmaceutical Formulations, Dosing, and Routes of Administration

Further provided are pharmaceutical formulations comprising a compound as described herein (e.g., compounds of Formula (I), or pharmaceutically acceptable salts thereof) and a pharmaceutically acceptable excipient.

The compounds described herein can be administered to a subject in a therapeutically effective amount (e.g., in an amount sufficient to induce analgesia, meaning to reduce, ease, suppress, or alleviate pain). The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the disclosure should be sufficient to effect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

Purely by way of illustration, the method comprises administering, e.g., from about 0.1 mg/kg up to about 100 mg/kg of compound or more, depending on the factors mentioned above. In other embodiments, the dosage ranges from 1 mg/kg up to about 100 mg/kg; or 5 mg/kg up to about 100 mg/kg; or 10 mg/kg up to about 100 mg/kg. Some conditions require prolonged treatment, which may or may not entail administering lower doses of compound over multiple administrations. If desired, a dose of the compound is administered as two, three, four, five, six or more sub-doses administered separately at appropriate intervals throughout the day, optionally, in unit dosage forms. The treatment period will depend on the particular condition and type of pain, and may last one day to several months.

Suitable methods of administering a physiologically-acceptable composition, such as a pharmaceutical composition comprising the compounds disclosed herein (e.g., compounds of Formula (I)), are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the compound is administered regionally via intrathecal administration, intracerebral (intra-parenchymal) administration, intracerebroventricular administration, or intraarterial or intravenous administration feeding the region of interest. Alternatively, the composition is administered locally via implantation of a membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

To facilitate administration, the compound is, in various aspects, formulated into a physiologically-acceptable composition comprising a carrier (e.g., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers, eds., pages 238-250 (1982), and ASHP Handbook on Injectable Drugs, Toissel, 4th ed., pages 622-630 (1986)). A pharmaceutical composition comprising the compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

When appropriate, the compound is administered in combination with other substances (e.g., therapeutics) and/or other therapeutic modalities to achieve an additional (or augmented) biological effect. These other therapeutics/co-treatments include, for example, surgery, radiation treatment, chemotherapy, anti-angiogenic factors (for instance, soluble growth factor receptors (e.g., sflt), growth factor antagonists (e.g., angiotensin), etc.), antibiotics, hormone therapy, anti-inflammatory agents (e.g., Non-Steroidal Anti-Inflammatory Drugs (NSAIDs) or steroidal anti-inflammatory substances), antiviral agents, anti-bacterial agents, cough suppressant, decongestant, or expectorant, pain relievers, and the like. Optionally, the compound is administered in combination with an agent that facilitates transport across the blood-brain barrier and/or an agent that blocks efflux from the brain. Additional combination therapies not specifically listed herein are also within the scope of the present disclosure.

The disclosure thus includes administering to a subject the compound in combination with one or more additionally suitable substances(s), each being administered according to a regimen suitable for that medicament. This aspect includes concurrent administration (e.g., substantially simultaneous administration) and non-concurrent administration (e.g., administration at different times, in any order, whether overlapping or not) of the agent and one or more additionally suitable agents(s). It will be appreciated that different components are, in certain aspects, administered in the same or in separate compositions, and by the same or different routes of administration.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds described herein (e.g., the compounds of Formula (I)) can act as opioid receptor modulators. In some embodiments, the compounds are MOR agonists, e.g., the compounds trigger or upregulate MOR-mediated biological activity, such as analgesia. In various embodiments, the compounds are DOR antagonists, e.g., the compounds inhibit or prevent one or more of DOR's biological activities (such as development of dependence, gastrointestinal motility, or cardiovascular regulation) in response to a DOR agonist. The compounds also can act as dual opioid receptor modulators, which are able to bind MOR and DOR, optionally demonstrating substantially equivalent binding affinity for both receptors. In various embodiments, the compounds are KOR agonists. In some cases, the compounds are KOR antagonists. In some embodiments, the compounds modulate one or more of KOR's biological activities, such as depression, anxiety, analgesia, tolerance, dysphoria, and memory regulation. The compounds can also act as dual MOR/KOR modulators, dual DOR/KOR modulators, or MOR/DOR/KOR triplet modulators.

The compounds disclosed herein are particularly advantageous for the treatment of pain requiring long term administration of opioid receptor agonists, which is connected to an increased risk of adverse side effects. The incidence and/or intensity of adverse side effects associated with opioid use are attenuated with use of the compounds compared to monofunctional opioids, such as morphine. Examples of adverse excitatory effects include, without limitation, physical or psychological dependence, psychological dependence, tolerance, constipation, nausea, respiratory depression, sedation, and vomiting. Physical dependence is marked by physiologic adaptation to a drug that may ultimately lead to withdrawal symptoms when the drug is discontinued. "Tolerance" refers to circumstances where dosage must be increased in order to maintain the physiological response to the agonist achieved at the beginning of treatment.

In some cases, the compounds described herein target the MOR with an $EC_{50}$ in a range of about 0.1 to 3000 nM, 0.1 to 1000 nM, 0.1 to 500 nM, 0.1 to 100 nM, 0.1 to 50 nM, 0.1 to 25 nM, 0.1 to 10 nM, 0.1 to 5 nM, 0.1 to 1 nM, 0.1 to 0.5 nM, 1000 to 2000 nM, 100 to 1000 nM, 10 or 100 nM, 5 to 50 nM, or 1 to 10 nM. These compounds can also target the DOR with an $EC_{50}$ of at least 10 nM, or at least 20 nM, or at least 50 nM, or at least 100 nM, or in a range of about 10 to 1000 nM, 20 to 1000 nM, 50 to 1000 nM, 100 to 1000 nM, or 200 to 1000 nM. These compounds can also bind to, but not stimulate, DOR (e.g., act as an antagonist). These compounds can also target the KOR with an $EC_{50}$ of 5 to 3000 nM, 5 to 1000 nM, 5 to 500 nM, or 5 to 100 nM. When the compounds disclosed herein are dual modulators, their binding affinities can optionally be "substantially equivalent" (e.g., differing by no more than 10-fold or no more than 5-fold)" ". The compounds also, in various embodiments, can selectively bind MOR and DOR, exhibiting decreased affinity for kappa-opioid receptor (KOR). In this regard, the compounds optionally bind MOR and DOR with a binding affinity at least 100 times (e.g., at least 250 times, at least 300 times, at least 400 times, or at least 500 times) greater than the compound binds KOR.

Thus, provided herein is a method of modulating MOR, DOR, and/or KOR, in a cell, comprising contacting the cell with a compound or a composition as disclosed herein (e.g., the compounds of formula (I) in an amount sufficient to modulate MOR, DOR, and/or KOR. In some embodiments, the MOR is modulated alone. In various embodiments, the DOR is modulated alone. In some cases, the KOR is modulated alone. In various cases, the MOR and DOR are modulated simultaneously. In some embodiments, the MOR and KOR are modulated simultaneously. In some cases, the DOR and KOR are modulated simultaneously. In various cases, the MOR, DOR, and KOR are modulated simultaneously. The contacting of the cell can occur in vitro or in vivo. In some cases, contacting of the cell occurs in vitro. In other cases, contacting of the cell occurs in vivo. The compounds described herein can contact a cell in vivo by administering a compound described herein to a subject in need of MOR and/or DOR modulation. Therefore, the disclosure includes administering one or more of a compound described herein to a subject, such as a human, in need thereof. In some embodiments, the subject suffers from pain. The pain can be associated with a disorder of the MOR, DOR, and/or KOR. Disorders associated with MOR include, but are not limited to, pain and gastrointestinal motility disorders (e.g., constipation and irritable bowel syndrome). Disorders associated with DOR include, but are not limited to, seizures and depression. Disorders associated with KOR include, but are not limited to, cocaine dependence. See, e.g., Jutkiewicz et al., J. Pharmacol. Exp. Ther. 2006; 317(3): 1337-48; Clapp et al. Am. J. Obstet. Gynecol. 1998; 178(2):397-401; Nielsen et al., Biol Psychiatry. 2008; 64(11):974-81; and Hubbell et al., Experimental and Clinical Psychopharmacology 1995; 3(2): 123-128.

"Pain" is generally described in terms of duration, cause, and/or afflicted region of the body. The disclosure includes treatment of any type of pain, including neuropathic pain and nociceptive pain. Additional examples of pain include, but are not limited to, visceral pain, muscle pain, inflammatory pain, colicky pain, referred pain, and idiopathic pain. The method further includes treatment of, e.g., long term persistent pain, chronic pain, breakthrough pain, subacute pain, and acute pain. Acute pain is generally a self-limiting physiological response to a discrete bodily insult (e.g., inflammation, surgery, bone fracture, headache, sprain, strains, burn, or chemical exposure). Chronic pain persists longer than would be expected for healing from a discrete bodily insult, and includes disorders such as, e.g., back pain, myofascial pain, arthritis, cancer pain, neuropathic pain, and fibromyalgia.

Efficacy in treating (e.g., reducing, easing, suppressing, or alleviating) pain in a subject in need thereof is determined using any suitable method. Analgesic efficacy is measured, for example, using a nociception assay in animals such as a tail withdrawal test, pain relief score, or a pain intensity difference score, optionally recorded at a given time point, or over time, or as compared to a baseline, and includes calculations based on area under the curve such as those plotting Total Pain Relief Score (TOTPAR) or the Sum of Pain Intensity Difference (SPID), as described in the Handbook of Pain Assessment, 2d. Turk & Meldzack, Eds., The Guilford Press, New York, N.Y. (2001). Increases in time to re-medication and increases in quality of life measurements also are indicators of successful pain treatment.

"Treating" pain or an opioid receptor-associated disorder does not require a 100% abolition of pain or the disorder. Any decrease in pain sensation or symptoms of the disorder constitutes a beneficial biological effect in a subject. In this regard, the disclosure reduces pain or the symptoms of a MOR associated disorder and/or a DOR associated disorder by, e.g., at least about 5%, at least about 10% or at least about 20% compared to levels of, e.g., pain observed in the absence of the method (e.g., in a biologically-matched control subject, subject that is not administered the compound, or the subject administered the compound prior to treatment). In some embodiments, pain is reduced by at least about 30%, at least about 40%, at least about 50%, or at least about 60%. In some embodiments, the method inhibits pain by at least about 70%, at least about 80%, at least about 90%, or more (about 100%) compared to that experienced in the absence of the method Further provided is a method of treating a subject suffering from pain, comprising administering to the subject a therapeutically effective amount of a compound or a composition as disclosed herein. In some cases, the pain is associated with a disease or condition selected from gastrointestinal motility disorders (e.g., constipation), seizures, depression, and cocaine dependence. In some embodiments, the method of treating pain is associated with a decreased risk of developing tolerance and dependence.

In various cases, the subject is a mammal. In some cases, the subject is human.

MOR agonism, DOR antagonism, and KOR agonism can be determined using any suitable assay, including assays that detect up- or down-regulation of G protein mediated signal transduction pathways associated with the opioid receptors. An exemplary assay is described in the Example, and entails measurement of radiolabeled GTP analogs produced by activated G proteins. Agonism is generally described in terms of potency, e.g., the concentration of compound required to achieve a 50% increase in G protein activity (and, by extension, opioid receptor activity). Agonism also generally described in terms of efficacy, e.g., the maximum level of G protein activity triggered by the compound. Efficacy often is reported as a percentage of the level of activity achieved by a "standard" receptor agonist (for example, DAMGO ([D-Ala$^2$,N-MePhe$^4$,Gly-ol]-enkephalin) for MOR or DPDPE ([D-Pen 2,D-Pen 5]-enkephalin)

for DOR). Optionally, the compound enhances MOR-mediated G protein activation with a half maximal effective concentration ($EC_{50}$) of less than or equal to $1\times10^{-7}$ M, less than or equal to $1\times10^{-8}$ M, less than or equal to $1\times10^{-9}$ M, or less than or equal to $1\times10^{-10}$ M. A compound of Formula (I), in various embodiments, provides at least 10% max. stimulation of MOR (e.g., at least 15%, at least 20%, at least 25%, at least 30%, at least 35%, at least 40%, at least 50%, at least 55%, or at least 60% max. stimulation of MOR) in the [$^{35}$S]GTPγS stimulation assay described in the Example. In one aspect, the compound exhibits MOR agonism efficacy similar to that of morphine (e.g., the compound's % max. in the [$^{35}$S]GTPγS stimulation assay described in the Example is within 10% of the % max. calculated for morphine). Optionally, the compound is more potent at MOR-coupled G protein stimulation than morphine and/or endomorphin (e.g., 10-fold, 20-fold, 30-fold, or 40-fold more potent than morphine measured using the [3'5'$^{35}$S]GTPγS stimulation assay described in the Example). A DOR antagonist does not activate G proteins itself and inhibits G protein activation by at least one DOR agonist. A DOR antagonist also preferably counteracts (e.g., reverses, lessens, or prevents) DOR agonist-mediated inhibition of forskolin-stimulated adenylyl cyclase.

Uses of the compounds of Formula (I) in the preparation of a medicament for treating pain, and to treat pain (e.g., as an analgesic) also are disclosed herein.

The disclosure herein will be understood more readily by reference to the following examples, below.

EXAMPLES

The following examples are provided for illustration and are not intended to limit the scope of the disclosure.

Synthetic Procedures for Compounds of Formula (I)

General Experimental Procedures. All reagents and solvents were obtained from commercial sources and used without additional purification. To prepare $P_2O_5/Al_2O_3$ (w/w 50%), $Al_2O_3$ was placed in an oven at 120° C. for 24 h. After it reached room temperature in a desiccator, $P_2O_5$ was added in equal amounts. The compounds were mixed and returned to the desiccator for later use. Suzuki couplings were performed on a Discover S-class (CEM) microwave in a closed vessel with maximum power input of 300 W and temperature set at 110° C. for 10 min under the standard method from their Synergy software. Hydrogenations were performed on a Parr hydrogenator apparatus from Parr Instrument Company, model 3916EA, at the pressures specified using 10% Pd/C as the catalyst. Flash column chromatography was carried out using P60 silica gel (230-400 mesh). Purification of final compounds was performed using a Waters semipreparative HPLC with a Vydac protein and peptide C18 reverse phase column, using a linear gradient of 15% solvent B (0.1% TFA in acetonitrile) in solvent A (0.1% TFA in water) to 50% solvent B in solvent A at a rate of either 0.5% or 1% per minute and monitoring UV absorbance at 230 nm. Purity of synthesized compounds was determined on a Waters Alliance 2690 analytical HPLC instrument and a Vydac protein and peptide $C_{18}$ reverse phase column, using a linear gradient of 0% solvent B in solvent A to 45%, 70%, or 90% solvent B in solvent A in 45, 70, or 90 min, respectively, and UV absorbance at 230 nm (gradient A). Purities of the final compounds used for testing were ≥95% as determined by HPLC. $^1$H NMR and $^{13}$C NMR data were obtained on either a 400 or 500 MHz Varian spectrometer using $CDCl_3$ or $CD_3OD$ solvents. The identity of each compound was verified by mass spectrometry using an Agilent 6130 LC-MS mass spectrometer in positive mode.

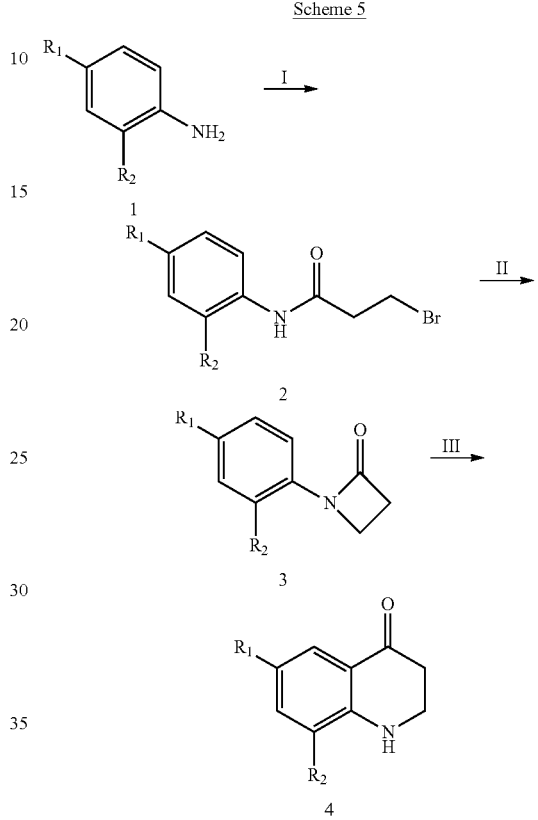

| | | | |
|---|---|---|---|
| 4a | $R_1$ = Bn | $R_2$ = H | |
| 4b | $R_1$ = H | $R_2$ = Me | |
| 4c | $R_1$ = Br | $R_2$ = Et | |
| 4d | $R_1$ = H | $R_2$ = n-Pr | |
| 4e | $R_1$ = H | $R_2$ = n-Bu | |
| 4f | $R_1$ = H | $R_2$ = t-Bu | |
| 4g | $R_1$ = Br | $R_2$ = F | |
| 4h | $R_1$ = H | $R_2$ = $CF_3$ | |

Scheme 1. Synthesis of intermediates 4a-h from substituted anilines 1a-h (i) 3-bromopropionyl chloride, $K_2CO_3$; (ii) sodium tert-butoxide; (iii) trifluoromethanesulfonic acid General Procedure (i) for Acylation of Anilines 1a-h (Scheme 5)

To a flame-dried round-bottom flask under inert atmosphere was added aniline (1.00 equiv.), followed by dichloromethane (200 mL), then $K_2CO_3$ (1.30 equiv.). After 10 minutes, 3-bromopropionyl chloride (1.1 equiv.) was added slowly via syringe. Reaction was monitored by TLC in 40% ethyl acetate, 60% hexanes. Ninhydrin stain was used to help monitor disappearance of aniline starting material. After 3 hours, reaction was quenched with deionized water.

Organics were separated and dried over MgSO$_4$, then filtered and concentrated under vacuum. Product was used without further purification.

General Procedure (ii) for Cyclization of Intermediates 2a-h

To a flame-dried round-bottom flask under inert atmosphere was added sodium tert-butoxide (1.1 equiv.), then suspended in DMF (60 mL) and stirred 10 min before slowly adding a solution of intermediate 2a-h dissolved in DMF (60 mL) at ambient temperature via syringe. Monitored reaction by TLC, in 40% ethyl acetate, 60% hexanes. Desired product showed a moderate decrease in Rf relative to starting material. After stirring 1 hour, reaction mixture was concentrated under vacuum, then resuspended in dichloromethane. Extracted reaction mixture with deionized water and aqueous sodium bicarbonate, then separated organics and dried over MgSO$_4$. Filtered and reconcentrated organics onto silica, then purified by flash chromatography.

General Procedure (iii) for Fries Rearrangement of Intermediates 3a-h (afn-iv-115)

To a round-bottom flask containing intermediate 3a-h (1 equiv.) dissolved in dichloroethane (170 mL) under inert atmosphere was added TfOH (3 equiv.) slowly. After 1 hour, TLC in 40% ethyl acetate, 60% hexanes showed a decrease in Rf. Reaction was quenched with deionized water, then diluted with dichloromethane. Acidified to pH 1 with HCl, then separated organics and dried over MgSO$_4$. Filtered and concentrated organics onto silica and purified by flash chromatography.

Scheme 6

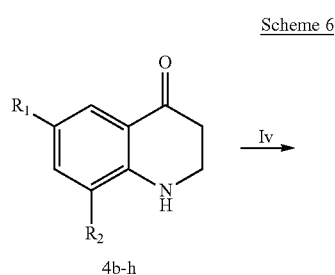
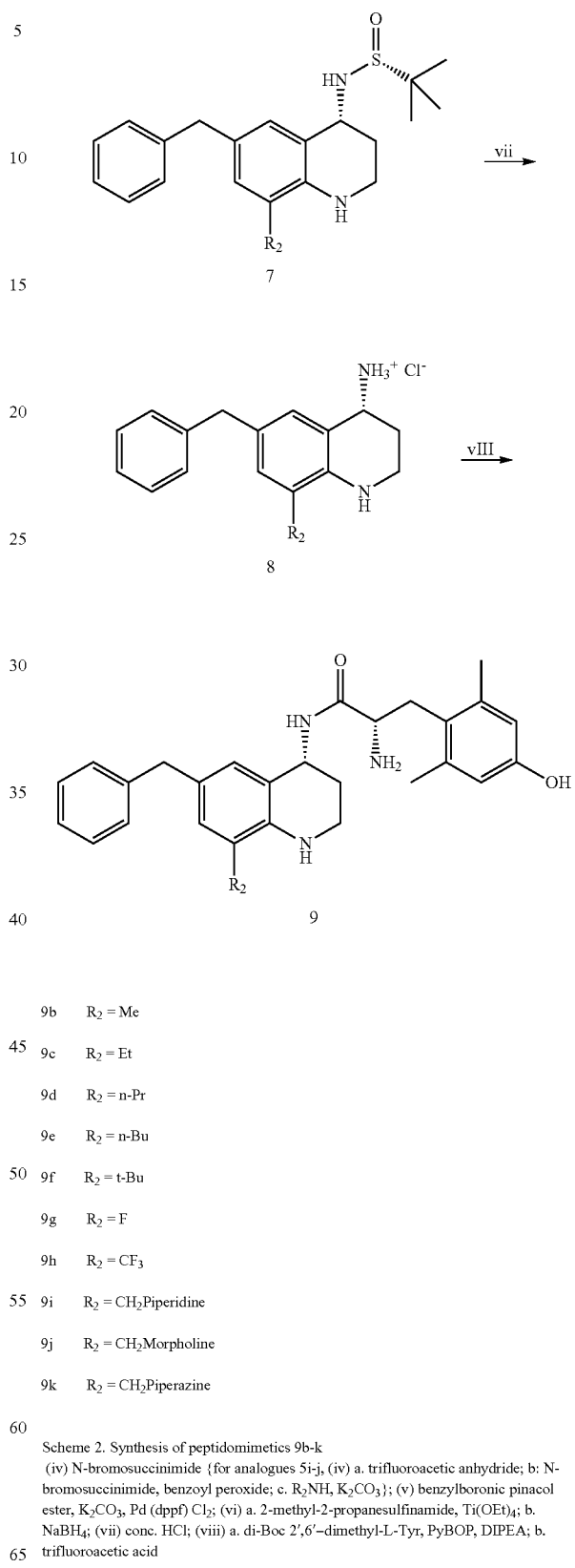

Scheme 2. Synthesis of peptidomimetics 9b-k
(iv) N-bromosuccinimide {for analogues 5i-j, (iv) a. trifluoroacetic anhydride; b: N-bromosuccinimide, benzoyl peroxide; c. R$_2$NH, K$_2$CO$_3$}; (v) benzylboronic pinacol ester, K$_2$CO$_3$, Pd (dppf) Cl$_2$; (vi) a. 2-methyl-2-propanesulfinamide, Ti(OEt)$_4$; b. NaBH$_4$; (vii) conc. HCl; (viii) a. di-Boc 2′,6′-dimethyl-L-Tyr, PyBOP, DIPEA; b. trifluoroacetic acid

Scheme 7

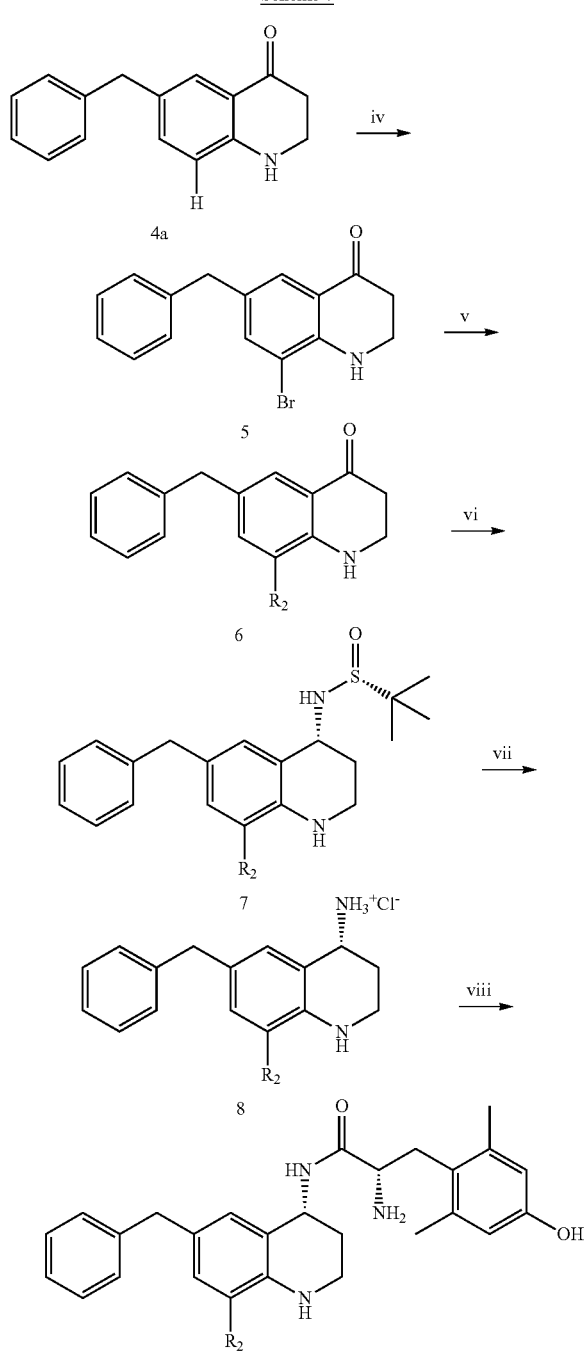

9a R$_2$ = Bn
9l R$_2$ = EtPh
9m R$_2$ = 3-furan
9n R$_2$ = COOEt
9o R$_2$ = CONHPh
9p R$_2$ = CONHBn
9q R$_2$ = Br
9r R$_2$ = COOH Scheme 3. Synthesis of peptidomimetics 9a, l-r from 4a
(iv) N-bromosuccinimide (v) benzyl-, ethylphenyl-, or 3-furanyl-boronic pinacol ester, K$_2$CO$_3$, Pd(dppf)Cl$_2$; {for analogues 6n-p, (v)a. CO, K$_2$CO$_3$, Pd(dppf)Cl$_2$, and MeOH (6n) or H$_2$O (6o, p); b. aniline or benzylamine, Et$_3$N}; (vi)a. 2-methyl-2-propanesulfinamide, Ti(OEt)$_4$; b. NaBH$_4$; (vii) conc. HCl; (viii)a. di-Boc 2',6'-dimethyl-L-Tyr, PyBOP, DIPEA; b. trifluoroacetic acid {for analogue 9r, (viii)b. LiOH, c. TFA}

General Procedure (iv) for Bromination of Intermediates 4a-h (Schemes 6 and 7)

To a round-bottom flask containing intermediates 4a-h (1 equiv.) dissolved in dichloromethane (20 mL) under inert atmosphere was added N-bromosuccinimide (1.05 equiv.) at ambient temperature. After 30 minutes, TLC in 40% ethyl acetate, 60% hexanes showed complete conversion, reaction was reconcentrated onto silica and was purified by flash chromatography.

General Procedure (iv)a. for N-Trifluoroacetyl Protection of Intermediate 5b

To a round-bottom flask containing intermediates 5b (1 equiv.) dissolved in dichloromethane (20 mL) under inert atmosphere was added trifluoroacetic anhydride (2 equiv.) at 0° C. After 4 hours, reaction was reconcentrated onto silica and was purified by flash chromatography, yielding Intermediate 5i.a as a white crystalline solid.

General Procedure (iv)b. for Bromination of Intermediate 5i.a

To a round-bottom flask containing intermediates 5i.a (1 equiv.) under inert atmosphere was added N-bromosuccinimide (1.05 equiv.) and benzoyl peroxide (0.1 equiv.), followed by degassed, Ar-sparged CCl$_4$ (15 mL). Reaction was heated to reflux for 6 hours. Reaction was cooled to −20° C., and precipitate was filtered from solution (washing with additional CCl$_4$ at −20° C.). Filtrate was then reconcentrated onto silica and purified by manually-packed silica column chromatography using 10% ethyl acetate, 90% hexanes, as flash chromatography did not provide sufficient separation. Brominated intermediate 5i.b was isolated as a white crystalline solid.

General Procedure (iv)c. for Substitution of Intermediate 5i.b

To a round-bottom flask containing intermediate 5i.b (1 equiv.) under inert atmosphere was added K$_2$CO$_3$ (2 equiv.) and specified amine (2 equiv.), followed by DMF (5 mL) at ambient temperature. After 12 hours, reaction was reconcentrated onto silica and was purified by flash chromatography.

General Procedure (v) for Suzuki Coupling of Intermediates 5a-k

To a round-bottom flask containing intermediate 5a-k (1 equiv.) under inert atmosphere was added degassed, argon-sparged 3:1 acetone/water (12 mL), followed by Pd(dppf)Cl$_2$ (0.1 equiv.), benzyl boronic acid pinacol ester (2 equiv.), and K$_2$CO$_3$ (3 equiv.), then heated to reflux (85° C.) overnight. After 12 hours, reaction mixture was cooled to ambient temperature and diluted with ethyl acetate and aqueous sodium bicarbonate. Organics were isolated, dried over MgSO$_4$, filtered and reconcentrated onto silica. Crude reaction mixture was purified by flash chromatography.

General Procedure (v)a. for Carbonylation of Intermediate 5a

To a flame-dried glass microwave tube containing degassed 1:1 DMF:MeOH or DMF:H₂O (6 mL) under inert atmosphere was added intermediate 5a (1 equiv.), K₂CO₃ (1.5 equiv.) and Pd(dppf)Cl₂ (0.1 equiv.). To a separate 30 mL pressure tube containing 2M NaOH (15 mL) stirring, with a port from the septum of the pressure tube leading into the reaction solution, was added oxalyl chloride (1 mL total volume). Carbon monoxide generated in situ from the decomposition of oxalyl chloride bubbled through the reaction mixture 10 minutes, with a vent in reaction tube to avoid overpressurizing. Vent was replaced with a balloon filled with CO, and heated at 80° C. for 5 hours. After cooling to ambient temperature, reaction solvents were removed under vacuum and residue was resuspended in ethyl acetate and water at pH 1. Organics were isolated, dried with MgSO₄, filtered, and reconcentrated onto silica. Reaction was purified by flash chromatography.

General Procedure (v)b. for Amide Coupling to Intermediate 6r

To a pear-shaped flask containing intermediate 6r (1.0 equiv.) dissolved in DMF (3 mL) under intert atmosphere was added the coupling reagent PyBOP (1.2 equiv.), specified amine (1.2 equiv.) and DIPEA (excess) and stirred at ambient temperature. After 3 hours, solvent was removed under reduced pressure and reconcentrated residue onto silica. Purified by flash chromatography.

General Procedure (vi) for Transamination of Intermediates 6a-q

To a pear-shaped flask containing intermediates 6a-q (1 equiv.) under inert atmosphere was added (R)-2-methylpropane-2-sulfinamide (3 equiv.), followed by THF (3 mL) at ambient temperature. Reaction mixture was cooled to 0° C. before adding Ti(OEt)₄ (6 equiv.). Upon reaching ambient temperature, reflux condenser under inert atmosphere was affixed and reaction was heated to reflux (85° C.). After 48 hours, reaction was cooled to ambient temperature, then transferred to a round-bottom flask containing NaBH₄ (6 equiv.) under inert atmosphere in THF (3 mL) at −78° C. via syringe. Reaction flask was warmed to ambient temperature, and after 3 hours was quenched with saturated aqeuous NaCl. Reaction mixture was diluted with ethyl acetate and saturated aqeuous ammonium chloride. Organics were isolated and dried over MgSO₄, filtered and concentrated onto silica. Crude reaction mixture was purified by flash chromatography. Product had a much lower Rf than starting material by TLC in 80% ethyl acetate, 20% hexanes.

General Procedure (vii) for Cleavage of Sulfinamide Auxiliary of Intermediates 7a-q To a pear-shaped flask containing intermediates 7a-q (1 equiv.) was added dioxane (15 mL), followed by concentrated HCl (6 equiv.) at ambient temperature. After 1 hour, solvent was removed and residual oil was washed with diethyl ether. Reaction flask was cooled to 0° C., then ether was decanted leaving the amine salt as a white solid. Carried forward without further purification.

General Procedure (viii) for Amide Coupling diBoc-Dmt to Intermediates 8a-q

To a pear-shaped flask under inert atmosphere was added Intermediates 8a-q (1 equiv.), diBoc-Dmt (1.1 equiv.), coupling reagents PyBOP (1.1 equiv.), and 6-Cl HOBt (1.1 equiv.), followed by DMF (10 mL) and DIPEA (10 equiv.) at ambient temperature. After stirring 6 hours, solvent was removed under vacuum and residual oil was loaded onto silica. Boc-protected intermediates were purified by flash chromatography. Isolated Boc-protected product was suspended in DCM (9 mL), and TFA was added (3 mL). After 1 hour, solvent was removed under vacuum and product was resuspended in a solution of 99.9% acetonitrile, 0.1% TFA, then diluted with deionized water. Final products were purified by reverse-phase semi-preparative HPLC.

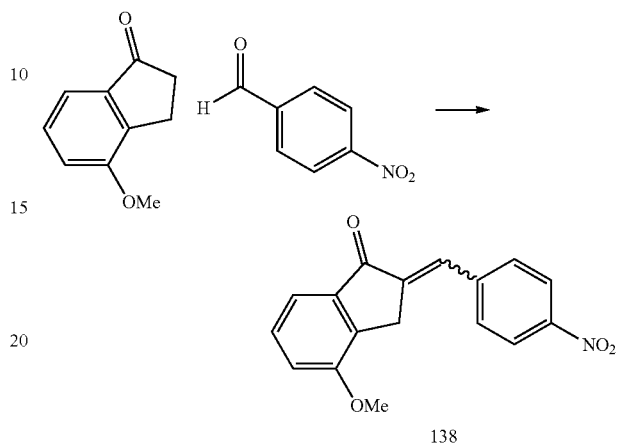

138

4-Methoxy-2-(4-nitrobenzylidene)-2,3-dihydro-1H-inden-1-one (138) To a reaction vessel containing MeOH (375 mL) was added KOH (0.208 g, 3.7 mmol, 1.2 eq). After dissolution, commercially available 4-methoxy-2,3-dihydro-1H-inden-1-one (0.500 g, 3.1 mmol, 1.0 eq) was added and allowed to dissolve. Next, p-nitrobenzaldehyde (0.559 g, 3.7 mmol, 1.2 eq) was added to the reaction mixture and allowed to stir for 1 h. Solvent was removed under reduced pressure and the residual solid was washed with cold H₂O (50 mL) and filtered to yield a homogeneous, mustard yellow powder (0.881 g, 96.8%) as the pure product. No ¹H ¹³C data was collected. Product was taken on to the next step (formation of 141) without additional isolation, purification, or characterization.

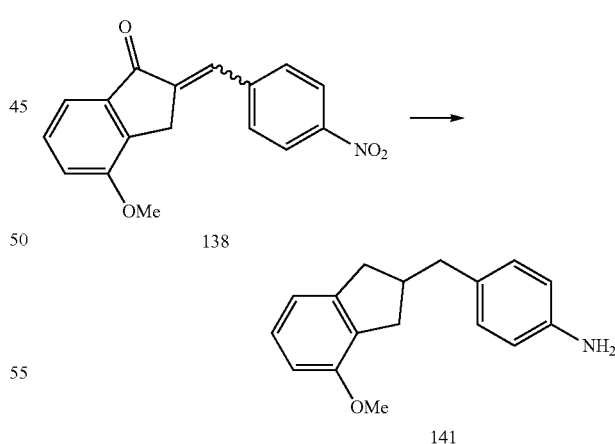

138

141

4-((4-Methoxy-2,3-dihydro-1H-inden-2-yl)methyl)aniline (141) To a hydrogenation vessel was added 10% Pd/C catalyst (1.5 g) followed by the slow addition of MeOH (120 mL). The aldol intermediate 138 (0.881 g, 2.98 mmol, 1.0 eq) was dissolved in minimal MeOH and added to the vessel, followed by concentrated HCl (5.8 mL). The reaction vessel was placed on the hydrogenator under 50 psi of H₂ gas and allowed to shake for 24 h. The reaction mixture was then filtered through a pad of Celite, and solvent was removed under reduced pressure. The crude residue was extracted twice with DCM (150 mL) from 2 M NaOH (200 mL), and the combined organic layers were subsequently washed 2×NaHCO₃ (100 mL), 1× brine (100 mL), dried under MgSO₄, filtered, and concentrated. The crude residue was purified using silica gel chromatography to yield the pure product as a light orange solid (698 mg, 92.3%). Product was characterized by ¹H NMR and ¹³C NMR on a Varian 500 MHz spectrometer in CDCl₃.

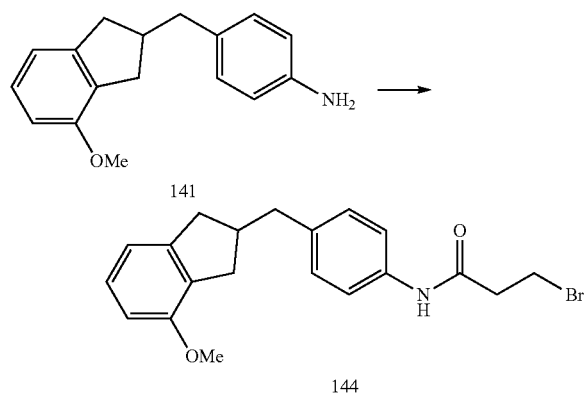

3-Bromo-N-(4-((4-methoxy-2,3-dihydro-1H-inden-2-yl)methyl)phenyl)propanamide (144) To a flame-dried round bottom flask under Ar was added the aniline compound 141 (698 mg, 2.76 mmol, 1.0 eq) and K₂CO₃ (780 mg, 5.65 mmol 2.05 eq). The reaction vessel was placed back under vacuum and anhyd. DCE was added via syringe. The reaction solution stirred under vacuum for 5 min. After 5 min, the reaction vessel was then flooded with Ar and 3-bromopropionyl chloride (0.283 mL, 2.81 mmol, 1.02 eq) was added via syringe. The reaction stirred under Ar at RT for 1 h and was monitored by TLC using a ninhydrin stain for disappearance of aniline compound. Once the reaction was complete, it was quenched with dI H₂O and the layers separated. The organic layer was washed with dI H₂O (1×50 mL) followed by brine (1×30 mL), then dried over MgSO₄, filtered, and concentrated under reduced pressure to yield the pure product as white, waxy solid (997 mg, 93.2%). Product was characterized by ¹H NMR and ¹³C NMR on a Varian 500 MHz spectrometer in CDCl₃.

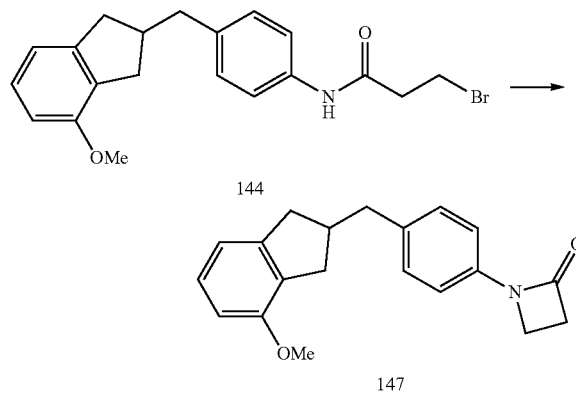

1-(4-((4-Methoxy-2,3-dihydro-1H-inden-2-yl)methyl)phenyl)azetidin-2-one (147) To a round bottom flask already containing the dried, desiccated 3-bromo-N-propanamide (997 mg, 2.57 mmol, 1.0 eq) was added NaOtBu (259 mg, 2.70 mmol, 1.05 eq). The reaction vessel was placed under vacuum and anhyd. DMF was added via syringe. The solution stirred under vacuum for 5 min, and then was flooded with Ar. The reaction stirred under Ar at RT for up to 3 h and was monitored by TLC. Once complete, the solvent was removed under reduced pressure and the resulting crude residue was re-suspended in DCM and dI H₂O, and the layers separated. The organic layer was washed once with dI H₂O (1×30 mL), then brine (1×30 mL), then dried over MgSO₄, filtered, and concentrated under reduced pressure to yield the crude product, which was then purified using silica gel chromatography to yield the pure product as a brown oil (789 mg, quant.). Product was characterized by ¹H NMR and ¹³C NMR on a Varian 500 MHz spectrometer in CDCl₃.

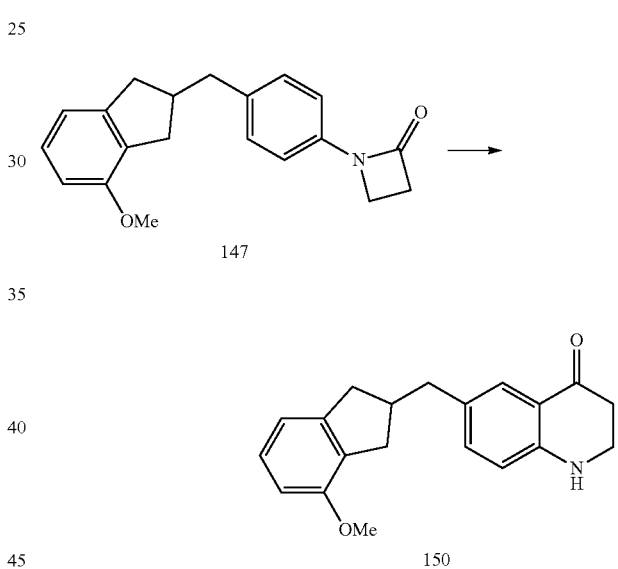

6-((4-Methoxy-2,3-dihydro-1H-inden-2-yl)methyl)-2,3-dihydroquinolin-4(1H)-one (150) To the round bottom flask already containing the dried, desiccated phenylazetidin-2-one 147 (789 mg, 2.57 mmol, 1.0 eq) was added anhyd. DCE under vacuum. The reaction vessel stirred under vacuum for 5 min then was flooded with Ar. Next, trifluoromethanesulfonic acid (TfOH, 0.681 mL, 7.70 mmol, 3.0 eq) was added via syringe. The reaction stirred under Ar at RT for up to 3 h and was monitored by TLC. Once complete, the reaction was quenched with dI H₂O (20 mL) and solid K₂CO₃ (one spatula full) and the layers separated. The organic layer was washed once with dI H₂O (1×30 mL), then sat. NaHCO₃ (1×30 mL), then brine (1×30 mL), then dried over MgSO₄, filtered, and concentrated under reduced pressure to yield the crude product, which was then purified using silica gel chromatography to yield the pure product as a yellow solid (205 mg, 25.9%). Product was characterized by ¹H NMR and ¹³C NMR on a Varian 500 MHz spectrometer in CDCl₃.

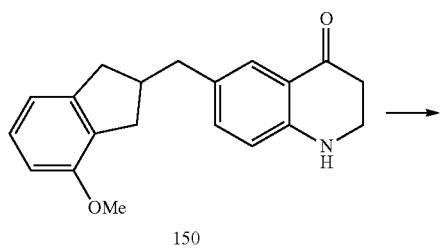

150

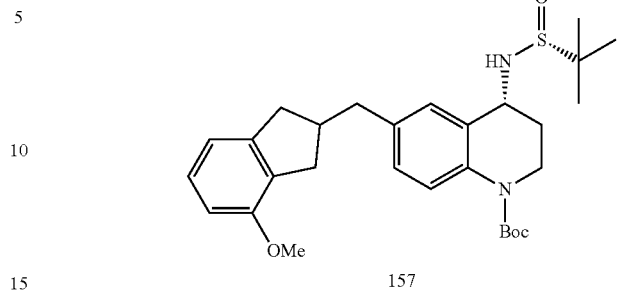

157

Tert-butyl (4R)-4-(((R)-tert-butylsulfinyl)amino)-6-((4-methoxy-2,3-dihydro-1H-inden-2-yl)methyl)-3,4-dihydro-quinoline-1(2H)-carboxylate (157) To a round bottom flask already containing dried, desiccated 6-substituted dihydroquinolinone intermediate 153 (83 mg, 0.20 mmol, 1.0 eq) was added (R)-2-methylpropane-2-sulfinamide (74 mg, 0.61 mmol, 3.0 eq), then the round bottom flask was placed under vacuum for 10 min. Meanwhile, a reflux condenser was flame-dried under vacuum, and then flooded with Ar. Next, anhyd. THF (~20 mL) was added to the reaction vessel containing starting reagents via syringe. The reaction solution allowed to stir under vacuum for ~5 min and then was flooded with Ar. The round bottom flask was placed in ice bath and allowed to equilibrate. Next, Ti(OEt)$_4$ (0.325 mL, 1.22 mmol, 6.0 eq) was added slowly via syringe. Once addition was complete, the reaction vessel was taken out of ice bath and placed in oil bath at 70° C.-75° C., equipped with condenser, and stirred for 48 h under Ar. The reaction was monitored by TLC for loss of ketone. Once sufficient conversion to the tert-butanesulfinyl imine was observed, reaction vessel was taken out of oil bath and cooled to ambient temperature. Meanwhile, an additional round bottom flask containing a stir bar was flame-dried under vacuum, then flooded with Ar, then NaBH$_4$ (46 mg, 1.22 mmol, 6.0 eq) was added quickly, and then reaction vessel was placed back under vacuum for 5 min. Minimal anhyd. THF was added (~5 mL) and vessel allowed to stir under vacuum for ~5 min, then was flooded with Ar. The round bottom flask was placed in dry ice/xylenes bath and allowed to equilibrate. Contents from the round bottom flask containing the imine intermediate were transferred to round bottom flask containing NaBH$_4$ via cannula. Once contents completely added, the reaction was taken out of dry ice/xylenes bath and allowed to warm to room temperature. The reaction stirred at ambient temperature for 3 h. Once the reaction was complete, MeOH was added to quench. The solvent was removed under reduced pressure yielding a solid residue. The residue was re-suspended in DCM, and the remaining solid was removed by filtration through a cotton plug and the mother liquor was concentrated and purified using silica gel chromatography to yield pure sulfonamide product as an off-white solid (43 mg, 41.3%). Product was characterized by $^1$H NMR and $^{13}$C NMR on a Varian 500 MHz spectrometer in CDCl$_3$.

153

Tert-butyl 6-((4-methoxy-2,3-dihydro-1H-inden-2-yl)methyl)-4-oxo-3,4-dihydroquinoline-1(2H)-carboxylate (153) To a flame-dried round bottom flask under Ar was added the 2,3-dihydroquinolin-4(1H)-one 150 (118 mg, 0.384 mmol, 1.0 eq), Boc$_2$O (101 mg, 0.46 mmol, 2.0 eq), and DMAP (5 mg, 0.038 mmol, 0.1 eq). The reaction vessel was placed back under vacuum for 5 min, then anhyd. DCM was added via syringe and the solution stirred for 5 min under vacuum. The round bottom flask was flooded with Ar, and DIPEA (0.08 mL, 0.46 mmol, 2.0 eq) was added via syringe. The reaction vessel was equipped with a condenser and placed in oil bath at 60° C. The reaction stirred at reflux for 16 h under Ar and was monitored by TLC. Once significant conversion to product was seen, the reaction was quenched using dl H$_2$O (20 mL) and the layers were separated. The organic layer was washed with sat. NaHCO$_3$ solution (1×20 mL) and brine (1×20 mL), then dried over MgSO$_4$, filtered, and concentrated under reduced pressure to yield a crude yellow oil which was purified using silica gel chromatography to obtain the pure product as a clear, colorless oil (83 mg, 53.2%). Product was characterized by $^1$H NMR and $^{13}$C NMR on a Varian 500 MHz spectrometer in CDCl$_3$.

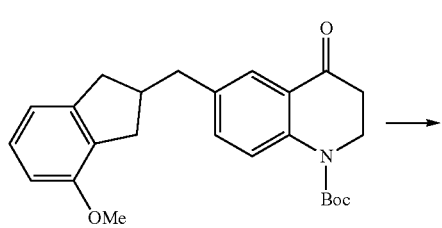

153

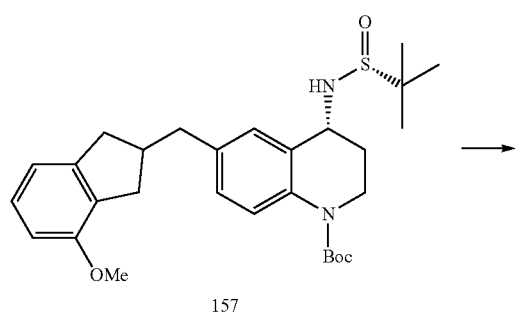

157

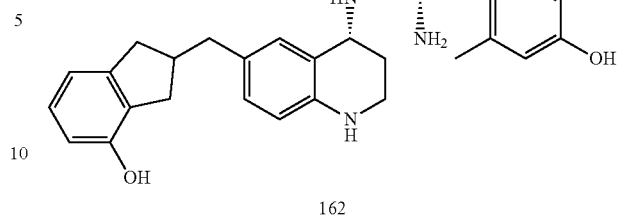

162

(2S)-2-amino-N-((4R)-6-((4-hydroxy-2,3-dihydro-1H-inden-2-yl)methyl)-1,2,3,4-tetrahydroquinolin-4-yl)-3-(4-hydroxy-2,6-dimethylphenyl)propanamide (162) To a round bottom flask already containing 161 (25 mg, 0.043 mmol, 1.0 eq) was added anhyd DCM and then reaction vessel was placed under vacuum for 10 min, then flooded with Ar. A 1M $BBr_3$ solution in DCM (0.2 mL, 0.172 mmol, 4.0 eq) was slowly added to the reaction vessel. Once completely added, solution stirred for 3 h. After 3 h, solvent was removed under reduced pressure and residue was resuspended in MeOH, then solvent was moved. This process was repeated 3×. The crude mixture was purified using semipreparative HPLC to yield title compound 162 (15 mg, 62.5%) as a white fluffy powder. Additional starting material, 161, was recovered but not included in final yield calculation. Product was characterized by $^1H$ NMR and $^{13}C$ NMR on a Varian 500 MHz spectrometer in $CDCl_3$ and mass spectrometry using an Agilent 6130 LC-MS mass spectrometer in positive mode. [M+Na]$^+$ predicted: 508.3. Observed: 508.1. Retention time 25.9 minutes.

161

(2S)-2-amino-3-(4-hydroxy-2,6-dimethylphenyl)-N-((4R)-6-((4-methoxy-2,3-dihydro-1H-inden-2-yl)methyl)-1,2,3,4-tetrahydroquinolin-4-yl)propanamide (161) To a round bottom flask already containing sulfinamide intermediate 157 (43 mg, 0.084 mmol, 1.0 eq) was added 15-20 mL dioxane followed by conc. HCl (6.0 eq, ~3 drops). The reaction stirred at RT for up to 3 h. Solvent was removed under reduced pressure to yield slightly yellow, clear residue. After removing solvent, residue was re-suspended in $Et_2O$, and solid crashed out. After washing the solid 3× with fresh $Et_2O$, the remaining $Et_2O$ was decanted off, yielding a white solid amine hydrochloride salt (15 mg). The amine intermediate and diBoc-Dmt (361 mg, 0.088 mmol, 1.05 eq) and the coupling reagents PyBOP (44 mg, 0.084 mmol, 1.0 eq), HOBt-Cl (14 mg, 0.084 mmol, 1.0 eq), were dissolved in DMF (10-15 mL) followed by the addition of the and DIPEA (0.84 mmol, 10.0 eq). The reaction mixture stirred for 18 h at room temperature. After concentration under reduced pressure, the crude residue was dissolved in a 1:1 mixture of DCM and TFA (10 mL) and stirred for 1 h. The mixture was concentrated and purified by semipreparative HPLC to yield the final compound as a TFA salt (35 mg, 79.5%). Product was characterized by $^1H$ NMR and $^{13}C$ NMR on a Varian 500 MHz spectrometer in $CDCl_3$ and mass spectrometry using an Agilent 6130 LC-MS mass spectrometer in positive mode. [M+Na]$^+$ predicted: 522.3. Observed: 522.1 [M+Na]$^+$. Retention time 31.7 minutes.

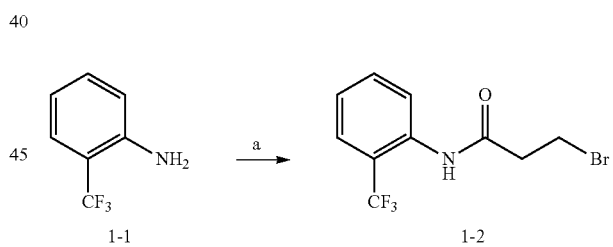

1-1    1-2

1a—To a round-bottom flask under inert argon atmosphere was added 1-1 (2 g, 12.56 mmol, 1 equiv), followed by dichloromethane (30 mL), potassium carbonate (5.14 g, 37.2 mmol, 3 equiv), then 3-bromopropionyl chloride (2.2 g, 13.0 mmol, 1.05 equiv) while stirring at room temperature. After 30 minutes, reaction was quenched with 2M NaOH (10 mL). Organic and aqueous phases were separated, then organic phase was washed with saturated aqueous NaCl solution. Organics were isolated, dried with magnesium sulfate and filtered through coarse (40-60 micron) fritted funnel. Solvent was removed under reduced pressure to yield compound 1-2 (3.38, 12.56 mmol, 100% yield), and was used without further purification. Product was characterized by $^1H$ NMR and $^{13}C$ NMR on a Varian 500 MHz spectrometer in $CDCl_3$.

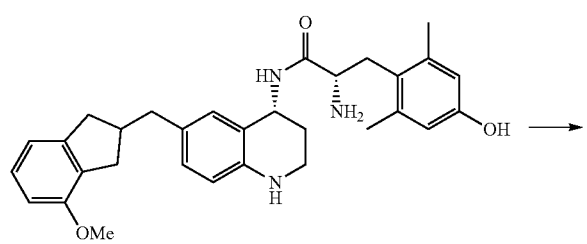

161

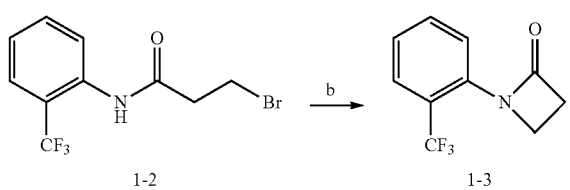 [SMILES: O=C(CCBr)Nc1ccccc1C(F)(F)F ; O=C1CCN1c1ccccc1C(F)(F)F]

1b—To a round-bottom flask was added 1-2 (3.38 g, 12.56 mmol, 1 equiv), then evacuated for 15 min before suspending in N—,N-dimethylformamide (50 mL) and flushing vessel with argon. A suspension of sodium tert-butoxide (1.27 g, 13.2 mmol, 1.05 equiv) in anhydrous DMF (60 mL) was slowly added to 1-2 at room temperature, stirring under argon atmosphere. After 2 hours, solvent was removed under reduced pressure, and the remaining oil was purified with Biotage Isolera flash chromatography system, using a linear gradient from 10% ethyl acetate and 90% hexanes to 20% ethyl acetate and 80% hexanes, yielding intermediate 1-3 (1.62 g, 7.52 mmol, 60% yield). Product was characterized by $^1$H and $^{13}$C NMR in CDCl$_3$.

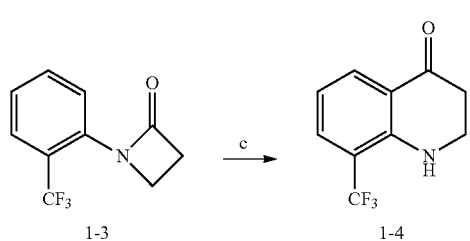 [SMILES: O=C1CCN1c1ccccc1C(F)(F)F ; O=C1CCNc2c1cccc2C(F)(F)F]

1c—A round-bottom flask containing 1-3 (1.62 g, 7.52 mmol, 1 equiv), was evacuated for 5 min before suspending in 1,2-dichloroethane (70 mL) and flushing vessel with argon. Trifluoromethanesulfonic acid (2.0 mL, 22.56 mmol, 3 equiv) was slowly added at room temperature, stirring under argon atmosphere. After 60 minutes, reaction was quenched with deionized water, then neutralized with 2M sodium hydroxide (NaOH). Organic and aqueous phases were separated, then organic phase was washed with saturated aqueous sodium chloride (NaCl) solution. Organics were isolated, dried with magnesium sulfate and filtered through coarse (40-60 micron) fritted funnel. Solvent was removed under reduced pressure, and the remaining oil was purified by flash chromatography, using a linear gradient from 20% ethyl acetate and 80% hexanes to 40% ethyl acetate and 60% hexanes, yielding intermediate 1-4 (0.85 g, 3.95 mmol, 52% yield). Product was characterized by H and $^{13}$C NMR in CDCl$_3$.

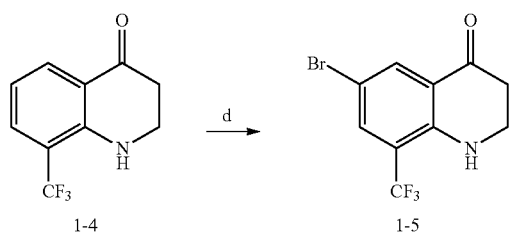 [SMILES: O=C1CCNc2c1cccc2C(F)(F)F ; O=C1CCNc2c1cc(Br)cc2C(F)(F)F]

1d—A round-bottom flask containing 1-4 (0.85 g, 3.95 mmol, 1 equiv), was evacuated for 5 min before suspending in dichloromethane (40 mL) and flushing vessel with argon. N-bromosuccinimide (0.74 g, 4.15 mmol, 1.05 equiv) was added, stirring under argon atmosphere at room temperature. After 30 minutes, reaction solvent was removed under reduced pressure, and the remaining residue was resuspended in carbon tetrachloride and cooled to 4° C. Cold suspension was filtered through diatomaceous earth with a coarse fritted funnel. Filtrate was purified by flash chromatography, using a linear gradient from 20% ethyl acetate and 80% hexanes to 40% ethyl acetate and 60% hexanes, yielding intermediate 1-5 (1.00 g, 3.40 mmol, 86% yield). Product was characterized by $^1$H and $^{13}$C NMR in CDCl$_3$.

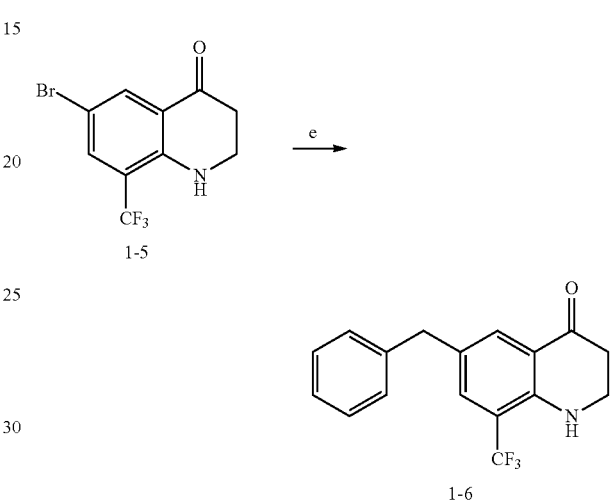

1e—To a pear-shaped flask under argon atmosphere was added 1-5 (180 mg, 0.61 mmol, 1 equiv), potassium carbonate (253 mg, 1.83 mmol, 3 equiv) and Pd(dppf)Cl$_2$ (44 mg, 0.06 mmol, 0.1 equiv). Reagents were then suspended in degassed, argon-sparged 3:1 acetone/H$_2$O (6 mL), and benzylboronic pinacol ester (0.27 mL, 1.22 mmol, 2 equiv) was added while stirring at room temperature under argon atmosphere. After addition of reagents, a reflux condenser under argon atmosphere was affixed and reaction flask was heated at 80° C. for 12 hours. Upon returning to room temperature, reaction solvents were removed under reduced pressure, and the resulting oil was resuspended in ethyl acetate. Organics were washed with a saturated solution of aqueous sodium chloride (NaCl), separated, and dried with magnesium sulfate. After filtering through a coarse frit, the filtrate was reconcentrated and purified by flash chromatography using a linear gradient from 20% ethyl acetate and 80% hexanes to 40% ethyl acetate and 60% hexanes, yielding intermediate 1-6 (176 mg, 0.58 mmol, 95% yield). Product was characterized by $^1$H and $^{13}$C NMR in CDCl$_3$.

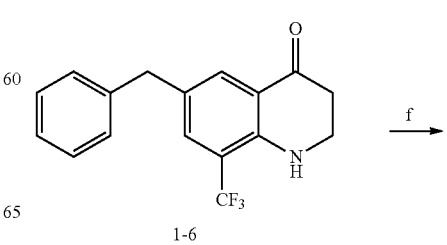

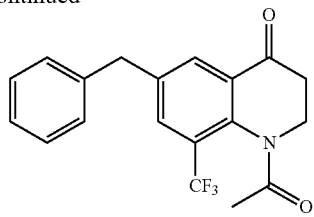

1-7

1f—To a round-bottom flask containing 1-6 (175 mg, 0.57 mmol, 1 equiv) under argon atmosphere was added acetic anhydride (12 mL, excess). A reflux condenser under inert atmosphere was affixed and the reaction was heated at 110° C. for 16 hours. Acetic anhydride was removed under reduced pressure, and the residual oil was purified by flash chromatography using a linear gradient from 10% ethyl acetate and 90% hexanes to 30% ethyl acetate and 70% hexanes, yielding intermediate 1-7 (45 mg, 0.13 mmol, 23% yield). Product was characterized by $^1$H, $^{13}$C, and HSQC NMR in CDCl$_3$.

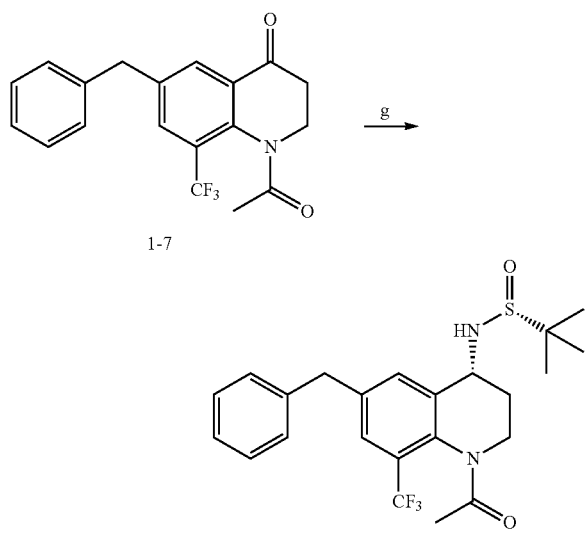

1g—To a pear-shaped flask containing 1-7 (45 mg, 0.13 mmol, 1 equiv) under argon atmosphere was added (R)-2-methylpropane-2-sulfinamide (47 mg, 0.39 mmol, 3 equiv), followed by tetrahydrofuran (2 mL). Reaction flask was cooled to 0° C., then titanium tetraethoxide (0.17 mL, 0.78 mmol, 6 equiv) was added dropwise and stirred 5 min before returning reaction mixture to room temperature. A flame-dried reflux condenser under argon atmosphere was affixed, and the reaction vessel was heated at 70° C. for 48 hours. Reaction was cooled to room temperature, then transferred via syringe to a flame-dried round-bottom flask containing sodium borohydride (30 mg, 0.78 mmol, 6 equiv) in tetrahydrofuran (2 mL) under argon atmosphere stirred at −78° C. After washing pear-shaped flask with additional 1 mL tetrahydrofuran and transferring to round-bottom flask, the reaction was warmed to room temperature. After stirring for 2 hours, reaction was quenched with methanol and stirred 15 minutes before removing solvent under reduced pressure. The resulting residue was suspended in ethyl acetate, then mixed with saturated aqueous ammonium chloride (NH4Cl) and shook vigorously. Repeated until organic phase became clear, then dried with magnesium sulfate and filtered through a coarse frit. The filtrate was reconcentrated and purified by flash chromatography using a linear gradient from 20% ethyl acetate and 80% hexanes to 50% ethyl acetate and 50% hexanes, yielding intermediate 1-8 (52 mg, 0.11 mmol, 90% yield). Product was characterized by $^1$H NMR in CDCl$_3$.

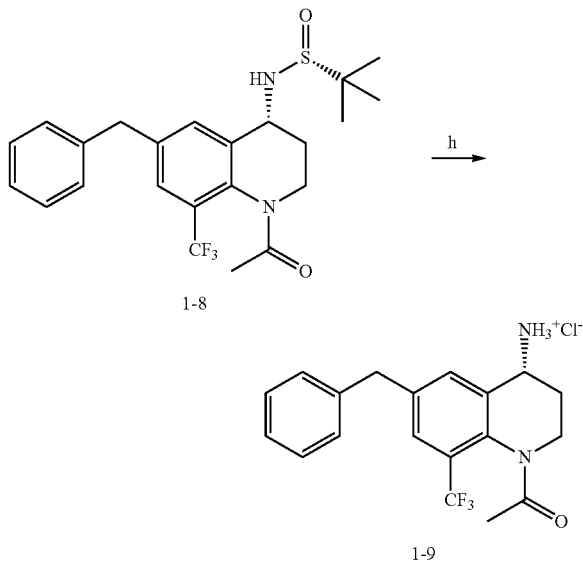

1h—To a pear-shaped flask containing 1-8 (40 mg, 0.09 mmol, 1 equiv) was added 1,4-dioxane (8 mL) followed by concentrated hydrochloric acid (5 drops, excess) and stirred at room temperature for 30 minutes before removing solvent. Reaction residue was washed with diethyl ether and cooled to −20° C. before decanting liquids. Washed precipitate with ether and decanted again, then dried under reduced pressure to yield 1-9 (32 mg, 0.08 mmol, 94% yield)

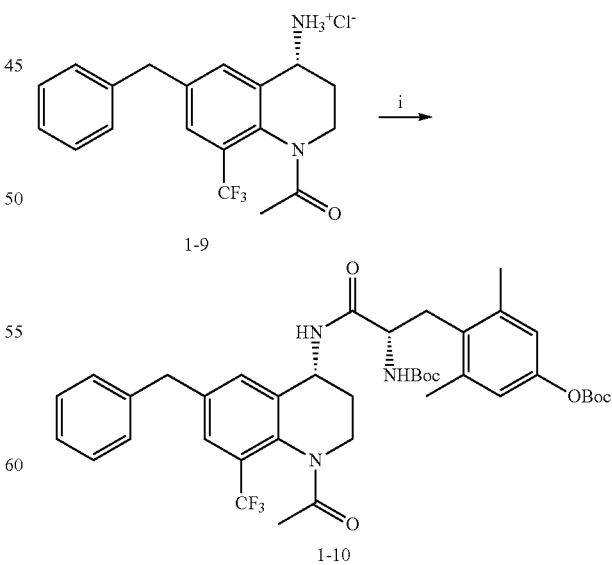

1i—To a pear-shaped flask containing 1-9 (32 mg, 0.08 mmol, 1.0 equiv) under argon atmosphere was added diBoc- Dmt (38 mg, 0.09 mmol, 1.1 equiv), PyBOP (48 mg, 0.09 mmol, 1.1 equiv), and 6-Cl HOBt (16 mg, 0.09 mmol, 1.1 equiv) before suspending in anhydrous N—,N-dimethylformamide (2 mL). Diisopropylethylamine (0.15 mL, 0.83 mmol, 10 equiv) was added dropwise and stirred under argon for 6.5 hours. Solvent was removed under reduced pressure, and residual oil was purified by flash chromatography using a linear gradient from 20% ethyl acetate and 80% hexanes to 50% ethyl acetate and 50% hexanes, yielding intermediate 1-10 (44 mg, 0.06 mmol, 75% yield). Carried forward without characterization.

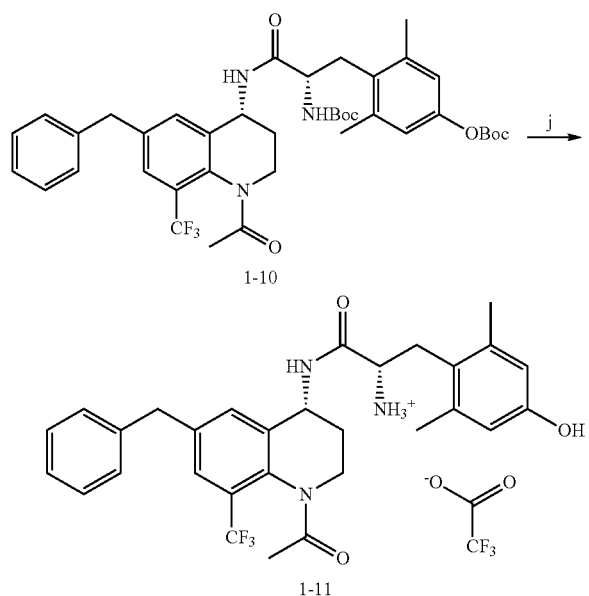

1j—To a pear-shaped flask containing 1-10 (44 mg, 0.06 mmol, 1 equiv) was added dichloromethane (5 mL), followed by trifluoroacetic acid (TFA, 3 mL) and stirred at room temperature. After 30 minutes, solvent was removed and remaining residue was suspended in 30% Solvent B (acetonitrile with 0.1% TFA) and 70% Solvent A (water with 0.1% TFA), then filtered through a fine (4-5.5 micron) frit. Filtrate was purified with a Waters semi-preparative HPLC using a Vydac protein and peptide C18 reverse phase column. A linear gradient from 30% B and 70% A to 50% B and 50% A over 20 minutes (1% per minute) with a flow rate of 10 mL/min was used to isolate 1-11. Organic solvent was then removed under reduced pressure, and remaining aqueous solution was lyophilized to give 1-11 as a white powder, >95% purity. Characterized by $^1$H, $^{13}$C NMR and high-resolution mass spectrometry. M+1 predicted: 540.23. Observed: 540.2467. Retention time: 38.1 minutes.†

†Purity of synthesized compounds and retention time were determined on a Waters Alliance 2690 analytical HPLC instrument and a Vydac protein and peptide C18 reverse phase column, using a linear gradient of 0% Solvent B and 100% Solvent A to 70% B and 30% A in 70 minutes (1% per minute) with a flow rate of 1 mL/min.

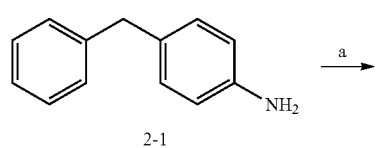

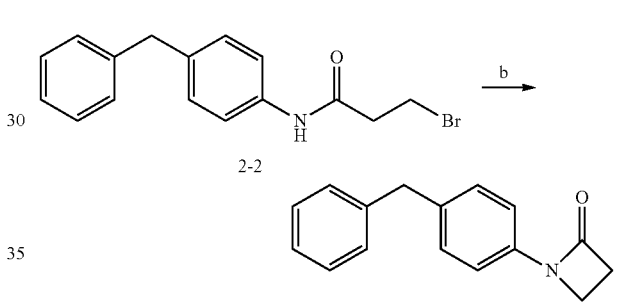

2a—To a round-bottom flask under inert argon atmosphere was added 2-1 (3.65 g, 19.92 mmol, 1 equiv), followed by dichloromethane (200 mL), potassium carbonate (3.56 g, 25.78 mmol, 1.3 equiv), then 3-bromopropionyl chloride (3.59 g, 20.92 mmol, 1.05 equiv) while stirring at room temperature. After 90 minutes, the reaction was quenched with 2M NaOH (10 mL). Organic and aqueous phases were separated, then organic phase was washed with saturated aqueous sodium chloride (NaCl) solution. Organics were isolated, dried with magnesium sulfate and filtered through a coarse (40-60 micron) frit. Solvent was removed under reduced pressure to yield compound 2-2 (6.34 g, 19.92 mmol, 100% yield), and was used without further purification. Product was characterized by $^1$H NMR and $^{13}$C NMR on a Varian 500 MHz spectrometer in CDCl$_3$.

2b—To a round-bottom flask was added 2-2 (6.34 g, 19.92 mmol, 1 equiv), then evacuated for 15 min before suspending in N—,N-dimethylformamide (100 mL) and flushing vessel with argon. A suspension of sodium tert-butoxide (2.10 g, 21.92 mmol, 1.1 equiv) in anhydrous DMF (60 mL) was slowly added to 2-2 at room temperature, stirring under argon atmosphere. After 2 hours, solvent was removed under reduced pressure, and the residual oil was resuspended in ethyl acetate. Organics were washed with a saturated solution of aqueous sodium chloride (NaCl), separated, and dried with magnesium sulfate. After filtering through a coarse frit, the filtrate was reconcentrated to a brown oil that crystallized upon standing. This solid was then purified by flash chromatography, using a linear gradient from 20% ethyl acetate and 80% hexanes to 40% ethyl acetate and 60% hexanes, yielding intermediate 2-3 (4.25 g, 17.92 mmol, 90% yield). Product was characterized by $^1$H and $^{13}$C NMR in CDCl$_3$.

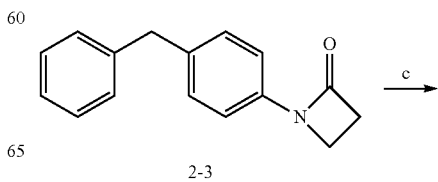

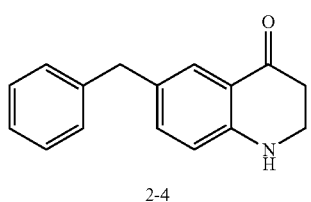

2-4

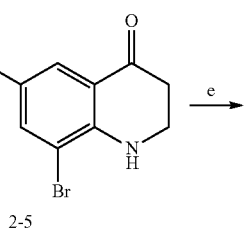

2-5

2c—A round-bottom flask containing 2-3 (3.75 g, 15.80 mmol, 1 equiv), was evacuated for 5 min before suspending in 1,2-dichloroethane (170 mL) and flushing vessel with argon. Trifluoromethanesulfonic acid (4.18 mL, 47.40 mmol, 3 equiv) was slowly added at room temperature, stirring under argon atmosphere. After 60 minutes, reaction was quenched with deionized water, then neutralized with 2M sodium hydroxide (NaOH). Organic and aqueous phases were separated, then organic phase was washed with saturated aqueous sodium chloride (NaCl) solution. Organics were isolated, dried with magnesium sulfate and filtered through coarse (40-60 micron) fritted funnel. Solvent was removed under reduced pressure, and the remaining oil was purified by flash chromatography, using a linear gradient from 20% ethyl acetate and 80% hexanes to 40% ethyl acetate and 60% hexanes, yielding intermediate 2-4 (3.34 g, 14.08 mmol, 89% yield). Product was characterized by $^1$H and $^{13}$C NMR in CDCl$_3$.

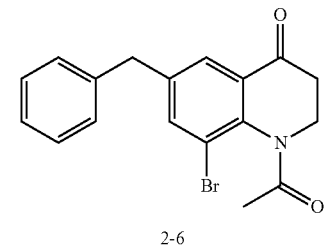

2-6

2e—To a round-bottom flask containing 2-5 (158 mg, 0.50 mmol, 1 equiv) under argon atmosphere was added acetic anhydride (10 mL, excess). A reflux condenser under inert atmosphere was affixed and the reaction was heated at 110° C. for 16 hours. Acetic anhydride was removed under reduced pressure, and the residual oil was purified by flash chromatography using a linear gradient from 10% ethyl acetate and 90% hexanes to 40% ethyl acetate and 60% hexanes, yielding intermediate 2-6 (63 mg, 0.16 mmol, 33% yield). Product was characterized by $^1$H, $^{13}$C, and HSQC NMR in CDCl$_3$.

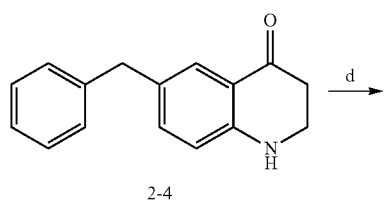

2-4

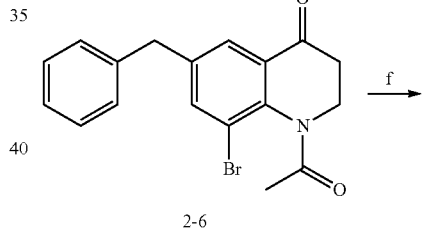

2-6

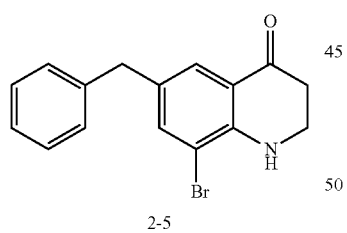

2-5

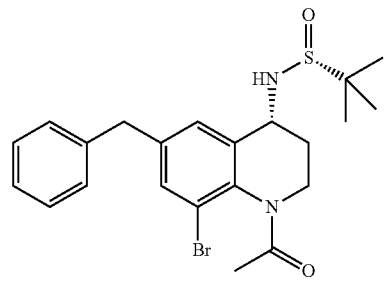

2-7

2d—A round-bottom flask containing 2-4 (650 mg, 2.74 mmol, 1 equiv), was evacuated for 5 min before suspending in dichloromethane (20 mL) and flushing vessel with argon. N-bromosuccinimide (512 mg, 2.87 mmol, 1.05 equiv) was added, stirring under argon atmosphere at room temperature. After 30 minutes, reaction solvent was removed under reduced pressure, and the remaining residue was purified by flash chromatography, using a linear gradient from 20% ethyl acetate and 80% hexanes to 40% ethyl acetate and 60% hexanes, yielding intermediate 2-5 (848 mg, 2.68 mmol, 98% yield). Product was characterized by $^1$H and $^{13}$C NMR in CDCl$_3$.

2f—To a pear-shaped flask containing 2-6 (63 mg, 0.16 mmol, 1 equiv) under argon atmosphere was added (R)-2-methylpropane-2-sulfinamide (60 mg, 0.49 mmol, 3 equiv), followed by tetrahydrofuran (3 mL). Reaction flask was cooled to 0° C., then titanium tetraethoxide (0.21 mL, 0.99 mmol, 6 equiv) was added dropwise and stirred 5 min before returning reaction mixture to room temperature. A flame-dried reflux condenser under argon atmosphere was affixed, and the reaction vessel was heated at 75° C. for 48 hours. Reaction was cooled to room temperature, then transferred via syringe to a flame-dried round-bottom flask containing sodium borohydride (38 mg, 0.99 mmol, 6 equiv) in tetrahydrofuran (3 mL) under argon atmosphere stirred at −78° C. After washing pear-shaped flask with additional 1 mL tetrahydrofuran, the reaction was warmed to room temperature. After stirring for 3 hours, reaction was quenched with methanol and stirred 15 minutes before removing solvent under reduced pressure. The resulting residue was suspended in ethyl acetate, then mixed with saturated aqueous ammonium chloride (NH$_4$Cl) and shook vigorously. Repeated until organic phase became clear, then dried with magnesium sulfate and filtered through a coarse frit. The filtrate was reconcentrated and purified by flash chromatography using a linear gradient from 1% methanol and 99% dichloromethane to 5% methanol and 95% dichloromethane, yielding intermediate 2-7 (65 mg, 0.14 mmol, 88% yield). Product was characterized by $^1$H, $^{13}$C and HSQC NMR in CDCl$_3$.

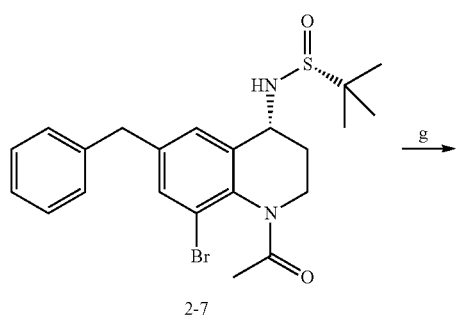

2-7

2g—To a pear-shaped flask containing 2-7 (65 mg, 0.14 mmol, 1 equiv) was added 1,4-dioxane (8 mL) followed by concentrated hydrochloric acid (8 drops, excess) and stirred at room temperature for 90 minutes before removing solvent. Reaction residue was washed with diethyl ether and cooled to −20° C. before decanting liquids. Washed precipitate with ether and decanted again, then dried under reduced pressure to yield 2-8 (58 mg, 0.14 mmol, 100% yield).

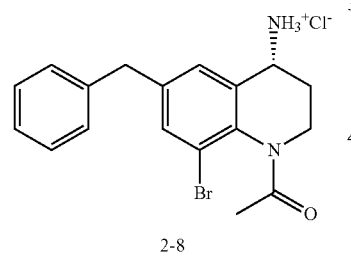

2-8

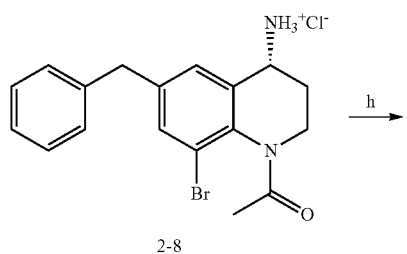

2-8

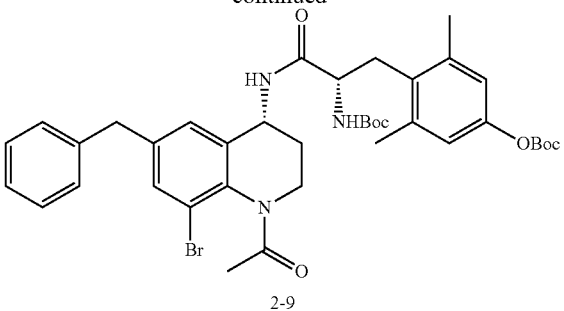

2-9

2h—To a pear-shaped flask containing 2-8 (58 mg, 0.14 mmol, 1.0 equiv) under argon atmosphere was added diBoc-Dmt (57 mg, 0.14 mmol, 1 equiv), PyBOP (79 mg, 0.15 mmol, 1.1 equiv), and 6-Cl HOBt (26 mg, 0.15 mmol, 1.1 equiv) before suspending in anhydrous N—,N-dimethylformamide (2 mL). Diisopropylethylamine (0.24 mL, 1.38 mmol, 10 equiv) was added dropwise and stirred under argon for 7 hours. Solvent was removed under reduced pressure, and residual oil was purified by flash chromatography using a linear gradient from 20% ethyl acetate and 80% hexanes to 50% ethyl acetate and 50% hexanes, yielding intermediate 2-9. Carried forward without characterization.

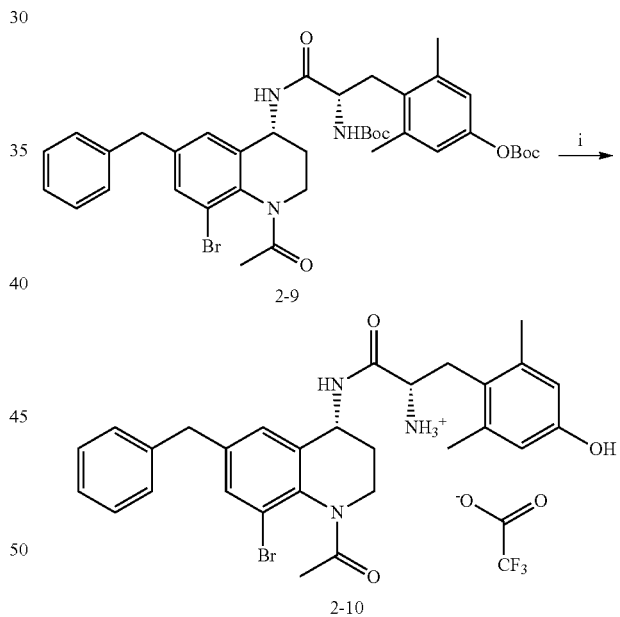

2i—To a pear-shaped flask containing 2-9 was added dichloromethane (5 mL), followed by trifluoroacetic acid (TFA, 3 mL) and stirred at room temperature. After 30 minutes, solvent was removed and remaining residue was suspended in 30% Solvent B (acetonitrile with 0.1% TFA) and 70% Solvent A (water with 0.1% TFA), then filtered through a fine (4-5.5 micron) frit. Filtrate was purified with a Waters semi-preparative HPLC using a Vydac protein and peptide C18 reverse phase column. A linear gradient from 30% B and 70% A to 50% B and 50% A over 20 minutes (1% per minute) with a flow rate of 10 mL/min was used to isolate 2-10. Organic solvent was then removed under reduced pressure, and remaining aqueous solution was lyophilized to give 2-10 as a white powder, >95% purity. Characterized by ¹H, ¹³C NMR and mass spectrometry using an Agilent 6130 LC-MS mass spectrometer in positive mode. M+1 predicted: 550.17. Observed: 550.2. (M+3 observed: 552.2. M+4 observed: 553.3). Retention time: 36.0 minutes.

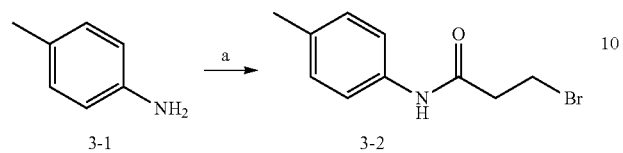

3a—To a round-bottom flask under inert argon atmosphere was added 3-1 (5.00 g, 46.7 mmol, 1 equiv), followed by 1,2-dichloroethane (100 mL), potassium carbonate (12.9 g, 93.4 mmol, 2 equiv), then 3-bromopropionyl chloride (8.4 g, 49.0 mmol, 1.05 equiv) while stirring at room temperature. After 60 minutes, the reaction was quenched with deionized water. Organic and aqueous phases were separated, then organic phase was washed with saturated aqueous sodium chloride (NaCl) solution. Organics were isolated, dried with magnesium sulfate and filtered through a coarse (40-60 micron) frit. Solvent was removed under reduced pressure to yield compound 3-2 (11.30 g, 46.7 mmol, 100% yield), and was used without further purification. Product was characterized by ¹H NMR and ¹³C NMR on a Varian 500 MHz spectrometer in CDCl₃.

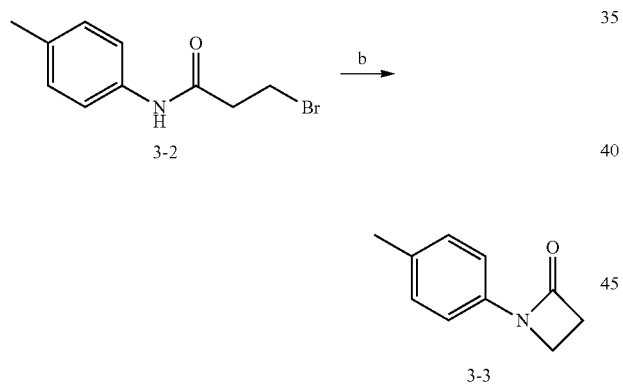

3b—To a round-bottom flask was added 3-2 (10.76 g, 44.4 mmol, 1 equiv), then evacuated for 15 min before suspending in N—,N-dimethylformamide (60 mL), flushing vessel with argon, and cooling on ice. A suspension of sodium tert-butoxide (4.48 g, 46.7 mmol, 1.05 equiv) in anhydrous DMF (60 mL) was slowly added to 3-2 at 0° C., stirring under argon atmosphere. After 90 minutes, solvent was removed under reduced pressure, and the residual oil was resuspended in ethyl acetate. Organics were washed with a saturated solution of aqueous sodium chloride (NaCl), separated, and dried with magnesium sulfate. After filtering through a coarse frit, the filtrate was reconcentrated to an oil, yielding crude intermediate 3-3 (7.07 g, 43.9 mmol, 99% yield). Product was characterized by ¹H and ¹³C NMR in CDCl₃ and used without further purification.

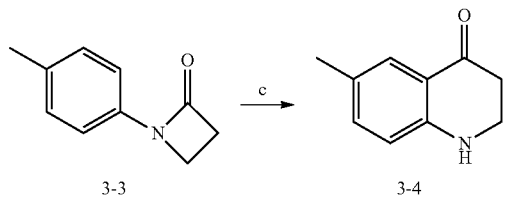

3c—A round-bottom flask containing 3-3 (7.07 g, 43.9 mmol, 1 equiv), was evacuated for 5 min before suspending in 1,2-dichloroethane (120 mL) and flushing vessel with argon. Trifluoromethanesulfonic acid (11.6 mL, 131.6 mmol, 3 equiv) was slowly added at room temperature, stirring under argon atmosphere. After 60 minutes, reaction was quenched with deionized water, then neutralized with 2M sodium hydroxide (NaOH). Organic and aqueous phases were separated, then organic phase was washed with saturated aqueous sodium chloride (NaCl) solution. Organics were isolated, dried with magnesium sulfate and filtered through coarse (40-60 micron) fritted funnel. Solvent was removed under reduced pressure, and the remaining oil was purified by flash chromatography, using a linear gradient from 20% ethyl acetate and 80% hexanes to 40% ethyl acetate and 60% hexanes, yielding intermediate 3-4 (4.23 g, 26.2 mmol, 60% yield). Product was characterized by ¹H and ¹³C NMR in CDCl₃.

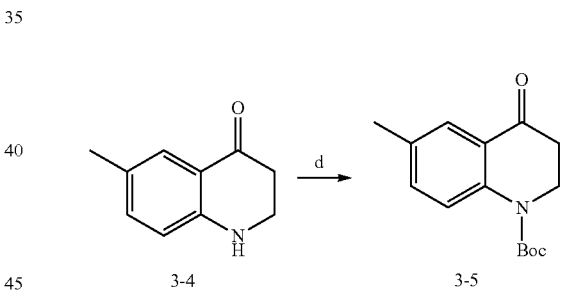

3d—To a round-bottom flask under argon atmosphere was added 3-4 (1.5 g, 9.3 mmol, 1 equiv) and suspended in dichloromethane (90 mL). Added di-tert-butyl dicarbonate (4.1 g, 18.6 mmol, 2 equiv), 4-dimethylaminopyridine (0.114 mg, 0.93 mmol, 0.1 equiv) and diisopropylethylamine (3.3 mL, 18.6 mmol, 2 equiv). After addition of reagents, a reflux condenser under argon atmosphere was affixed and reaction flask was heated at 60° C. for 6 hours. Upon returning to room temperature, reaction was quenched with deionized water (20 mL) and neutralized with 1M hydrochloric acid. Organics were washed with a saturated solution of aqueous sodium chloride (NaCl), separated, and dried with magnesium sulfate. After filtering through a coarse frit, the filtrate was reconcentrated and purified by flash chromatography using an isocratic method of 20% ethyl acetate and 80% hexanes, yielding intermediate 3-5 (1.87 g, 7.16 mmol, 77% yield). Product was characterized by ¹H and ¹³C NMR in CDCl₃.

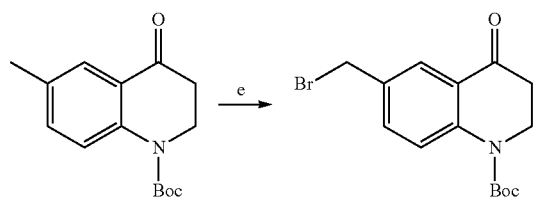

3-5 → 3-6

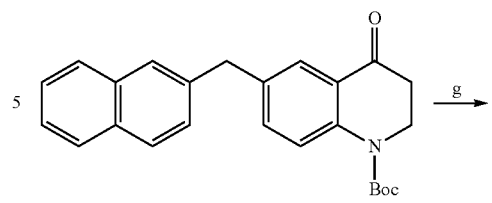

3-7

3e—To a round-bottom flask containing 3-5 (1.87 g, 7.16 mmol, 1 equiv) under argon atmosphere was added degassed, argon-sparged carbon tetrachloride (60 mL), followed by N-bromosuccinimide (1.34 g, 7.51 mmol, 1.05 equiv) and benzoyl peroxide (88 mg, 0.36 mmol, 0.05 equiv). A flame-dried reflux condenser under argon atmosphere was then affixed, and reaction was heated at 80° C. for 2 hours. Reaction mixture was cooled to 0° C., then filtered through diatomaceous earth and washed with additional carbon tetrachloride (20 mL). Filtrate was reconcentrated and purified by flash chromatography using an isocratic method of 10% ethyl acetate and 90% hexanes, yielding intermediate 3-6 (1.42 g, 4.17 mmol, 58% yield). Product was characterized by $^1$H and $^{13}$C NMR in CDCl$_3$.

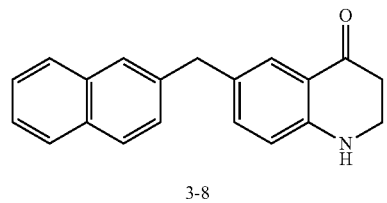

3-8

3g—To a round-bottom flask containing 3-7 (471 mg, 1.23 mmol, 1 equiv) was added dichloromethane (20 mL), followed by trifluoroacetic acid (6 mL, excess) and stirred at room temperature. After 30 minutes, solvent was removed and remaining residue was purified by flash chromatography using a linear gradient from 20% ethyl acetate and 80% hexanes to 40% ethyl acetate and 60% hexanes, yielding intermediate 3-8 (471 mg, 1.23 mmol, 83% yield). Product was characterized by $^1$H and $^{13}$C NMR in CDCl$_3$.

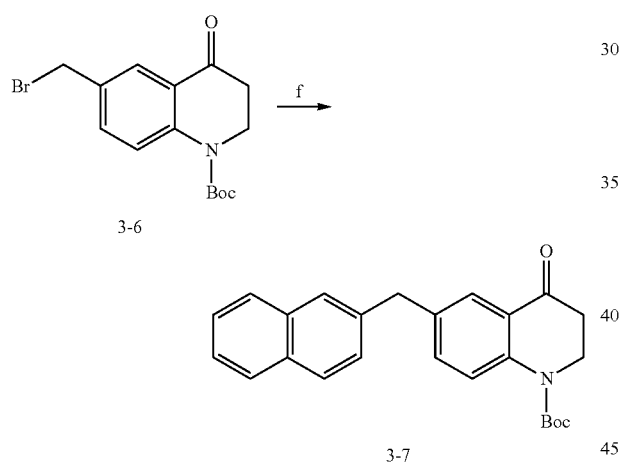

3-6 → 3-7

3f—To a round-bottom flask under argon atmosphere was added 3-6 (500 mg, 1.47 mmol, 1 equiv), potassium carbonate (609 mg, 4.41 mmol, 3 equiv), 2-naphthylboronic acid (505 mg, 2.94 mmol, 2 equiv), and Pd(dppf)Cl$_2$ (100 mg, 0.15 mmol, 0.1 equiv). Reagents were then suspended in degassed, argon-sparged 3:1 acetone/H$_2$O (20 mL), and a reflux condenser under argon atmosphere was affixed before heating reaction flask at 80° C. for 16 hours. Upon returning to room temperature, reaction solvents were removed under reduced pressure, and the resulting oil was resuspended in ethyl acetate. Organics were washed with a saturated solution of aqueous sodium chloride (NaCl), separated, and dried with magnesium sulfate. After filtering through a coarse frit, the filtrate was reconcentrated and purified by flash chromatography using a linear gradient from 10% ethyl acetate and 90% hexanes to 40% ethyl acetate and 60% hexanes, yielding intermediate 3-7 (471 mg, 1.23 mmol, 83% yield). Product was characterized by $^1$H and $^{13}$C NMR in CDCl$_3$.

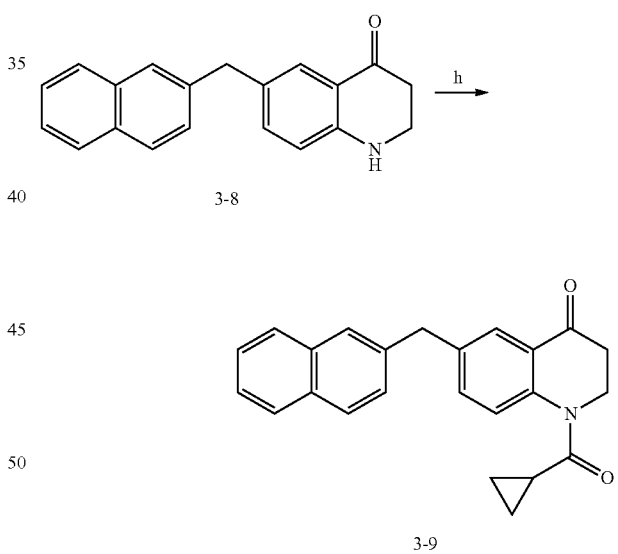

3-8 → 3-9

3h—To a pear-shaped flask containing 3-8 (100 mg, 0.35 mmol, 1.0 equiv) under argon atmosphere was added dichloromethane (5 mL), followed by triethylamine (0.10 mL, 0.70 mmol, 2 equiv) then cyclopropylcarbonyl chloride (0.06 mL, 0.70 mmol, 2 equiv) and stirred at room temperature. After 12 hours, solvent was removed and remaining residue was purified by flash chromatography using a linear gradient from 20% ethyl acetate and 80% hexanes to 60% ethyl acetate and 40% hexanes, yielding intermediate 3-9 (65 mg, 0.18 mmol, 52% yield). Product was characterized by $^1$H and $^{13}$C NMR in CDCl$_3$.

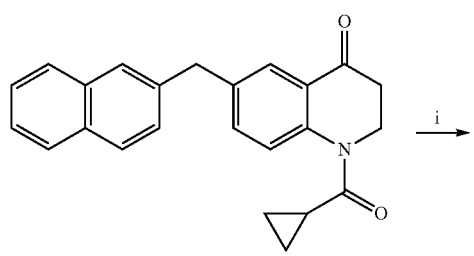

3-9

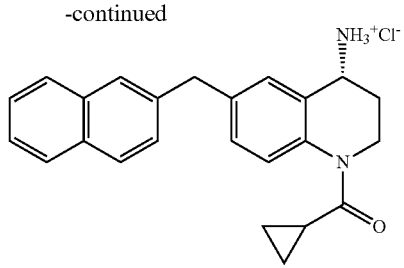

3-11

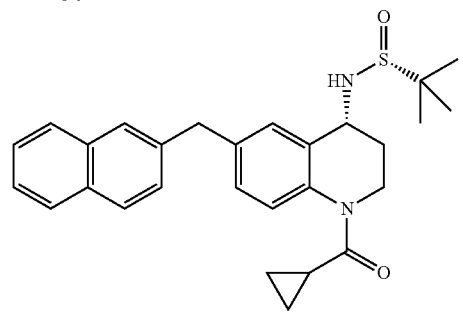

3-10

3i—To a pear-shaped flask containing 3-9 (65 mg, 0.18 mmol, 1 equiv) under argon atmosphere was added (R)-2-methylpropane-2-sulfinamide (66 mg, 0.55 mmol, 3 equiv), followed by tetrahydrofuran (3 mL). Reaction flask was cooled to 0° C., then titanium tetraethoxide (0.23 mL, 1.10 mmol, 6 equiv) was added dropwise and stirred 5 min before returning reaction mixture to room temperature. A flame-dried reflux condenser under argon atmosphere was affixed, and the reaction vessel was heated at 75° C. for 48 hours. Reaction was cooled to room temperature, then transferred via syringe to a flame-dried round-bottom flask containing sodium borohydride (42 mg, 1.10 mmol, 6 equiv) in tetrahydrofuran (3 mL) under argon atmosphere stirred at −78° C. After washing pear-shaped flask with additional 1 mL tetrahydrofuran, the reaction was warmed to room temperature. After stirring for 2 hours, reaction was quenched with methanol and stirred 15 minutes before removing solvent under reduced pressure. The resulting residue was suspended in ethyl acetate, then filtered through a plug of cotton and celite. The filtrate was reconcentrated and purified by flash chromatography using a linear gradient from from 20% ethyl acetate and 80% hexanes to 100% ethyl acetate and 0% hexanes, yielding intermediate 3-10, which was carried forward without characterization.

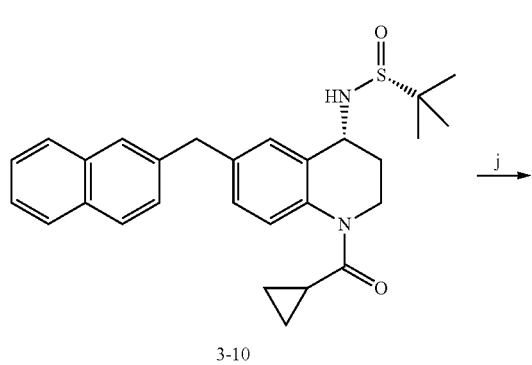

3-10

3j—To a pear-shaped flask containing 3-10 was added 1,4-dioxane (6 mL) followed by concentrated hydrochloric acid (5 drops, excess) and stirred at room temperature for 90 minutes before removing solvent. Reaction residue was washed with diethyl ether and cooled to −20° C. before decanting liquids. Washed precipitate with ether and decanted again, then dried under reduced pressure to yield 3-11 (35 mg, 0.089 mmol, 49% yield over 2 steps).

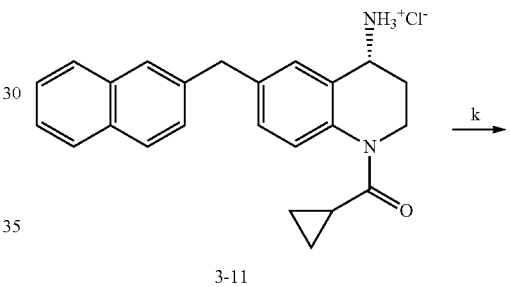

3-11

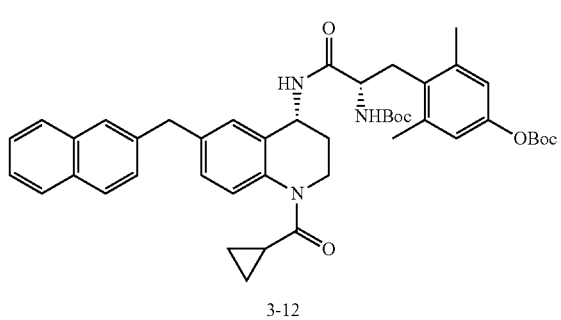

3-12

3k—To a pear-shaped flask containing 3-11 (35 mg, 0.089 mmol, 1.0 equiv) under argon atmosphere was added diBoc-Dmt (40 mg, 0.098 mmol, 1 equiv), PyBOP (51 mg, 0.098 mmol, 1.1 equiv), and 6-Cl HOBt (17 mg, 0.098 mmol, 1.1 equiv) before suspending in anhydrous N—,N-dimethylformamide (2 mL). Diisopropylethylamine (0.16 mL, 0.89 mmol, 10 equiv) was added dropwise and stirred under argon for 6 hours. Solvent was removed under reduced pressure, and residual oil was purified by flash chromatography using a linear gradient from 20% ethyl acetate and 80% hexanes to 50% ethyl acetate and 50% hexanes, yielding intermediate 3-12. Carried forward without characterization.

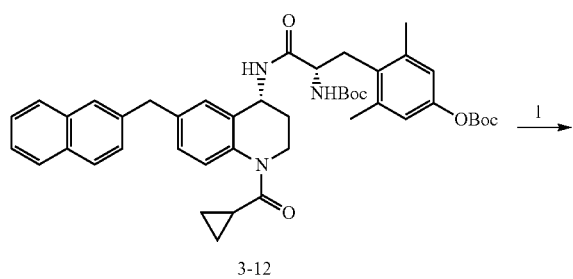

3-12

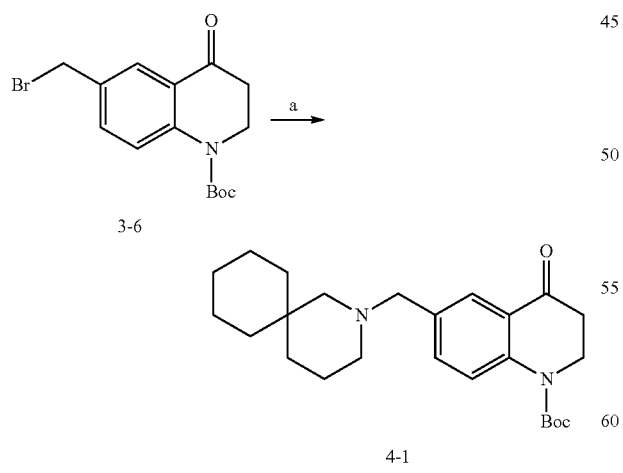

3-13

3l—To a pear-shaped flask containing 3-12 was added dichloromethane (5 mL), followed by trifluoroacetic acid (TFA, 3 mL) and stirred at room temperature. After 30 minutes, solvent was removed and remaining residue was suspended in 30% Solvent B (acetonitrile with 0.1% TFA) and 70% Solvent A (water with 0.1% TFA), then filtered through a fine (4-5.5 micron) frit. Filtrate was purified with a Waters semi-preparative HPLC using a Vydac protein and peptide C18 reverse phase column. A linear gradient from 30% B and 70% A to 50% B and 50% A over 20 minutes (1% per minute) with a flow rate of 10 mL/min was used to isolate 3-13. Organic solvent was then removed under reduced pressure, and remaining aqueous solution was lyophilized to give 3-13 as a white powder, >95% purity. Characterized by $^1$H, $^{13}$C NMR and LC/MS. M+1 predicted: 548.29. Observed: 548.3. (M+Na observed: 570.3). Retention time: 42.9 minutes.

3-6

4-1

4a—To a pear-shaped flask containing 3-6 (138 mg, 0.41 mmol, 1.0 equiv) under argon atmosphere was added N—,N-dimethylformamide (5 mL), followed by potassium carbonate (170 mg, 1.23 mmol, 3 equiv) then 2-azaspiro [5.5]undecane (0.78 mg, 0.51 mmol, 1.25 equiv) in N—,N-dimethylformamide (1 mL) and stirred at room temperature. After 18 hours, solvent was removed and remaining residue was purified by flash chromatography using a linear gradient from 1% methanol and 99% dichloromethane to 5% methanol and 95% dichloromethane, yielding intermediate 4-1 (152 mg, 0.37 mmol, 91% yield). Product was characterized by $^1$H, and $^{13}$C NMR in CDCl$_3$.

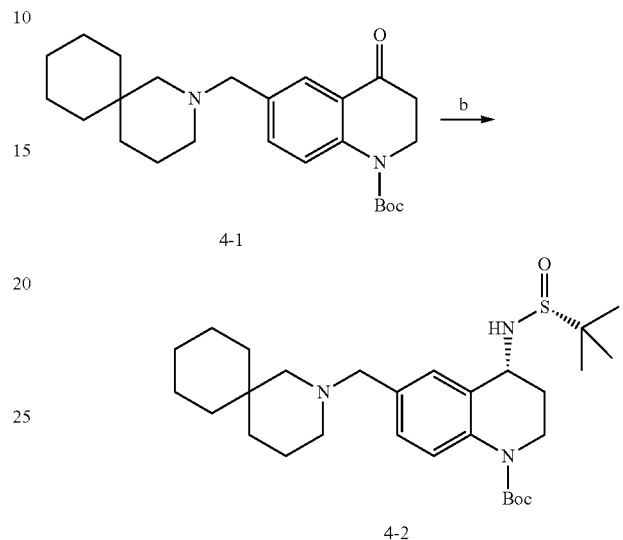

4-1

4-2

3i—To a pear-shaped flask containing 4-1 (123 mg, 0.30 mmol, 1 equiv) under argon atmosphere was added (R)-2-methylpropane-2-sulfinamide (109 mg, 0.90 mmol, 3 equiv), followed by tetrahydrofuran (3 mL). Reaction flask was cooled to 0° C., then titanium tetraethoxide (0.38 mL, 1.80 mmol, 6 equiv) was added dropwise and stirred 5 min before returning reaction mixture to room temperature. A flame-dried reflux condenser under argon atmosphere was affixed, and the reaction vessel was heated at 75° C. for 48 hours. Reaction was cooled to room temperature, then transferred via syringe to a flame-dried round-bottom flask containing sodium borohydride (68 mg, 1.80 mmol, 6 equiv) in tetrahydrofuran (3 mL) under argon atmosphere stirred at −78° C. After washing pear-shaped flask with additional 1 mL tetrahydrofuran, the reaction was warmed to room temperature. After stirring for 2 hours, reaction was quenched with methanol and stirred 15 minutes before removing solvent under reduced pressure. The resulting residue was suspended in dichloromethane, then filtered through a plug of cotton and celite. The filtrate was reconcentrated, yielding crude intermediate 4-2, which was carried forward without characterization.

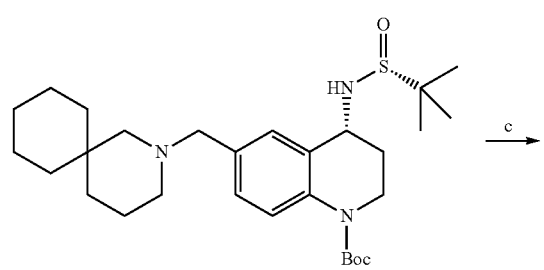

4-2

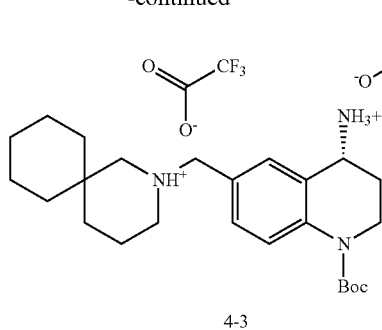

4-3

4c—To a pear-shaped flask containing 4-2 was added 1,4-dioxane (6 mL) followed by concentrated hydrochloric acid (5 drops, excess) and stirred at room temperature for 60 minutes before removing solvent. Reaction residue was washed with diethyl ether and cooled to −20° C. before decanting liquids. Washed precipitate with ether and decanted again, then dried under reduced pressure. Precipitate was resuspended in 10% B and 90% A, and purified with a Biotage Isolera flash chromatography system using a C18 reverse phase column. A linear gradient from 0% B and 100% A to 100% B and 0% A over 10 minutes (10% per minute) with a flow rate of 45 mL/min was used to isolate 4-3. Solvent was then removed under reduced pressure, and remaining aqueous solution was lyophilized to give 4-3 (30 mg, 0.05 mmol, 15% yield over 2 steps) as a white powder, >95% purity. Characterized by LC/MS and $^1$H, $^{13}$C and HSQC NMR in CD$_3$OD.

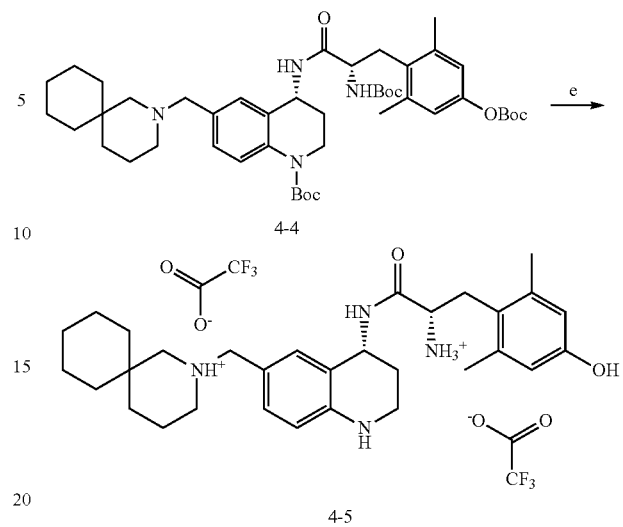

4-3

4-4

4d—To a pear-shaped flask containing 4-3 (30 mg, 0.05 mmol, 1.0 equiv) under argon atmosphere was added diBoc-Dmt (30 mg, 0.07 mmol, 1.5 equiv), PyBOP (37 mg, 0.07 mmol, 1.5 equiv), and 6-Cl HOBt (12 mg, 0.07 mmol, 1.5 equiv) before suspending in anhydrous N—,N-dimethylformamide (2 mL). Diisopropylethylamine (0.11 mL, 0.46 mmol, 10 equiv) was added dropwise and stirred under argon for 6 hours. Solvent was removed under reduced pressure yielding intermediate 3-12. Carried forward without characterization.

4e—To a pear-shaped flask containing 4-4 was added dichloromethane (5 mL), followed by trifluoroacetic acid (TFA, 3 mL) and stirred at room temperature. After 30 minutes, solvent was removed and remaining residue was suspended in 10% Solvent B (acetonitrile with 0.1% TFA) and 90% Solvent A (water with 0.1% TFA), then filtered through a fine (4-5.5 micron) frit. Filtrate was purified with a Waters semi-preparative HPLC using a Vydac protein and peptide C18 reverse phase column. A linear gradient from 10% B and 90% A to 60% B and 40% A over 50 minutes (1% per minute) with a flow rate of 10 mL/min was used to isolate 4-5. Organic solvent was then removed under reduced pressure, and remaining aqueous solution was lyophilized to give 4-5 as a white powder, >95% purity. Characterized by $^1$H, $^{13}$C NMR and LC/MS. M+1 predicted: 505.35. Observed: N/A. Retention time: 26.8 minutes.

Biological Assay Data

Binding affinity is measured using any suitable technique, such as the competitive binding assays described in the Example; Przydzial et al., I. Pept. Res. 2005; 65(3):333-42; Balboni et al., I. Med. Chem. 2002; 45:5556-5563; Lazarus et al., I. Med Chem. 1991; 34: 1350-1359; Salvadori et al., I. Med. Chem. 1999; 42:5010-5019; and Balboni et al., Bioorg. Med. Chem. 2003; 11:5435-5441. Alternative techniques for evaluating binding to MOR or DOR include, for example, flow cytometry, immunofluorescence microscopy, immunoelectron microscopy, and confocal laser microscopy. See, for example, U.S. Pat. No. 4,661,913, and Cechetto et al., Exp Cell Res. 2000; 260:30-39

Additional examples of techniques for examining agonist and/or antagonist activity of a compound include, but are not limited to, the mouse vas deferens (MVD) bioassay of DOR bioactivity and the guinea pig ileum (GPI) bioassay of MOR activity, both of which are described in Sasaki et al., Bioorg. Med. Chem. 2003; 11:675-678 and U.S. Patent Application Publication No. 20080269143. In vivo models for evaluating opioid receptor activity in response to opioid receptor modulators include but are not limited to, the tail flick test (Harris et al., J. Pharmacol. Meth. 1988; 20: 103-108; and Sing et al., P.A. Amber (v. 3.0. rev. A), Dept. Pharm. Chem., University of California, San Francisco (1988)) and the hot-plate test (see, e.g., Woolfe et al., J. Pharmacol. Exp. Ther. 1944; 80:300-307).

In Vitro Pharmacology-Cell Lines and Membrane Preparations. All tissue culture reagents were purchased from Gibco Life Sciences (Grand Island, N.Y., U.S.). C6-rat glioma cells stably transfected with a rat $\mu$ (C6-MOR) or rat $\delta$ (C6-DOR) opioid receptor20 and Chinese hamster ovary (CHO) cells stably expressing a human K (CHO-KOR) opioid receptor21 were used for all in vitro assays. Cells were grown to confluence at 37° C. in 5% $CO_2$ in Dulbecco's modified Eagle medium containing 10% fetal bovine serum and 5% penicillin/streptomycin. Membranes were prepared by washing confluent cells three times with ice cold phosphate buffered saline (0.9% NaCl, 0.61 mM $Na_2HPO_4$, 0.38 mM $KH_2PO_4$, pH 7.4). Cells were detached from the plates by incubation in warm harvesting buffer (20 mM HEPES, 150 mM NaCl, 0.68 mM EDTA, pH 7.4) and pelleted by centrifugation at 200 g for 3 min. The cell pellet was suspended in ice-cold 50 mM Tris-HCl buffer, pH 7.4, and homogenized with a Tissue Tearor (Biospec Products, Inc., Bartlesville, Okla., U.S.) for 20 s at setting 4. The homogenate was centrifuged at 20 000 g for 20 min at 4° C., and the pellet was rehomogenized in 50 mM Tris-HCl with a Tissue Tearor for 10 s at setting 2, followed by recentrifugation. The final pellet was resuspended in 50 mM Tris-HCl and frozen in aliquots at 80° C. Protein concentration was determined via Bradford assay using bovine serum albumin as the standard.

Radioligand Binding Assays. Radioactive compounds were purchased from Perkin-Elmer (Waltham, Mass., U.S.). Opioid ligand binding assays were performed using competitive displacement of 0.2 nM [3H]diprenorphine (250 $\mu$Ci, 1.85 TBq/mmol) by the test compound from membrane preparations containing opioid receptors. The assay mixture, containing membrane suspension (20 $\mu$g protein/tube) in 50 mM Tris-HCl buffer (pH 7.4), [3H]diprenorphine, and various concentrations of test peptide, was incubated at room temperature for 1 h to allow binding to reach equilibrium. The samples were rapidly filtered through Whatman GF/C filters using a Brandel harvester (Brandel, Gaithersburg, Md., U.S.) and washed three times with 50 mM Tris-HCl buffer. The radioactivity retained on dried filters was determined by liquid scintillation counting after saturation with EcoLume liquid scintillation cocktail in a Wallac 1450 MicroBeta (Perkin-Elmer, Waltham, Mass., U.S.). Nonspecific binding was determined using 10 $\mu$M naloxone. Inhibitory constant ($K_i$) values were calculated using nonlinear regression analysis to fit a logistic equation to the competition data using GraphPad Prism, version 5.01, for Windows (GraphPad Software Inc., La Jolla, Calif.). The results presented are the mean±standard error from at least three separate assays performed in duplicate.

Stimulation of [$^{35}$S]GTPyS Binding. Agonist stimulation of [35S]guanosine 5'-O-[$\gamma$-thio]triphosphate ([$^{35}$S]GTPyS, 1250 Ci, 46.2 TBq/mmol) binding was measured as described previously Briefly, membranes (10-20 $\mu$g of protein/tube) were incubated 1 h at room temperature in GTPyS buffer (50 mM Tris-HCl, 100 mM NaCl, 5 mM $MgCl_2$, pH 7.4) containing 0.1 nM [$^{35}$S]GTPyS, 30 $\mu$M guanosine diphosphate (GDP), and varying concentrations of test peptides. Peptide stimulation of [$^{35}$S]GTPyS was compared with 10 $\mu$M standard compounds [D-Ala$^2$,N-MePhe$^4$,Gly-ol]enkephalin (DAMGO) at MOR, D-Pen$^{2,5}$-enkephalin (DPDPE) at DOR, or U.S. Pat. No. 69,593 at KOR. The reaction was terminated by rapidly filtering through GF/C filters and washing 10 times with GTPyS buffer, and retained radioactivity was measured as described above. The results presented are the mean±standard error from at least three separate assays performed in duplicate; maximal stimulation was determined using nonlinear regression analysis with GraphPad Prism (GraphPad Software Inc., La Jolla, Calif.).

In Vivo Pharmacology. Animals. Adult male C57BL/6 mice weighing between 20 and 30 g at 8-16 weeks old were used for the current experiments (obtained from Jackson Laboratories (Bar Harbor, Me.), Harlan (Indianapolis, Ind.), or bred in-house). Mice were group-housed and had free access to food and water at all times. Experiments were conducted in the housing room, which was maintained on a 12 h light/dark cycle (with lights on at 0700). Each mouse was used only once and experiments were conducted between 11 a.m. and 4 p.m. Studies were performed in accordance with the University of Michigan Committee on the Use and Care of Animals and the Guide for the Care and Use of Laboratory Animals (National Research Council, 2011 publication).

Antinociception. The antinociceptive effects of the compounds disclosed herein and morphine can be evaluated in the warm water tail withdrawal assay using a cumulative dosing procedure. To determine tail withdrawal latencies, each mouse was placed briefly into a plastic, cylindrical restrainer and 2-3 cm of the tail tip was placed into a water bath maintained at 50° C. The latency to withdraw the tail was recorded with a maximum cutoff time of 20 s. If the mouse did not remove its tail by the cutoff time, the experimenter removed its tail from the water to prevent tissue damage. Each animal received an injection of saline (intraperitoneal, ip) and then 30 min later, the baseline withdrawal latencies were recorded and ranged between 3 and 6 s. Following baseline determinations, three increasing doses (1, 2.2, and 6.8 mg/kg) of 1(4R) were given at 30 min intervals to provide final doses of 1, 3.2, and 10 mg/kg. Thirty minutes after each injection, the tail withdrawal latency was measured as described above. To confirm that 1(4R) was acting at opioid receptors, the cumulative dose response was repeated over the doses 3.2, 10, and 32 mg/kg following a 30 min pretreatment with 1 mg/kg naltrexone (ip). To determine the time-course of antinociceptive action the tail-withdrawal test was performed at varying times following administration of morphine (10 mg/kg, ip) or 1(4R) (10 mg/kg, ip). An indication of fully efficacious indicates that the mouse didn't withdraw tails up to the 20 second cut off time. An indication of partially efficacious indicates that the tail withdrawal of the mouse was prior to the 20 second cut off time but longer than the negative control time. An indication of inactive indicates that the tail withdrawal of the mouse was the same time as the negative control.

Analytical data (molecular ion mass, HPLC retention time) for exemplary compounds of Formula (I) can be found in Table 1, below. The compounds were made in accordance with the synthetic scheme as noted in Table 1, using the appropriate starting materials. Binding affinity ($K_i$), potency ($EC_{50}$), and efficacy (% stimulation) data for exemplary compounds of Formula (I) can be found in Table 2, below. Antinociception data for exemplary compounds of Formula (I) can be found in Table 3, below.

TABLE 1

| Cmp. ID | Expected Mass | Found Mass | HPLC Retention Time (min)[1] | Synthetic Route |
|---|---|---|---|---|
| 1001 | 443.26 | 466.2 (M + Na) | 27.2 | Scheme 1 |
| 1002 | 443.26 | 466.2 (M + Na) | 29.2 | Scheme 1 |
| 1004 | 443.26 | 466.2 (M + Na) | 33.3 | Scheme 1 |
| 1005 | 443.26 | 466.2 (M + Na) | 34.9 | Scheme 1 |

TABLE 1-continued

| Cmp. ID | Expected Mass | Found Mass | HPLC Retention Time (min)[1] | Synthetic Route |
|---|---|---|---|---|
| 1006 | 471.29 | 472.3 (M + H) | 41.8 | Scheme 1 |
| 1007 | 443.26 | 466.1 (M + Na) | 28.6 | Scheme 1 |
| 1008 | 443.26 | 466.1 (M + Na) | 31.6 | Scheme 1 |
| 1009 | 447.23 | 470.1 (M + Na) | 26.7 | Scheme 1 |
| 1010 | 447.23 | 470.1 (M + Na) | 29.9 | Scheme 1 |
| 1011 | 423.29 | 446.3 (M + Na) | 32.3 | Scheme 1 |
| 1012 | 423.29 | 446.3 (M + Na) | 35.0 | Scheme 1 |
| 1013 | 409.27 | 410.3 (M + H) | 27.8 | Scheme 1 |
| 1014 | 443.26 | 466.2 (M + Na) | 28.8 | Scheme 4 |
| 1015 | 469.27 | 492.3 (M + Na) | 28.1 | Scheme 1 |
| 1016 | 469.27 | 492.3 (M + Na) | 30.2 | Scheme 1 |
| 1017 | 431.22 | 432.2 (M + H) | 24.4 | Scheme 1 |
| 1018 | 431.22 | 432.2 (M + H) | 27.3 | Scheme 1 |
| 1019 | 473.23 | 474.2 (M + H) | 31.0 | Scheme 1 |
| 1020 | 473.23 | 474.2 (M + H) | 32.8 | Scheme 1 |
| 1021 | 483.15 | 506.1 (M + Na) | 30.9 | Scheme 2, Scheme 3 |
| 1022 | 505.27 | 528.2 (M + Na) | 35.4 | Scheme 3 |
| 1023 | 429.24 | 430.3 (M + H) | 27.6 | Scheme 3 |
| 1024 | 429.24 | 430.3 (M + H) | 29.0 | Scheme 3 |
| 1025 | 465.18 | 488.2 (M + Na) | 29.8 | Scheme 3 |
| 1026 | 507.19 | 508.2 (M + H) | 35.5 | Scheme 3 |
| 1027 | 507.19 | 530.2 (M + Na) | 35.3 | Scheme 3 |
| 1028 | 453.14 | 476.1 (M + Na) | 32.6 | Scheme 3 |
| 1029 | 461.23 | 484.2 (M + Na) | 21.4 | Scheme 3 |
| 1030 | 465.18 | 488.2 (M + Na) | 28.9 | Scheme 3 |
| 1031 | 503.24 | 504.3 (M + H)– | 30.2 | Scheme 3 |
| 1032 | 497.16 | 520.2 (M + Na) | 30.7 | Scheme 3 |
| 1033 | 525.30 | 526.1 (M + H) | 40.6 | Scheme 3 |
| 1034 | 539.31 | 540.3 (M + H) | 44.8 | Scheme 3 |
| 1035 | 499.28 | 522.1 (M + H) | 31.7 | Scheme 3 |
| 1036 | 485.27 | 508.1 (M + Na) | 25.9 | Scheme 3 |
| 1037 | 499.28 | 500.1 (M + H) | 30.1 | Scheme 3 |
| 1038 | 485.27 | 508.1 (M + Na) | 31.7 | Scheme 3 |
| 1039 | 429.24 | 452.2 (M + Na) | 33.2 | Scheme 3 |
| 1040 | 471.25 | 472.1 (M + H) | 32.5 | Scheme 3 |
| 1041 | 519.29 | 542.3 (M + Na) | 44.2 | Scheme 3 |
| 1042 | 561.30 | 562.3 (M + H) | 42.4 | Scheme 3 |
| 1043 | 483.29 | 506.1 (M + Na) | 34.0 | Scheme 3 |
| 1044 | 527.28 | 528.3 (M + H) | 42.9 | Scheme 3 |
| 1124 | 525.30 | 526.1 (M + H) | 41.8 | Scheme 3 |
| 1045 | 459.25 | 482.3 (M + Na) | 27.8 | Scheme 3 |
| 1046 | 445.24 | 468.3 (M + Na) | 22.0 | Scheme 3 |
| 1047 | 520.20 | 543.2 (M + Na) | 23.7 | Scheme 3 |
| 1048 | 456.25 | 457.3 (M + H) | 22.2 | Scheme 2, Scheme 3 |
| 1049 | 498.30 | 521.3 (M + Na) | 25.7 | Scheme 3 |
| 1050 | 487.25 | 488.3 (M + H) | 24.5 | Scheme 3 |
| 1051 | 490.33 | 513.3 (M + Na) | 24.1 | Scheme 3 |
| 1052 | 479.19 | 480.2 (M + H) | 28.4 | Scheme 3 |
| 1053 | 447.20 | 448.2 (M + H) | 33.9 | Scheme 3 |
| 1054 | 502.27 | 525.3 (M + Na) | 23.6 | Scheme 3 |
| 1055 | 485.27 | 486.3 (M + H) | 34.6 | Scheme 3 |
| 1056 | 471.29 | 494.3 (M + Na) | 37.1 | Scheme 3 |
| 1125 | 485.30 | 508.3 (M + Na) | 40.9 | Scheme 3 |
| 1057 | 485.30 | 508.3 (M + Na) | 44.8 | Scheme 3 |
| 1058 | 459.15 | 482.2 (M + Na) | 36.3 | Scheme 3 |
| 1059 | 437.28 | 460.3 (M + Na) | 14.4 | Scheme 3 |
| 1060 | 504.35 | 505.4 (M + H) | 28.7 | Scheme 3 |
| 1061 | 552.27 | 575.3 (M + Na) | 27.7 | Scheme 3 |
| 1062 | 544.28 | 545.3 (M + H) | 22.8 | Scheme 3 |
| 1063 | 445.24 | 482.3 (M + Na) | 25.5 | Scheme 3 |
| 1065 | 469.24 | 492.2 (M + Na) | 30.2 | Scheme 3 |
| 1066 | 594.28 | 595.3 (M + H) | 26.5 | Scheme 3 |
| 1067 | 457.24 | 458.2 (M + H) | 31.1 | Scheme 3 |
| 1068 | 415.23 | 416.2 (M + H) | 26.7 | Scheme 3 |
| 1076 | 501.26 | 502.2 (M + H) | 28.2 | Scheme 3 |
| 1078 | 443.26 | 466.2 (M + Na) | 27.6 | Scheme 3 |
| 1094 | 495.25 | 518.3 (M + Na) | 39.3 | Scheme 3 |
| 1095 | 545.27 | 568.3 (M + Na) | 49.0 | Scheme 3 |
| 1096 | 718.42 | 719.3 (M + H) | 25.2 | Scheme 3 |
| 1097 | 526.33 | 527.3 (M + H) | 27.6 | Scheme 3 |
| 1098 | 533.30 | 556.3 (M + Na) | 45.3 | Scheme 3 |
| 1099 | 528.31 | 551.3 (M + Na) | 24.2 | Scheme 3 |
| 1100 | 443.26 | 466.3 (M + Na) | 28.4 | Scheme 3 |
| 1102 | 501.26 | 524.3 (M + Na) | 42.4 | Scheme 3 |
| 1103 | 548.28 | 549.3 (M + H) | 43.1 | Scheme 3 |
| 1104 | 562.29 | 563.3 (M + H) | 42.0 | Scheme 3 |
| 1105 | 490.33 | 491.4 (M + 1) | 25.0 | Scheme 3 |
| 1106 | 518.36 | 519.4 (M + 1) | 30.3 | Scheme 3 |
| 1107 | 513.30 | 514.3 (M + H) | 39.2 | Scheme 3 |
| 1108 | 549.16 | 550.2 (M + H) | 36.0 | Scheme 3 |
| 1111 | 430.23 | 453.2 (M + Na) | 37.7 | Scheme 1 |
| 1112 | 430.23 | 453.2 (M + Na) | 38.5 | Scheme 1 |
| 1113 | 338.20 | 339.2 (M + H) | 27.9 | Scheme 1 |
| 1114 | 414.23 | 437.2 (M + Na) | 39.3 | Scheme 1 |
| 1115 | 464.25 | 465.3 (M + H) | 44.7 | Scheme 3 |
| 1116 | 464.25 | 487.2 (M + Na) | 45.0 | Scheme 3 |
| 1117 | 414.23 | 415.2 (M + H) | 39.0 | Scheme 3 |
| 1118 | 430.23 | 431.2 (M + H) | 39.2 | — |
| 1119 | 470.12 | 493.1 (M + Na) | 41.6 | Scheme 2, Scheme 3 |
| 1120 | 442.26 | 443.2 (M + Na) | 43.0 | Scheme 4 |
| 1121[2] | 442.26 | 443.2 (M + H) | 44.5 | Scheme 4 |
| 1122[2] | 456.28 | 457.3 (M + H) | 45.6 | Scheme 4 |
| 1123 | 446.20 | 447.2 (M + H) | 39.8 | Scheme 3 |
| 1124 | 478.19 | 479.2 (M + H) | 31.0 | Scheme 3 |
| 1069 | 469.27 | 470.3 (M + H) | 37.1 | |
| 1093 | 413.21 | 414.1 (M + H) | 25.7 | Scheme 3 |
| 1110 | 443.26 | 444.3 (M + H) | 26.0 | Scheme 3 |

[1] HPLC Conditions: Purity of synthesized compounds was determined on a Waters Alliance 2690 analytical HPLC instrument and a Vydac protein and peptide C18 reverse phase column, using a linear gradient of 0% solvent B (0.1% TFA in acetonitrile) in solvent A (0.1% TFA in water) to 45% solvent B in solvent A in 45 min, measuring UV absorbance at 230 nm.
[2] Synthesized as diastereomeric pair and separated. Stereochemical assignment is tentative

TABLE 2

| Cmp. ID | $K_i$ (nm) | | | $EC_{50}$ (nm) | |
|---|---|---|---|---|---|
| | MOR | DOR | KOR | MOR | DOR |
| 1001 | 0.9 ± 0.3 | 15.7 ± 3.7 | 116 ± 30 | 3 ± 0.31 | 410 ± 138 |
| 1002 | 0.8 ± 0.04 | 8.5 ± 0.2 | 4.1 ± 0.4 | 0.463 ± 0.1 | |
| 1004 | 0.555 ± 0.242 | 7.3 ± 3.5 | 27.8 ± 0.7 | 4 ± 0.9 | 486 ± |
| 1005 | 71.4 ± 18.4 | 138.3 ± 29.8 | 632 ± 78 | 214 ± 41 | |
| 1006 | 0.34 ± 0.21 | 1.72 ± 0.61 | 71.70 ± 20 | 16.4 ± 8.18 | 2328.67 ± 1029.83 |
| 1007 | 0.11 | 6.1 | 18 | | |
| 1008 | 11 | 582 | 50 | | |
| 1009 | 0.07 | 4 | 6.6 | | |
| 1010 | 10 | 190 | 90 | | |
| 1011 | 0.13 ± 0.02 | 5.89 ± 0.76 | 15.1 ± 5.7 | 2.41 ± 0.81 | 1.7 |
| 1012 | 297 ± 72 | 1239 ± 438 | 3899 | >1000 | >10000 |
| 1013 | 0.22 ± 0.09 | 8.81 ± 2.89 | 22.47 ± 10.34 | 11.97 ± 5.77 | |
| 1014 | 1.24 ± 0.5 | 87.2 ± 56.2 | 238.42 ± 21.70 | 8.93 ± 4.00 | 627.33 ± 88.89 |
| 1015 | 25.59 ± 9.83 | 23.41 ± 10.95 | 58.92 ± 28.49 | 131 ± 21.23 | 149.5 ± 42.02 |

TABLE 2-continued

| | | | | | |
|---|---|---|---|---|---|
| 1016 | 5.33 ± 2.43 | 52.50 ± 17.8 | 28.64 ± 7.24 | 28.37 ± 4.40 | |
| 1017 | 0.42 ± 0.04 | 13.86 ± 6.7 | 65.48 ± 9.66 | 14.93 ± 5.37 | 107.75 ± 53.3 |
| 1018 | 41.33 ± 6.34 | 277 ± 47.36 | 494 | 1300 | 2000 |
| 1019 | 0.1 ± 0.02 | 4.21 ± 1.26 | 32.98 ± 0.1 | 6.49 ± 3.21 | 222 |
| 1020 | 6.25 ± 1.39 | 92.95 ± 15.06 | 787 | 598.3 ± 281.53 | 204 |
| 1021 | 38.14 ± 5.83 | 2700 | 1211 | 1395 ± 479.94 | |
| 1022 | 0.2 ± 0.02 | 2.29 ± 0.36 | 6.91 ± 0.21 | 12.53 ± 8.76 | |
| 1023 | 0.78 ± 0.27 | 25.79 ± 1.61 | 91.57 | 25.43 ± 22.24 | dns |
| 1024 | 21.14 ± 11.89 | 294.67 ± 107.92 | 1034 | dns | dns |
| 1025 | 0.1 ± 0.03 | 12.12 ± 3.52 | 24.82 | 9.7 ± 1.32 | 0.3 |
| 1026 | 0.1 ± 0.03 | 3.1 ± 0.69 | 45.48 ± 6.67 | 7.01 ± 1.49 | 0 |
| 1027 | 0.05 ± 0.01 | 5.03 ± 0.29 | 21.02 | 8.07 ± 4.81 | 430.9 ± 215.87 |
| 1028 | 50.56 ± 10.63 | 2087 | | | |
| 1029 | 0.36 ± 0.04 | 9.97 ± 0.71 | | 46.68 ± 4.12 | 0 |
| 1030 | 0.08 ± 0.01 | 2.59 | | 10.11 ± 3.25 | |
| 1031 | 0.27 ± 0.05 | 2.7 | | 39.72 ± 16.98 | |
| 1032 | 0.08 ± 0.01 | 4.61 ± 0.06 | 4.85 ± 0.66 | 2036 | dns |
| 1033 | 0.06 ± 0.01 | 0.30 ± 0.11 | | 3.61 ± 2.02 | dns |
| 1034 | 0.13 ± 0.02 | 0.38 ± 0.07 | 25.52 ± 0.85 | 4.08 ± 1.58 | dns |
| 1035 | 0.09 ± 0.00 | 4.13 ± 2.27 | | 1.44 | dns |
| 1036 | 0.18 ± 0.03 | 6.01 ± 1.31 | 20.64 ± 16.26 | 4.93 ± 1.15 | dns |
| 1037 | 0.26 ± 0.15 | 6.15 ± 2.09 | | 353.7 | dns |
| 1038 | 0.73 ± 0.00 | 19.87 ± 4.12 | 38.45 | 11.93 ± 4.96 | 260.5 |
| 1039 | 57.74 | 246 | 977 | 988 | dns |
| 1040 | 92.44 | 6.19 | | 19.04 | |
| 1041 | 0.73 | 0.86 | 13.2 | 7.25 | dns |
| 1042 | 0.35 | 0.35 | 12.10 | 14.74 | 14.18 |
| 1043 | 0.43 ± 0.18 | 11.97 ± 1.17 | 35.72 ± 23.58 | 3.21 ± 1.25 | dns |
| 1044 | 0.09 ± 0.02 | 0.26 ± 0.05 | 10.43 | 0.4 | dns |
| 1125 | 0.28 ± 0.12 | 0.67 ± 0.08 | 2.53 ± 1.52 | 3.03 ± 2.32 | dns |
| 1045 | 0.26 ± 0.09 | 2.84 ± 0.78 | 8.51 | 8.03 ± 3.15 | 134.8 |
| 1046 | 0.33 ± 0.14 | 2.74 ± 0.05 | 15.1 | 9.86 ± 3.79 | 237.3 |
| 1047 | 0.35 ± 0.05 | 3.54 ± 0.83 | 22.46 ± 8.83 | 3.45 ± 0.67 | dns |
| 1048 | 0.60 ± 0.12 | 32.27 ± 7.57 | 169.73 ± 49.06 | 9.20 ± 4.58 | 1588.15 ± 737.99 |
| 1049 | 0.17 ± 0.06 | 23.27 ± 2.51 | 11.92 ± 6.13 | 0.35 ± 0.11 | dns |
| 1050 | 0.35 ± 0.11 | 5.48 ± 0.81 | 115.75 ± 65.12 | 5.54 ± 0.12 | dns |
| 1051 | 0.18 ± 0.03 | 9.50 ± 1.22 | 7.03 ± 1.36 | 1.22 ± 0.07 | dns |
| 1052 | 3.01 ± 1.87 | 2.92 ± 0.41 | 25.99 ± 7.12 | 12.87 ± 1.35 | dns |
| 1053 | 0.45 ± 0.11 | 5.08 ± 0.52 | 10.85 ± 6.24 | 4.67 ± 1.44 | dns |
| 1054 | 0.17 ± 0.02 | 16.70 ± 2.47 | 9.63 ± 0.40 | 0.50 ± 0.05 | 25.86 ± 16.87 |
| 1055 | 0.18 ± 0.04 | 1.88 ± 0.53 | 80 ± 20 | 7.05 ± 2.32 | 384 ± 296 |
| 1056 | 0.64 ± 0.08 | 5.89 ± 1.50 | 98.36 ± 18.23 | 23.31 ± 6.94 | 306.67 ± 28.62 |
| 1126 | 0.75 ± 0.4 | 3.55 ± 0.46 | 34.4 ± 4.7 | 17.9 ± 5.83 | 200 ± 77 |
| 1057 | 0.91 ± 0.40 | 3.78 ± 0.66 | 64.72 ± 17.80 | 9.87 ± 3.55 | 238.17 ± 39.26 |
| 1058 | 21.72 ± 8.06 | 45.86 ± 22.65 | 208 ± 16 | 859 | |
| 1059 | 16.64 ± 8.63 | 1557.17 ± 288.28 | 11.69 ± 1.56 | 90.52 ± 73.23 | |
| 1060 | 0.22 ± 0.10 | 36.53 ± 18.89 | 2.44 ± 0.99 | dns | dns |
| 1061 | 0.17 ± 0.03 | 13.62 ± 1.27 | 48.49 ± 17.46 | 8.88 ± 2.71 | dns |
| 1062 | 0.05 ± 0.01 | 0.77 ± 0.23 | 16.18 ± 7.94 | 23.71 ± 26.75 | dns |
| 1063 | 0.24 ± 0.11 | 3.08 ± 1.00 | 29.89 ± 10.38 | 2.50 ± 0.45 | 63.33 ± 12.19 |
| 1065 | 0.11 ± 0.03 | 4.76 ± 1.90 | 41.40 ± 22.44 | 1.14 ± 0.49 | dns |
| 1066 | 0.16 ± 0.01 | 3.05 ± 0.88 | 59.25 ± 12.37 | 1.25 ± 0.44 | dns |
| 1067 | 0.88 ± 0.40 | 1.32 ± 0.37 | 35.81 ± 16.77 | 5.64 ± 0.35 | 1520.18 ± 889.26 |
| 1068 | 1.11 ± 0.44 | 13.44 ± 4.32 | 165.49 ± 110.16 | 11.79 ± 5.77 | |
| 1076 | 0.14 ± 0.01 | 2.16 ± 1.15 | 44.79 ± 16.89 | 0.78 ± 0.20 | 4.62 ± 1.90 |
| 1078 | 0.75 ± 0.03 | 2.02 ± 0.21 | 17.67 ± 2.24 | 3.14 ± 1.51 | 30.86 |
| 1094 | 0.34 ± 0.08 | 3.49 ± 0.55 | 27.94 ± 6.24 | 9.77 ± 6.34 | 74.90 ± 61.48 |
| 1095 | 3.14 ± 1 | 71 ± 17 | 800 ± 115 | 15.56 ± 6.86 | dns |
| 1096 | 0.31 ± 0.16 | 2.56 ± 0.53 | 7.17 ± 2.38 | 5.89 ± 0.68 | dns |
| 1097 | 0.07 ± 0.03 | 2.41 | 0.71 | 2.32 ± 0.21 | |
| 1098 | 0.64 ± 0.34 | 0.69 ± 0.03 | 27.48 ± 7.81 | 44.4 ± 16.6 | dns |
| 1099 | 0.15 ± 0.04 | 2.61 ± 0.79 | 19.45 ± 8.53 | 1.84 ± 0.41 | 171.76 ± 65.76 |
| 1100 | 2.63 | 1.09 | 18.28 | | |
| 1102 | 1.01 ± 0.28 | 4.2 | 48.67 | 4.91 ± 0.28 | dns |
| 1103 | 0.36 | 2.17 | 29.42 | 27.29 | dns |
| 1104 | 0.36 | 2.17 | 29.43 | 4.18 | dns |
| 1105 | 1.14 | 14.08 | 1.66 | | |
| 1106 | 0.54 | 16.96 | 3.08 | | |
| 1107 | 0.35 | 1.95 | 32.66 | | |
| 1108 | 0.49 | 1.35 | 33.29 | | |
| 1111 | 0.046 ± 0.028 | 8.65 ± 1.61 | 58.27 ± 14.07 | 4.85 ± 2.14 | 118 ± 2.45 |
| 1112 | 6.07 ± 2.41 | 260 ± 62.87 | 354 ± 37.11 | 654 ± 360.89 | |
| 1113 | 25.65 ± 10.87 | 639.5 ± 217.6 | 2055.5 ± 581.97 | | |
| 1114 | 0.55 ± 0.09 | 29.92 ± 10.11 | 143.35 ± 45.44 | 18.27 ± 8.14 | |
| 1115 | 5.44 ± 2.70 | 45.53 ± 26.92 | 130.94 ± 42.35 | | |
| 1116 | 0.24 ± 0.12 | 6.03 ± 0.2 | 315.89 ± 0.91 | | |
| 1117 | 0.57 ± 0.32 | 3.99 ± 1.31 | 20.90 ± 4.12 | 9.51 ± 3.30 | 180.5 ± 28.17 |
| 1118 | 0.33 ± 0.09 | 12.99 ± 1.01 | 38.45 ± 5.39 | 43.01 ± 14.01 | 0 |
| 1119 | 1.53 ± 0.64 | 104.99 ± 10.53 | | 117.8 ± 76 | dns |
| 1120 | 0.08 ± 0.02 | 5.85 ± 0.58 | | 15.95 ± 1.94 | dns |

TABLE 2-continued

| | | | | | |
|---|---|---|---|---|---|
| 1121 | 0.32 ± 0.10 | 15.83 ± 4.72 | | dns | 109.34 ± 80.72 |
| 1122 | 0.36 ± 0.08 | 6.50 ± 0.66 | | 16.04 ± 4.74 | 1093.33 ± 654.12 |
| 1123 | 0.15 ± 0.04 | 4.79 ± 1.11 | 48.39 ± 23.12 | 1.92 ± 0.54 | dns |
| 1124 | 0.06 ± 0.01 | 2.34 ± 1.42 | 27.21 ± 5.99 | 0.72 ± 0.11 | 126.39 ± 72.52 |
| 1069 | 0.39 ± 0.14 | 2.26 ± 0.80 | 6.62 ± 2.57 | 1.12 ± 0.52 | 569.85 ± 297.82 |
| 1093 | 2800 ± 5 | 4000 ± 200 | 1320 | | dns |
| 1110 | 0.41 ± 0.15 | 22.72 ± 1.85 | 40.23 ± 18.89 | 71.67 ± 23.02 | dns |
| 1127 | 0.05 | 4.6 | 44 | 37 | 23 |
| 1128 | 0.2 | 2.2 | 27 | 1.2 | 36 |
| 1129 | 0.3 | 3.7 | 21 | 1.8 | 50 |
| 1130 | 0.6 | 2.3 | 700 | 4 | dns |
| 1131 | 0.35 | 22 | 1.9 | 8 | 280 |

| Cmp. ID | $EC_{50}$ (nm) KOR | % stimulation MOR | DOR | KOR |
|---|---|---|---|---|
| 1001 | 488 ± 142 | 80.6 ± 4.7 | 12.6 ± 5.5 | 3.9 ± 0.9 |
| 1002 | 7.2 ± 0.4 | 65.6 ± 4.4 | 2.2 ± 2.2 | 8.3 ± 2.4 |
| 1004 | 2219 ± 1019 | 102.2 ± 4.6 | 4.3 ± 4.3 | 44 ± 8.2 |
| 1005 | | 72.2 ± 3.6 | 0 | 1.6 ± 1.4 |
| 1006 | 5008 ± 1016.63 | 83.07 ± 3.25 | 39.27 ± 5.45 | 38.23 ± 3.42 |
| 1007 | | 99 | 13 | 14 |
| 1008 | | 55 | 3 | 0 |
| 1009 | | 69 | 16 | 9 |
| 1010 | | 58 | 12 | 0 |
| 1011 | 773.1 ± 26.47 | 35.90 ± 5.28 | 2.50 ± 2.50 | 34.57 ± 1.11 |
| 1012 | | 18 | 22 | 0 |
| 1013 | 542.67 ± 148.23 | 20.20 ± 7.11 | 0 ± 0 | 23.67 ± 0.83 |
| 1014 | 4074 | 87.8 ± 2.0 | 44.93 ± 8.25 | 28.93 ± 12.28 |
| 1015 | | 15.83 ± 3.75 | 19.53 ± 2.83 | −1.84 ± 1.83 |
| 1016 | | 40.13 ± 10.73 | 0.82 ± 3.63 | −0.01 ± 0.01 |
| 1017 | 957 | 67.98 ± 2.33 | 9.8 ± 5.49 | 23.65 |
| 1018 | | 16.57 ± 16.57 | 19.6 | |
| 1019 | 1084 | 76.64 ± 2.66 | 15.8 | 37.3 |
| 1020 | | 60.41 ± 2.04 | 16 | |
| 1021 | | 34.79 ± 2.52 | | |
| 1022 | | 24.54 ± 0.29 | 0 | |
| 1023 | | 18.14 ± 4.92 | dns | |
| 1024 | | dns | dns | |
| 1025 | | 52.9 ± 4.46 | 1.18 ± 1.18 | |
| 1026 | 1819 | 61.2 ± 6.93 | 0 | 47.32 |
| 1027 | 791.2 | 72.15 ± 2.41 | 7.42 ± 5.57 | 55.08 |
| 1028 | | 13.78 ± 1.27 | 0 | |
| 1029 | | 35.68 ± 2.58 | 0 | |
| 1030 | | 27.21 ± 2.11 | | |
| 1031 | | 30.51 ± 1.74 | | |
| 1032 | 0 | 33.58 | dns | 0 |
| 1033 | | 51.97 ± 7.70 | dns | |
| 1034 | | 63.23 ± 12.56 | dns | |
| 1035 | | 32.93 | dns | |
| 1036 | | 69.09 ± 5.74 | dns | |
| 1037 | | 10.93 | dns | |
| 1038 | | 16.18 ± 3.43 | 10.52 | |
| 1039 | | 17.89 | dns | |
| 1040 | | 8.03 | | |
| 1041 | | 73.01 | dns | |
| 1042 | | 75.08 | 30.15 | |
| 1043 | | 92.40 ± 8.06 | dns | |
| 1044 | | 82.5 | dns | |
| 1125 | dns | 69.49 ± 10.43 | dns | dns |
| 1045 | | 98.38 ± 2.54 | 32.46 | |
| 1046 | | 94.66 ± 4.19 | 20.31 | |
| 1047 | | 81.62 ± 1.48 | dns | |
| 1048 | dns | 97.92 ± 4.71 | 24.53 ± 3.25 | dns |
| 1049 | dns | 110.87 ± 4.65 | dns | dns |
| 1050 | dns | 87.55 ± 11.96 | dns | dns |
| 1051 | dns | 36.16 ± 8.14 | dns | dns |
| 1052 | 1307 | 68.86 ± 10.31 | dns | 38.45 |
| 1053 | 1120 | 51.63 ± 6.43 | dns | 22.36 |
| 1054 | 107.6 | 104.92 ± 4.56 | dns | dns |
| 1055 | 930 ± 600 | 86 ± 3 | 30 ± 3 | 32 ± 2 |
| 1056 | dns | 89.47 ± 6.27 | 35.73 ± 2.62 | dns |
| 1126 | dns | 85 ± 2.0 | 24.85 ± 4.43 | dns |
| 1057 | dns | 83.20 ± 4.60 | 57.90 ± 13.97 | dns |
| 1058 | dns | 12.57 | | dns |
| 1059 | | dns | | |
| 1060 | 92.09 ± 15.47 | dns | dns | 71.62 ± 4.38 |
| 1061 | dns | 37.78 ± 2.55 | dns | dns |
| 1062 | 233.65 ± 70.10 | 99.62 ± 1.92 | dns | 34.24 ± 8.24 |

TABLE 2-continued

|  |  |  |  |  |
|---|---|---|---|---|
| 1063 | dns | 84.06 ± 0.96 | 50.80 ± 9.61 | dns |
| 1065 | dns | 97.94 ± 1.43 | 13.89 | dns |
| 1066 | dns | 55.15 ± 2.83 | dns | dns |
| 1067 | 291.27 ± 32.52 | 51.28 ± 8.48 | 37.42 ± 6.31 | 69.11 ± 5.04 |
| 1068 | 933 ± 219.48 | 23.69 ± 5.88 | dns | 57.11 ± 2.63 |
| 1076 | 1480.83 ± 638.73 | 95.82 ± 10.21 | 44.57 ± 3.75 | 16.09 ± 5.54 |
| 1078 | 900.25 ± 326.39 | 80.19 ± 7.89 | 21.36 | 26.35 ± 5.75 |
| 1094 | 289.8 | 103 ± 5 | 36.73 ± 5.53 | 29.04 |
| 1095 | dns | 100 ± 2.48 | dns | dns |
| 1096 | dns | 86 ± 8 | dns | dns |
| 1097 |  | 93 ± 1.67 |  |  |
| 1098 | dns | 78.36 ± 1.26 | dns | dns |
| 1099 | dns | 96.09 ± 1.76 | 29 ± 6.78 | dns |
| 1100 |  |  |  |  |
| 1102 |  | 70.53 ± 2.61 | dns |  |
| 1103 |  | 62.69 | dns |  |
| 1104 |  | 79.01 | dns |  |
| 1105 |  |  |  |  |
| 1106 |  |  |  |  |
| 1107 |  |  |  |  |
| 1108 |  |  |  |  |
| 1111 | 662.33 ± 151.62 | 69.7 ± 5.97 | 8.97 ± 4.78 | 28.30 ± 6.71 |
| 1112 |  | 7.18 ± 2.41 | 2.48 ± 3.08 | -.061 ± 0.45 |
| 1113 |  | 3.44 ± 2.09 | -0.76 ± 0.62 | -1.05 |
| 1114 | 1603 | 42.63 ± 8.65 | 3.07 ± 1.82 | 3.70 ± 4.06 |
| 1115 | 200.45 | 0.34 ± 3.26 | -2.57 ± 4.30 | 3.82 ± 3.20 |
| 1116 | 236.6 | -1.10 ± 1.61 | 1.75 ± 1.44 | 5.57 ± 8.53 |
| 1117 | 321.02 ± 176.38 | 28.66 ± 2.39 | 21.2 ± 10.72 | 45.58 ± 1.77 |
| 1118 |  | 41.86 ± 8.97 | 1.65 ± 1.65 |  |
| 1119 |  | 20.73 ± 2.91 | dns |  |
| 1120 |  | 72.26 ± 3.67 | dns |  |
| 1121 |  | dns | 14.35 ± 4.34 |  |
| 1122 | 2095 | 75.43 ± 4.06 | 16.01 ± 2.78 | 77.82 |
| 1123 | 336.84 ± 204.99 | 79.92 ± 7.51 | dns | 10.28 ± 5.17 |
| 1124 | 720.71 ± 317.14 | 94.46 ± 3.04 | 45.23 ± 5.62 | 35.83 ± 2.15 |
| 1069 | 1002 | 95.18 ± 3.99 | 50.39 ± 13.66 | 78.42 |
| 1093 | dns |  |  | dns |
| 1110 |  | 73.06 ± 4.22 | dns |  |
| 1127 | dns | 75 | 48 | dns |
| 1128 | 300 | 73 | 69 | 30 |
| 1129 | 600 | 70 | 42 | 17 |
| 1130 | dns | 60 | dns | dns |
| 1131 | 190 | 61 | 17 | 18 |

TABLE 3

| Compound | C-8 substitution | Antinociceptive activity | Duration |
|---|---|---|---|
| 1041 | Benzyl | Inactive | — |
| 1100 | Methyl | Fully efficacious | 90 min |
| 1127 | Ethyl | Fully efficacious | 60 min |
| 1056 | n-propyl | Inactive | — |
| 1126 | n-butyl | Fully efficacious | 150 min |
| 1057 | t-butyl | Partially active | — |
| 1090 | Fluoro | Inactive | — |
| 1129 | Trifluoromethyl | Inactive | — |
| 1097 | $CH_2$piperidine | Inactive | — |
| 1099 | $CH_2$morpholine | Inactive | — |
| 1131 | $CH_2$piperazine | — | — |
| 1098 | Ethylphenyl | Inactive | — |
| 1094 | 3-furanyl | Inactive | — |
| 1102 | Ethyl ester | Fully efficacious | 150 min |
| 1103 | Phenyl amide | — | — |
| 1104 | Benzyl amide | Inactive | — |
| 1128 | Bromo | Inactive | — |
| 1130 | Carboxylic acid | Inactive | — |

What is claimed:
1. A compound of Formula (I):

(I)

wherein:
A is:

(B)

E is $CR^1$ or N;
G is S, or $SO_2$;
n is 0, 1, or 2;

each $R^1$ independently is H, halo, $C_{1-6}$alkyl, $C_{1-6}$haloalkyl, $C_{0-6}$alkylenearyl, $C_{0-6}$alkyleneheteroaryl, $C_{0-6}$alkylenecycloalkyl, $C_{0-6}$alkyleneheterocycloalkyl, $C_{0-3}$alkyleneOR$^4$, SR$^4$, SO$_2$R$^4$, C(O)N(R$^4$)$_2$, C(O)OR$^4$, or C(O)SR$^4$; and at least one $R^1$ is other than H;

each $R^2$ independently is H or $C_{1-6}$alkyl;

$R^3$ is H, $C_{1-6}$alkyl, $C_{0-3}$alkyleneC(O)R$^4$, $C_{0-3}$alkyleneC(O)OR$^4$ or $C_{0-3}$alkyleneC(O)NHR$^4$;

$R^4$ is H, $C_{1-6}$alkyl, $C_{0-3}$alkylene-$C_{3-6}$cycloalkyl, $C_{1-3}$alkylene-OC$_{1-6}$alkyl, or $C_{0-3}$alkylenearyl;

$R^5$ is H, $C_{1-3}$ alkyl, or $C_{3-6}$cycloalkyl;

each $R^6$ independently is H, $C_{1-3}$alkyl, OH, $C_{1-3}$alkoxy, halo, or C(O)N(R$^3$)$_2$, and at least one $R^6$ is not H; and $R^7$ is H, $C_{1-3}$alkyl, OH, $C_{1-3}$alkoxy, halo, or C(O)N(R$^3$)$_2$; or a pharmaceutically acceptable salt thereof.

2. The compound of claim 1, wherein A is selected from the group consisting of

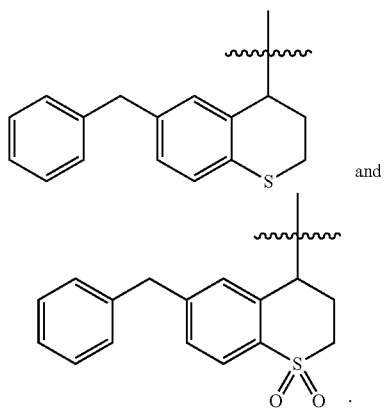
and

3. The compound of claim 1, wherein each $R^1$ independently is:
H, F, Br, CF$_3$, methyl, ethyl, propyl, n-butyl, or t-butyl.

4. The compound of claim 1, wherein:
(a) at least one $R^2$ is CH$_3$; or
(b) at least one $R^2$ is H; or
(c) each $R^2$ is H.

5. The compound of claim 1, wherein $R^5$ is H, methyl, or cyclopropyl.

6. The compound of claim 1, wherein each $R^6$ independently is H, CH$_3$, or Cl.

7. The compound of claim 1, wherein $R^7$ is H, OH, OCH$_3$, Cl, or C(O)NH$_2$.

8. The compound of claim 1, wherein each $R^1$ independently is phenyl, benzyl, naphthyl,

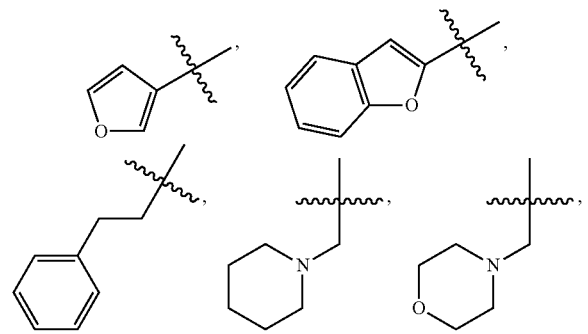

-continued

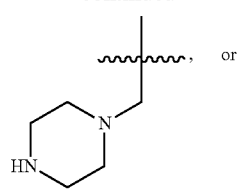

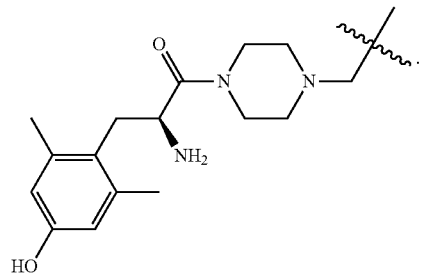

9. The compound of claim 1, wherein each $R^1$ independently is OH, OCH$_3$, OPh, COOH,

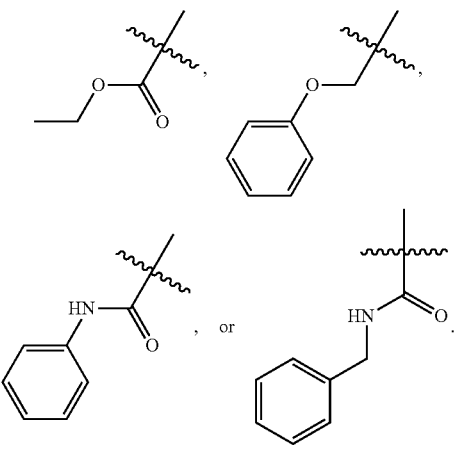

10. A compound selected from the group consisting of:

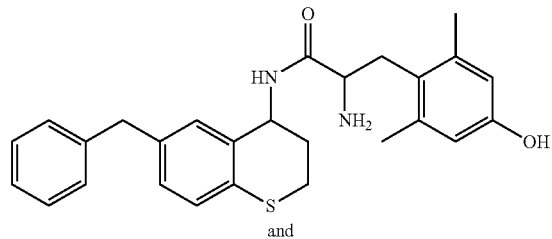
and

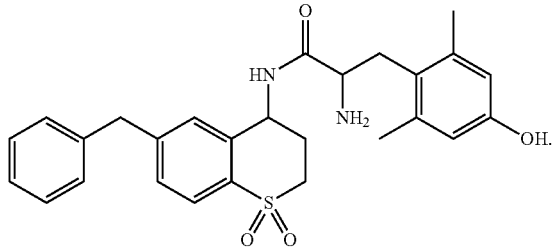

11. A pharmaceutical formulation comprising the compound of claim 1 and a pharmaceutically acceptable excipient.

* * * * *